US012582520B2

(12) United States Patent
Diedering et al.

(10) Patent No.: US 12,582,520 B2
(45) Date of Patent: Mar. 24, 2026

(54) IMPLANT DELIVERY

(71) Applicant: 4C Medical Technologies, Inc., Maple Grove, MN (US)

(72) Inventors: Jason S. Diedering, Minneapolis, MN (US); Jonathan Berndt, Crystal, MN (US); Sounthara Khouengboua, Chaska, MN (US); Paul Thompson, Minnetonka, MN (US); Shelby Jo Byron, Maple Grove, MN (US)

(73) Assignee: 4C Medical Technologies, Inc., Maple Grove, MN (US)

( * ) Notice: Subject to any disclaimer, the term of this patent is extended or adjusted under 35 U.S.C. 154(b) by 0 days.

(21) Appl. No.: 19/185,797

(22) Filed: Apr. 22, 2025

(65) Prior Publication Data

US 2025/0248806 A1 Aug. 7, 2025

Related U.S. Application Data

(63) Continuation of application No. 18/615,450, filed on Mar. 25, 2024.

(Continued)

(51) Int. Cl.
*A61F 2/24* (2006.01)

(52) U.S. Cl.
CPC .......... *A61F 2/2418* (2013.01); *A61F 2/2427* (2013.01); *A61F 2/2439* (2013.01);
(Continued)

(58) Field of Classification Search
CPC .................................................... A61F 2/2427
See application file for complete search history.

(56) References Cited

U.S. PATENT DOCUMENTS

| | | | |
|---|---|---|---|
| 4,424,833 | A | 1/1984 | Spector |
| 4,503,569 | A | 3/1985 | Dotter |

(Continued)

FOREIGN PATENT DOCUMENTS

| | | | |
|---|---|---|---|
| AU | 2014203064 | B2 | 6/2015 |
| AU | 2015230879 | A1 | 10/2015 |

(Continued)

OTHER PUBLICATIONS

4C Medical's Alta Valve: The First-in-Human Experience, Josep Rodes-Cabau, MD, Sep. 21, 2018.

(Continued)

*Primary Examiner* — Suba Ganesan
(74) *Attorney, Agent, or Firm* — Weiss & Arons LLP

(57) ABSTRACT

Apparatus and methods for an implant are provided. The implant may have a constrained configuration and a relaxed configuration. The implant may include a strut having an end that may be captured by a hub and may define a reference angle in the relaxed configuration. The implant may include a swivel body that may engage a shaft of a delivery cable and may be rotated through the reference angle. The apparatus may include a pusher catheter to push the implant. The delivery cable may engage the implant. The apparatus may include gauge handle that may include a force gauge to indicate the presence of a force acting on the implant. The apparatus may include a bushing that may be fixed to an end of a pusher catheter. The bushing may move along a delivery catheter lumen and may guide the implant to a keyed position at the bushing.

64 Claims, 42 Drawing Sheets

Related U.S. Application Data

(60) Provisional application No. 63/532,489, filed on Aug. 14, 2023, provisional application No. 63/454,350, filed on Mar. 24, 2023.

(52) U.S. Cl.
CPC ..... *A61F 2/2436* (2013.01); *A61F 2230/0069* (2013.01); *A61F 2250/0006* (2013.01)

(56) References Cited

U.S. PATENT DOCUMENTS 4,733,665 A 3/1988 Palmaz
4,878,906 A 11/1989 Lindemann
5,190,528 A 3/1993 Fonger
5,415,667 A 5/1995 Frater
5,441,483 A 8/1995 Avitall
5,693,083 A 12/1997 Baker
5,693,089 A 12/1997 Inoue
5,776,188 A 7/1998 Shepherd
5,843,090 A 12/1998 Schuetz
5,928,258 A 7/1999 Khan
5,957,949 A 9/1999 Leonhardt
5,968,070 A 10/1999 Bley
6,123,723 A 9/2000 Konya
6,152,144 A 11/2000 Lesh
6,231,602 B1 5/2001 Carpentier
6,287,334 B1 9/2001 Moll
6,319,280 B1 11/2001 Schoon
6,319,281 B1 11/2001 Patel
6,332,893 B1 12/2001 Mortier
6,371,983 B1 4/2002 Lane
6,409,758 B2 6/2002 Stobie
6,425,916 B1 7/2002 Garrison
6,471,718 B1 10/2002 Staehle
6,494,909 B2 12/2002 Greenhalgh
6,503,272 B2 1/2003 Duerig
6,540,782 B1 4/2003 Snyders
6,569,196 B1 5/2003 Vesely
6,589,275 B1 7/2003 Ivancev
6,702,826 B2 3/2004 Liddicoat
6,738,655 B1 5/2004 Sen
6,790,231 B2 9/2004 Liddicoat
6,790,237 B2 9/2004 Stinson
6,821,297 B2 11/2004 Snyders
6,830,585 B1 12/2004 Artof
6,840,957 B2 1/2005 Dimatteo
6,875,231 B2 4/2005 Anduiza
7,011,671 B2 3/2006 Welch
7,041,132 B2 5/2006 Quijano
7,044,966 B2 5/2006 Svanidze
7,125,420 B2 10/2006 Rourke
7,153,324 B2 12/2006 Case
7,252,682 B2 8/2007 Seguin
7,276,077 B2 10/2007 Zadno-Azizi
7,276,078 B2 10/2007 Spenser
7,291,168 B2 11/2007 Macoviak
7,364,588 B2 4/2008 Mathis
7,381,220 B2 6/2008 Macoviak
7,442,204 B2 10/2008 Schwammenthal
7,445,631 B2 11/2008 Salahieh
7,455,689 B2 11/2008 Johnson
7,510,572 B2 3/2009 Gabbay
7,524,331 B2 4/2009 Birdsall
7,611,534 B2 11/2009 Kapadia
7,704,277 B2 4/2010 Zakay
7,749,266 B2 7/2010 Forster
7,758,491 B2 7/2010 Buckner
7,780,723 B2 8/2010 Taylor
7,789,909 B2 9/2010 Andersen
7,935,144 B2 5/2011 Robin
7,959,672 B2 6/2011 Salahieh
7,967,853 B2 6/2011 Eidenschink
7,998,196 B2 8/2011 Mathison
8,012,201 B2 9/2011 Lashinski
8,016,877 B2 9/2011 Seguin
8,021,420 B2 9/2011 Dolan
8,029,556 B2 10/2011 Rowe
D648,854 S 11/2011 Braido
8,052,592 B2 11/2011 Goldfarb
8,057,493 B2 11/2011 Goldfarb
8,070,802 B2 12/2011 Lamphere
8,083,793 B2 12/2011 Lane
D653,341 S 1/2012 Braido
D653,342 S 1/2012 Braido
8,092,524 B2 1/2012 Nugent
8,142,492 B2 3/2012 Forster
8,142,494 B2 3/2012 Rahdert et al.
8,147,541 B2 4/2012 Forster
D660,433 S 5/2012 Braido
D660,967 S 5/2012 Braido
8,167,932 B2 5/2012 Bourang
8,236,049 B2 8/2012 Rowe
8,246,677 B2 8/2012 Ryan
8,252,051 B2 8/2012 Chau
8,287,538 B2 10/2012 Brenzel et al.
8,308,798 B2 11/2012 Pintor
8,348,998 B2 1/2013 Pintor
8,348,999 B2 1/2013 Kheradvar
8,366,768 B2 2/2013 Zhang
8,398,708 B2 3/2013 Meiri
8,409,275 B2 4/2013 Matheny
8,414,644 B2 4/2013 Quadri
8,414,645 B2 4/2013 Dwork
8,439,970 B2 5/2013 Jimenez
8,454,686 B2 6/2013 Alkhatib
8,465,541 B2 6/2013 Dwork
8,491,650 B2 7/2013 Wiemeyer
8,512,400 B2 8/2013 Tran
8,518,106 B2 8/2013 Duffy
8,535,373 B2 9/2013 Stacchino
8,562,673 B2 10/2013 Yeung
8,568,472 B2 10/2013 Marchand
8,579,963 B2 11/2013 Tabor
8,579,964 B2 11/2013 Lane
8,603,159 B2 12/2013 Seguin
8,623,075 B2 1/2014 Murray, III
8,636,764 B2 1/2014 Miles
8,641,757 B2 2/2014 Pintor
8,657,870 B2 2/2014 Turovskiy
8,663,318 B2 3/2014 Ho
8,679,176 B2 3/2014 Matheny
8,721,715 B2 5/2014 Wang
8,740,976 B2 6/2014 Tran
8,747,459 B2 6/2014 Nguyen
8,747,461 B2 6/2014 Centola
8,764,793 B2 7/2014 Lee
8,764,820 B2 7/2014 Dehdashtian
8,778,020 B2 7/2014 Gregg
8,790,396 B2 7/2014 Bergheim
8,795,354 B2 8/2014 Benichou
8,795,357 B2 8/2014 Yohanan
8,805,466 B2 8/2014 Salahieh
8,814,931 B2 8/2014 Wang
8,828,043 B2 9/2014 Chambers
8,828,051 B2 9/2014 Javois
8,845,711 B2 9/2014 Miles
8,845,722 B2 9/2014 Gabbay
8,852,271 B2 10/2014 Murray, III
8,852,272 B2 10/2014 Gross
8,870,949 B2 10/2014 Rowe
8,876,897 B2 11/2014 Kheradvar
8,906,022 B2 12/2014 Krinke et al.
8,926,692 B2 1/2015 Dwork
8,956,402 B2 2/2015 Cohn
8,956,405 B2 2/2015 Wang
8,961,518 B2 2/2015 Kyle et al.
8,986,372 B2 3/2015 Murry, III
8,986,374 B2 3/2015 Cao
8,986,375 B2 3/2015 Garde
8,998,980 B2 4/2015 Shipley
8,998,982 B2 4/2015 Richter
9,005,273 B2 4/2015 Salahieh
9,011,527 B2 4/2015 Li

(56) References Cited

U.S. PATENT DOCUMENTS

| | | | |
|---|---|---|---|
| D730,520 | S | 5/2015 | Braido |
| D730,521 | S | 5/2015 | Braido |
| 9,023,101 | B2 | 5/2015 | Krahbichler |
| 9,050,188 | B2 | 6/2015 | Schweich, Jr. |
| 9,060,855 | B2 | 6/2015 | Tuval |
| 9,060,857 | B2 | 6/2015 | Nguyen |
| 9,060,858 | B2 | 6/2015 | Thornton |
| 9,061,119 | B2 | 6/2015 | Le |
| 9,066,800 | B2 | 6/2015 | Clague |
| 9,072,603 | B2 | 7/2015 | Tuval |
| 9,101,471 | B2 | 8/2015 | Kleinschrodt |
| 9,119,717 | B2 | 9/2015 | Wang |
| 9,132,008 | B2 | 9/2015 | Dwork |
| 9,132,009 | B2 | 9/2015 | Hacohen |
| 9,138,313 | B2 | 9/2015 | Mcguckin, Jr. |
| 9,144,493 | B2 | 9/2015 | Carr |
| 9,144,494 | B2 | 9/2015 | Murray |
| 9,155,619 | B2 | 10/2015 | Liu |
| 9,161,835 | B2 | 10/2015 | Rankin |
| 9,173,737 | B2 | 11/2015 | Hill |
| 9,192,466 | B2 | 11/2015 | Kovalsky |
| 9,226,820 | B2 | 1/2016 | Braido |
| 9,232,942 | B2 | 1/2016 | Seguin |
| 9,232,996 | B2 | 1/2016 | Sun |
| 9,248,016 | B2 | 2/2016 | Oba |
| 9,259,315 | B2 | 2/2016 | Zhou |
| 9,271,856 | B2 | 3/2016 | Duffy |
| 9,277,993 | B2 | 3/2016 | Gamarra |
| 9,289,289 | B2 | 3/2016 | Rolando |
| 9,289,292 | B2 | 3/2016 | Anderl |
| 9,295,547 | B2 | 3/2016 | Costello |
| 9,295,549 | B2 | 3/2016 | Braido |
| 9,301,836 | B2 | 4/2016 | Buchbinder |
| 9,301,839 | B2 | 4/2016 | Stante |
| 9,320,597 | B2 | 4/2016 | Savage |
| 9,320,599 | B2 | 4/2016 | Salahieh |
| 9,326,853 | B2 | 5/2016 | Olson |
| 9,326,854 | B2 | 5/2016 | Casley |
| 9,333,075 | B2 | 5/2016 | Biadillah |
| 9,345,572 | B2 | 5/2016 | Cerf |
| 9,351,831 | B2 | 5/2016 | Braido |
| 9,358,108 | B2 | 6/2016 | Bortlein |
| 9,364,325 | B2 | 6/2016 | Alon |
| 9,364,637 | B2 | 6/2016 | Rothstein |
| 9,370,422 | B2 | 6/2016 | Wang |
| 9,387,106 | B2 | 7/2016 | Stante |
| 9,402,720 | B2 | 8/2016 | Richter |
| 9,414,910 | B2 | 8/2016 | Lim |
| 9,414,917 | B2 | 8/2016 | Young |
| 9,427,316 | B2 | 8/2016 | Schweich, Jr. |
| 9,439,763 | B2 | 9/2016 | Geist |
| 9,439,795 | B2 | 9/2016 | Wang |
| 9,480,560 | B2 | 11/2016 | Quadri |
| 9,498,370 | B2 | 11/2016 | Kyle et al. |
| 9,504,569 | B2 | 11/2016 | Malewicz |
| 9,522,062 | B2 | 12/2016 | Tuval |
| 9,566,152 | B2 | 2/2017 | Schweich, Jr. |
| 9,579,194 | B2 | 2/2017 | Elizondo |
| 9,579,197 | B2 | 2/2017 | Duffy |
| 9,622,863 | B2 | 4/2017 | Karapetian |
| 9,717,592 | B2 | 8/2017 | Thapliyal |
| 9,730,791 | B2 | 8/2017 | Ratz |
| 9,737,400 | B2 | 8/2017 | Fish |
| 9,737,401 | B2 | 8/2017 | Conklin |
| 9,750,604 | B2 | 9/2017 | Naor |
| 9,763,780 | B2 | 9/2017 | Morriss |
| 9,795,477 | B2 | 10/2017 | Tran |
| 9,801,711 | B2 | 10/2017 | Gainor |
| 9,827,093 | B2 | 11/2017 | Cartledge |
| 9,839,517 | B2 | 12/2017 | Centola |
| 9,839,765 | B2 | 12/2017 | Morris |
| 9,861,477 | B2 | 1/2018 | Backus |
| 9,872,765 | B2 | 1/2018 | Zeng |
| 9,877,830 | B2 | 1/2018 | Lim |
| 9,968,443 | B2 | 5/2018 | Bruchman |
| 10,004,601 | B2 | 6/2018 | Tuval |
| 10,016,274 | B2 | 7/2018 | Tabor |
| 10,016,275 | B2 | 7/2018 | Nyuli |
| 10,022,132 | B2 | 7/2018 | Wlodarski et al. |
| 10,034,750 | B2 | 7/2018 | Morriss |
| 10,039,637 | B2 | 8/2018 | Maimon |
| 10,039,642 | B2 | 8/2018 | Hillukka |
| 10,098,735 | B2 | 10/2018 | Lei |
| 10,098,763 | B2 | 10/2018 | Lei |
| 10,117,742 | B2 | 11/2018 | Braido |
| 10,143,551 | B2 | 12/2018 | Braido |
| 10,182,907 | B2 | 1/2019 | Lapeyre |
| 10,195,023 | B2 | 2/2019 | Wrobel |
| 10,226,340 | B2 | 3/2019 | Keren |
| 10,231,834 | B2 | 3/2019 | Keidar |
| 10,238,490 | B2 | 3/2019 | Gifford, III |
| 10,245,145 | B2 | 4/2019 | Mantanus |
| 10,258,464 | B2 | 4/2019 | Delaloye |
| 10,299,917 | B2 | 5/2019 | Morriss |
| 10,321,990 | B2 | 6/2019 | Braido |
| 10,327,892 | B2 | 6/2019 | O'Connor |
| 10,327,893 | B2 | 6/2019 | Maiorano |
| 10,350,065 | B2 | 7/2019 | Quadri |
| 10,357,360 | B2 | 7/2019 | Hariton |
| 10,368,982 | B2 | 8/2019 | Weber |
| 10,376,363 | B2 | 8/2019 | Quadri |
| 10,383,725 | B2 | 8/2019 | Chambers |
| 10,390,943 | B2 | 8/2019 | Hernandez |
| 10,405,974 | B2 | 9/2019 | Hayes |
| 10,433,961 | B2 | 10/2019 | Mclean |
| 10,470,880 | B2 | 11/2019 | Braido |
| 10,492,907 | B2 | 12/2019 | Duffy |
| 10,500,041 | B2 | 12/2019 | Valdez |
| 10,507,107 | B2 | 12/2019 | Nathe |
| 10,512,537 | B2 | 12/2019 | Corbett |
| 10,512,538 | B2 | 12/2019 | Alkhatib |
| 10,517,726 | B2 | 12/2019 | Chau |
| 10,524,902 | B2 | 1/2020 | Gründeman |
| 10,524,910 | B2 | 1/2020 | Hammer |
| 10,531,951 | B2 | 1/2020 | Spargias |
| 10,537,427 | B2 | 1/2020 | Zeng |
| 10,555,809 | B2 | 2/2020 | Hastings |
| 10,555,812 | B2 | 2/2020 | Duffy |
| 10,561,495 | B2 | 2/2020 | Chambers |
| 10,595,992 | B2 | 3/2020 | Chambers |
| 10,610,362 | B2 | 4/2020 | Quadri |
| 10,653,523 | B2 | 5/2020 | Chambers |
| 10,667,905 | B2 | 6/2020 | Ekvall |
| 10,667,909 | B2 | 6/2020 | Richter |
| 10,702,379 | B2 | 7/2020 | Garde |
| 10,702,380 | B2 | 7/2020 | Morriss |
| 10,709,560 | B2 | 7/2020 | Kofidis |
| 10,751,169 | B2 | 8/2020 | Chambers |
| 10,751,170 | B2 | 8/2020 | Richter |
| 10,751,172 | B2 | 8/2020 | Para |
| 10,758,265 | B2 | 9/2020 | Siegel |
| 10,758,342 | B2 | 9/2020 | Chau |
| 10,779,935 | B2 | 9/2020 | Scorsin |
| 10,779,936 | B2 | 9/2020 | Pollak |
| 10,779,968 | B2 | 9/2020 | Giasolli |
| 10,786,351 | B2 | 9/2020 | Christianson |
| 10,828,152 | B2 | 11/2020 | Chambers |
| 10,856,983 | B2 | 12/2020 | Keränen |
| 10,869,756 | B2 | 12/2020 | Al-Jilaihawi |
| 10,874,513 | B2 | 12/2020 | Chambers |
| 10,945,835 | B2 | 3/2021 | Morriss |
| 10,973,630 | B2 | 4/2021 | Torrianni |
| 10,980,636 | B2 | 4/2021 | Delaloye |
| 11,000,000 | B2 | 5/2021 | Mason |
| 11,007,053 | B2 | 5/2021 | Braido |
| 11,007,054 | B2 | 5/2021 | Braido |
| 11,013,599 | B2 | 5/2021 | Subramanian |
| 11,026,782 | B2 | 6/2021 | Chambers |
| 11,033,275 | B2 | 6/2021 | Franano et al. |
| 11,045,202 | B2 | 6/2021 | Amplatz |
| 11,065,113 | B2 | 7/2021 | Backus |
| 11,065,116 | B2 | 7/2021 | Tegels |
| 11,065,138 | B2 | 7/2021 | Schreck |
| 11,096,781 | B2 | 8/2021 | Gurovich |

(56) References Cited

U.S. PATENT DOCUMENTS

| | | | |
|---|---|---|---|
| 11,147,666 | B2 | 10/2021 | Braido |
| 11,154,239 | B2 | 10/2021 | Toth |
| 11,154,396 | B2 | 10/2021 | Dibie |
| 11,154,398 | B2 | 10/2021 | Straubinger |
| 11,197,754 | B2 | 12/2021 | Saffari |
| 11,207,176 | B2 | 12/2021 | Delaloye |
| 11,278,399 | B2 | 3/2022 | Liu |
| 11,278,406 | B2 | 3/2022 | Straubinger |
| 11,318,013 | B2 | 5/2022 | Mcveigh et al. |
| 11,351,028 | B2 | 6/2022 | Peterson |
| 11,389,293 | B2 | 7/2022 | Torrianni |
| 11,395,734 | B2 | 7/2022 | Lee |
| 11,413,141 | B2 | 8/2022 | Morin |
| 11,419,716 | B2 | 8/2022 | Braido |
| 11,452,628 | B2 | 9/2022 | Diedering |
| 11,458,013 | B2 | 10/2022 | Righini |
| 12,364,598 | B2 | 7/2025 | Maimon et al. |
| 2001/0005787 | A1 | 6/2001 | Oz |
| 2002/0072710 | A1 | 6/2002 | Stewart |
| 2002/0161377 | A1 | 10/2002 | Rabkin |
| 2003/0057156 | A1 | 3/2003 | Peterson |
| 2003/0083730 | A1 | 5/2003 | Stinson |
| 2003/0199971 | A1 | 10/2003 | Tower |
| 2003/0225445 | A1 | 12/2003 | Derus |
| 2003/0233141 | A1 | 12/2003 | Israel |
| 2004/0073286 | A1 | 4/2004 | Armstrong |
| 2004/0088041 | A1 | 5/2004 | Stanford |
| 2004/0138745 | A1 | 7/2004 | Macoviak |
| 2004/0210307 | A1 | 10/2004 | Khairkhahan |
| 2004/0243107 | A1 | 12/2004 | Macoviak |
| 2005/0004641 | A1 | 1/2005 | Pappu |
| 2005/0075727 | A1 | 4/2005 | Wheatley |
| 2005/0096739 | A1 | 5/2005 | Cao |
| 2005/0113861 | A1 | 5/2005 | Corcoran |
| 2005/0137622 | A1 | 6/2005 | Griffin |
| 2005/0197694 | A1 | 9/2005 | Pai |
| 2005/0273160 | A1 | 12/2005 | Lashinski |
| 2006/0142847 | A1 | 6/2006 | Shaknovich |
| 2006/0184226 | A1 | 8/2006 | Austin |
| 2006/0224183 | A1 | 10/2006 | Freudenthal |
| 2006/0229708 | A1 | 10/2006 | Powell |
| 2006/0259134 | A1 | 11/2006 | Schwammenthal et al. |
| 2006/0271173 | A1 | 11/2006 | Delgado |
| 2006/0276874 | A1 | 12/2006 | Wilson |
| 2007/0016288 | A1 | 1/2007 | Gurskis |
| 2007/0173930 | A1 | 7/2007 | Sogard |
| 2007/0233223 | A1 | 10/2007 | Styrc |
| 2007/0238979 | A1 | 10/2007 | Huynh |
| 2007/0239254 | A1 | 10/2007 | Chia |
| 2007/0239271 | A1 | 10/2007 | Nguyen |
| 2007/0270931 | A1 | 11/2007 | Leanna |
| 2007/0275027 | A1 | 11/2007 | Wen et al. |
| 2007/0293942 | A1 | 12/2007 | Mirzaee |
| 2008/0004697 | A1 | 1/2008 | Lichtenstein |
| 2008/0039928 | A1 | 2/2008 | Peacock |
| 2008/0082166 | A1 | 4/2008 | Styrc |
| 2008/0262592 | A1 | 10/2008 | Jordan |
| 2008/0269877 | A1 | 10/2008 | Jenson |
| 2008/0275540 | A1 | 11/2008 | Wen |
| 2008/0281398 | A1 | 11/2008 | Koss |
| 2008/0288042 | A1 | 11/2008 | Purdy |
| 2008/0288055 | A1 | 11/2008 | Paul, Jr. |
| 2009/0076585 | A1 | 3/2009 | Hendriksen |
| 2009/0082840 | A1 | 3/2009 | Rusk |
| 2009/0099640 | A1 | 4/2009 | Weng |
| 2009/0099647 | A1 | 4/2009 | Glimsdale |
| 2009/0125096 | A1 | 5/2009 | Chu |
| 2009/0143852 | A1 | 6/2009 | Chambers |
| 2009/0171447 | A1 | 7/2009 | Von Segesser |
| 2009/0171456 | A1 | 7/2009 | Kveen |
| 2009/0198315 | A1 | 8/2009 | Boudjemline |
| 2009/0248134 | A1 | 10/2009 | Dierking |
| 2009/0248143 | A1 | 10/2009 | Laham |
| 2009/0270967 | A1 | 10/2009 | Fleming, III |
| 2009/0276039 | A1 | 11/2009 | Meretei |
| 2009/0281609 | A1 | 11/2009 | Benichou |
| 2010/0057192 | A1 | 3/2010 | Celermajer |
| 2010/0069948 | A1 | 3/2010 | Veznedaroglu |
| 2010/0168839 | A1 | 7/2010 | Braido |
| 2010/0174355 | A1 | 7/2010 | Boyle |
| 2010/0217261 | A1 | 8/2010 | Watson |
| 2010/0217262 | A1 | 8/2010 | Stevenson |
| 2010/0217382 | A1 | 8/2010 | Chau |
| 2010/0256749 | A1 | 10/2010 | Tran |
| 2010/0262157 | A1 | 10/2010 | Silver |
| 2010/0262231 | A1 | 10/2010 | Tuval et al. |
| 2011/0022151 | A1 | 1/2011 | Shin |
| 2011/0046712 | A1 | 2/2011 | Melsheimer |
| 2011/0082539 | A1 | 4/2011 | Suri |
| 2011/0082540 | A1 | 4/2011 | Forster |
| 2011/0208293 | A1 | 8/2011 | Tabor |
| 2011/0218585 | A1 | 9/2011 | Krinke et al. |
| 2011/0251676 | A1 | 10/2011 | Sweeney |
| 2011/0301702 | A1 | 12/2011 | Rust |
| 2011/0319988 | A1 | 12/2011 | Schankereli |
| 2011/0319991 | A1 | 12/2011 | Hariton |
| 2012/0016468 | A1 | 1/2012 | Robin |
| 2012/0035719 | A1 | 2/2012 | Forster |
| 2012/0078356 | A1 | 3/2012 | Fish |
| 2012/0083875 | A1 | 4/2012 | Johnson |
| 2012/0095551 | A1 | 4/2012 | Navia |
| 2012/0101567 | A1 | 4/2012 | Jansen |
| 2012/0101571 | A1 | 4/2012 | Thambar |
| 2012/0109079 | A1 | 5/2012 | Asleson |
| 2012/0197193 | A1 | 8/2012 | Krolik et al. |
| 2012/0197390 | A1 | 8/2012 | Alkhatib |
| 2012/0209375 | A1 | 8/2012 | Madrid |
| 2012/0226130 | A1 | 9/2012 | De Graff |
| 2012/0303048 | A1 | 11/2012 | Manasse |
| 2012/0323313 | A1 | 12/2012 | Seguin |
| 2013/0023852 | A1 | 1/2013 | Drasler |
| 2013/0060329 | A1 | 3/2013 | Agnew |
| 2013/0066419 | A1 | 3/2013 | Gregg |
| 2013/0079872 | A1 | 3/2013 | Gallagher |
| 2013/0090728 | A1 | 4/2013 | Solem |
| 2013/0096671 | A1 | 4/2013 | Iobbi |
| 2013/0123911 | A1 | 5/2013 | Chalekian |
| 2013/0138138 | A1 | 5/2013 | Clark |
| 2013/0150956 | A1 | 6/2013 | Yohanan |
| 2013/0178783 | A1 | 7/2013 | McNamara et al. |
| 2013/0184811 | A1 | 7/2013 | Rowe |
| 2013/0190861 | A1 | 7/2013 | Chau |
| 2013/0204311 | A1 | 8/2013 | Kunis |
| 2013/0204360 | A1 | 8/2013 | Gainor |
| 2013/0226286 | A1 | 8/2013 | Hargreaves |
| 2013/0231735 | A1 | 9/2013 | Deem et al. |
| 2013/0231736 | A1 | 9/2013 | Essinger |
| 2013/0238089 | A1 | 9/2013 | Lichtenstein |
| 2013/0274855 | A1 | 10/2013 | Stante |
| 2013/0297010 | A1 | 11/2013 | Bishop |
| 2013/0297012 | A1 | 11/2013 | Willard |
| 2013/0304197 | A1 | 11/2013 | Buchbinder |
| 2013/0310917 | A1 | 11/2013 | Richter |
| 2013/0310923 | A1 | 11/2013 | Kheradvar |
| 2013/0317598 | A1 | 11/2013 | Rowe |
| 2013/0331933 | A1 | 12/2013 | Alkhatib |
| 2014/0005768 | A1 | 1/2014 | Thomas |
| 2014/0005773 | A1 | 1/2014 | Wheatley |
| 2014/0005778 | A1 | 1/2014 | Buchbinder |
| 2014/0012371 | A1 | 1/2014 | Li |
| 2014/0018841 | A1 | 1/2014 | Peiffer |
| 2014/0018906 | A1 | 1/2014 | Rafiee |
| 2014/0031928 | A1 | 1/2014 | Murphy |
| 2014/0031951 | A1 | 1/2014 | Costello |
| 2014/0039613 | A1 | 2/2014 | Navia |
| 2014/0046433 | A1 | 2/2014 | Kovalsky |
| 2014/0046436 | A1 | 2/2014 | Kheradvar |
| 2014/0052238 | A1 | 2/2014 | Wang |
| 2014/0052241 | A1 | 2/2014 | Harks |
| 2014/0067050 | A1 | 3/2014 | Costello |
| 2014/0074151 | A1 | 3/2014 | Tischler |
| 2014/0081308 | A1 | 3/2014 | Wondka |
| 2014/0081375 | A1 | 3/2014 | Bardill et al. |
| 2014/0088696 | A1 | 3/2014 | Figulla |

(56) References Cited

U.S. PATENT DOCUMENTS

| | | | |
|---|---|---|---|
| 2014/0114340 | A1 | 4/2014 | Zhou |
| 2014/0128963 | A1 | 5/2014 | Quill |
| 2014/0134322 | A1 | 5/2014 | Larsen |
| 2014/0135817 | A1 | 5/2014 | Tischler |
| 2014/0135907 | A1 | 5/2014 | Gallagher |
| 2014/0142612 | A1 | 5/2014 | Li |
| 2014/0142680 | A1 | 5/2014 | Laske |
| 2014/0142688 | A1 | 5/2014 | Duffy |
| 2014/0142691 | A1 | 5/2014 | Pouletty |
| 2014/0163668 | A1 | 6/2014 | Rafiee |
| 2014/0172076 | A1 | 6/2014 | Jonsson |
| 2014/0172083 | A1 | 6/2014 | Bruchman |
| 2014/0180397 | A1 | 6/2014 | Gerberding |
| 2014/0180401 | A1 | 6/2014 | Quill |
| 2014/0188157 | A1 | 7/2014 | Clark |
| 2014/0194979 | A1 | 7/2014 | Seguin |
| 2014/0222140 | A1 | 8/2014 | Schreck |
| 2014/0228944 | A1 | 8/2014 | Paniagua |
| 2014/0236288 | A1 | 8/2014 | Lambrecht |
| 2014/0243954 | A1 | 8/2014 | Shannon |
| 2014/0243967 | A1 | 8/2014 | Salahieh |
| 2014/0243969 | A1 | 8/2014 | Venkatasubramani |
| 2014/0249564 | A1 | 9/2014 | Daly |
| 2014/0249621 | A1 | 9/2014 | Eidenschink |
| 2014/0257467 | A1 | 9/2014 | Lane |
| 2014/0276395 | A1 | 9/2014 | Wilson |
| 2014/0277074 | A1 | 9/2014 | Kaplan |
| 2014/0277119 | A1 | 9/2014 | Akpinar |
| 2014/0277388 | A1 | 9/2014 | Skemp |
| 2014/0277389 | A1 | 9/2014 | Braido |
| 2014/0277408 | A1 | 9/2014 | Folan |
| 2014/0277411 | A1 | 9/2014 | Börtlein |
| 2014/0277417 | A1 | 9/2014 | Schraut |
| 2014/0277422 | A1 | 9/2014 | Ratz |
| 2014/0277424 | A1 | 9/2014 | Oslund |
| 2014/0277425 | A1 | 9/2014 | Dakin |
| 2014/0277426 | A1 | 9/2014 | Dakin |
| 2014/0277573 | A1 | 9/2014 | Gill et al. |
| 2014/0288634 | A1 | 9/2014 | Shalev |
| 2014/0288639 | A1 | 9/2014 | Gainor |
| 2014/0296909 | A1 | 10/2014 | Heipl |
| 2014/0296969 | A1 | 10/2014 | Tegels |
| 2014/0296970 | A1 | 10/2014 | Ekvall |
| 2014/0296975 | A1 | 10/2014 | Tegels |
| 2014/0309727 | A1 | 10/2014 | Lamelas |
| 2014/0330366 | A1 | 11/2014 | Dehdashtian |
| 2014/0330368 | A1 | 11/2014 | Gloss |
| 2014/0330369 | A1 | 11/2014 | Matheny |
| 2014/0330370 | A1 | 11/2014 | Matheny |
| 2014/0331475 | A1 | 11/2014 | Duffy |
| 2014/0343665 | A1 | 11/2014 | Straubinger |
| 2014/0343669 | A1 | 11/2014 | Lane |
| 2014/0343670 | A1 | 11/2014 | Bakis |
| 2014/0358224 | A1 | 12/2014 | Tegels |
| 2014/0371844 | A1 | 12/2014 | Dale |
| 2014/0379020 | A1 | 12/2014 | Campbell |
| 2015/0005857 | A1 | 1/2015 | Kern |
| 2015/0018933 | A1 | 1/2015 | Yang |
| 2015/0025621 | A1 | 1/2015 | Costello |
| 2015/0025625 | A1 | 1/2015 | Rylski |
| 2015/0039081 | A1 | 2/2015 | Costello |
| 2015/0039083 | A1 | 2/2015 | Rafiee |
| 2015/0066138 | A1 | 3/2015 | Alexander |
| 2015/0066141 | A1 | 3/2015 | Braido |
| 2015/0073548 | A1 | 3/2015 | Matheny |
| 2015/0088248 | A1 | 3/2015 | Scorsin |
| 2015/0088251 | A1 | 3/2015 | May-Newman |
| 2015/0094802 | A1 | 4/2015 | Buchbinder |
| 2015/0094804 | A1 | 4/2015 | Bonhoeffer |
| 2015/0112428 | A1 | 4/2015 | Daly |
| 2015/0112430 | A1 | 4/2015 | Creaven |
| 2015/0119974 | A1 | 4/2015 | Rothstein |
| 2015/0119978 | A1 | 4/2015 | Tegels |
| 2015/0119980 | A1 | 4/2015 | Beith |
| 2015/0119982 | A1 | 4/2015 | Quill |
| 2015/0127032 | A1 | 5/2015 | Lentz |
| 2015/0127093 | A1 | 5/2015 | Hosmer |
| 2015/0127097 | A1 | 5/2015 | Neumann |
| 2015/0127100 | A1 | 5/2015 | Braido |
| 2015/0134054 | A1 | 5/2015 | Morrissey |
| 2015/0142103 | A1 | 5/2015 | Vidlund |
| 2015/0142104 | A1 | 5/2015 | Braido |
| 2015/0148731 | A1 | 5/2015 | Mcnamara |
| 2015/0150678 | A1 | 6/2015 | Brecker |
| 2015/0157455 | A1 | 6/2015 | Hoang |
| 2015/0157458 | A1 | 6/2015 | Thambar |
| 2015/0173770 | A1 | 6/2015 | Warner |
| 2015/0173897 | A1 | 6/2015 | Raanani |
| 2015/0173898 | A1 | 6/2015 | Drasler |
| 2015/0173899 | A1 | 6/2015 | Braido |
| 2015/0196300 | A1 | 7/2015 | Tischler |
| 2015/0196390 | A1 | 7/2015 | Ma |
| 2015/0196393 | A1 | 7/2015 | Vidlund |
| 2015/0209140 | A1 | 7/2015 | Bell |
| 2015/0209143 | A1 | 7/2015 | Duffy |
| 2015/0223729 | A1 | 8/2015 | Balachandran |
| 2015/0223820 | A1 | 8/2015 | Olson |
| 2015/0223934 | A1 | 8/2015 | Mdlund |
| 2015/0230919 | A1 | 8/2015 | Chau et al. |
| 2015/0230921 | A1 | 8/2015 | Chau |
| 2015/0238312 | A1 | 8/2015 | Lashinski |
| 2015/0238313 | A1 | 8/2015 | Spence |
| 2015/0257879 | A1 | 9/2015 | Bortlein |
| 2015/0257880 | A1 | 9/2015 | Bortlein |
| 2015/0257881 | A1 | 9/2015 | Bortlein |
| 2015/0257882 | A1 | 9/2015 | Bortlein |
| 2015/0265402 | A1 | 9/2015 | Centola |
| 2015/0265404 | A1 | 9/2015 | Rankin |
| 2015/0272730 | A1 | 10/2015 | Melnick |
| 2015/0272731 | A1 | 10/2015 | Racchini |
| 2015/0272738 | A1 | 10/2015 | Sievers |
| 2015/0282931 | A1 | 10/2015 | Brunnett |
| 2015/0282958 | A1 | 10/2015 | Centola |
| 2015/0289972 | A1 | 10/2015 | Yang |
| 2015/0289974 | A1 | 10/2015 | Matheny |
| 2015/0289977 | A1 | 10/2015 | Kovalsky |
| 2015/0290007 | A1 | 10/2015 | Aggerholm |
| 2015/0297346 | A1 | 10/2015 | Duffy |
| 2015/0297381 | A1 | 10/2015 | Essinger |
| 2015/0305860 | A1 | 10/2015 | Wang |
| 2015/0305861 | A1 | 10/2015 | Annest |
| 2015/0313710 | A1 | 11/2015 | Eberhardt |
| 2015/0313712 | A1 | 11/2015 | Carpentier |
| 2015/0320552 | A1 | 11/2015 | Letac |
| 2015/0320556 | A1 | 11/2015 | Levi |
| 2015/0327995 | A1 | 11/2015 | Morin |
| 2015/0327996 | A1 | 11/2015 | Fahim |
| 2015/0327999 | A1 | 11/2015 | Board |
| 2015/0328000 | A1 | 11/2015 | Ratz et al. |
| 2015/0335422 | A1 | 11/2015 | Straka |
| 2015/0342718 | A1 | 12/2015 | Weber |
| 2015/0342734 | A1 | 12/2015 | Braido |
| 2015/0351735 | A1 | 12/2015 | Keranen |
| 2015/0351904 | A1 | 12/2015 | Cooper |
| 2015/0351905 | A1 | 12/2015 | Benson |
| 2015/0359628 | A1 | 12/2015 | Keranen |
| 2015/0359629 | A1 | 12/2015 | Ganesan |
| 2015/0366665 | A1 | 12/2015 | Lombardi |
| 2015/0366667 | A1 | 12/2015 | Bailey |
| 2015/0366690 | A1 | 12/2015 | Lumauig |
| 2015/0374490 | A1 | 12/2015 | Alkhatib |
| 2015/0374906 | A1 | 12/2015 | Forsell |
| 2016/0000559 | A1 | 1/2016 | Chen |
| 2016/0000562 | A1 | 1/2016 | Siegel |
| 2016/0008128 | A1 | 1/2016 | Squara |
| 2016/0008131 | A1 | 1/2016 | Christianson |
| 2016/0015512 | A1 | 1/2016 | Zhang |
| 2016/0015515 | A1 | 1/2016 | Lashinski |
| 2016/0022417 | A1 | 1/2016 | Karapetian |
| 2016/0022418 | A1 | 1/2016 | Salahieh |
| 2016/0030165 | A1 | 2/2016 | Mitra |
| 2016/0030168 | A1 | 2/2016 | Spenser |
| 2016/0030169 | A1 | 2/2016 | Shahriari |
| 2016/0030170 | A1 | 2/2016 | Alkhatib |

(56) References Cited

U.S. PATENT DOCUMENTS

| | | | |
|---|---|---|---|
| 2016/0030171 | A1 | 2/2016 | Quijano |
| 2016/0030173 | A1 | 2/2016 | Cai |
| 2016/0030175 | A1 | 2/2016 | Madjarov |
| 2016/0038283 | A1 | 2/2016 | Divekar |
| 2016/0045306 | A1 | 2/2016 | Agrawal |
| 2016/0045308 | A1 | 2/2016 | Macoviak |
| 2016/0045309 | A1 | 2/2016 | Valdez |
| 2016/0045310 | A1 | 2/2016 | Alkhatib |
| 2016/0045311 | A1 | 2/2016 | Mccann |
| 2016/0051358 | A1 | 2/2016 | Sutton |
| 2016/0051362 | A1 | 2/2016 | Cooper |
| 2016/0051364 | A1 | 2/2016 | Cunningham |
| 2016/0066922 | A1 | 3/2016 | Bridgeman |
| 2016/0067038 | A1 | 3/2016 | Park |
| 2016/0067041 | A1 | 3/2016 | Alkhatib |
| 2016/0074161 | A1 | 3/2016 | Bennett |
| 2016/0074164 | A1 | 3/2016 | Naor |
| 2016/0074165 | A1 | 3/2016 | Spence |
| 2016/0081799 | A1 | 3/2016 | Leo |
| 2016/0089234 | A1 | 3/2016 | Gifford, III |
| 2016/0089235 | A1 | 3/2016 | Yellin |
| 2016/0089236 | A1 | 3/2016 | Kovalsky |
| 2016/0095700 | A1 | 4/2016 | Righini |
| 2016/0095701 | A1 | 4/2016 | Dale |
| 2016/0095702 | A1 | 4/2016 | Gainor |
| 2016/0095703 | A1 | 4/2016 | Thomas |
| 2016/0095704 | A1 | 4/2016 | Whitman |
| 2016/0100844 | A1 | 4/2016 | Li |
| 2016/0100939 | A1 | 4/2016 | Armstrong |
| 2016/0100941 | A1 | 4/2016 | Czyscon |
| 2016/0100942 | A1 | 4/2016 | Morrissey |
| 2016/0106539 | A1 | 4/2016 | Buchbinder |
| 2016/0113764 | A1 | 4/2016 | Sheahan |
| 2016/0113766 | A1 | 4/2016 | Ganesan |
| 2016/0113767 | A1 | 4/2016 | Miller |
| 2016/0113768 | A1 | 4/2016 | Ganesan |
| 2016/0120642 | A1 | 5/2016 | Shaolian |
| 2016/0120643 | A1 | 5/2016 | Kupumbati |
| 2016/0120646 | A1 | 5/2016 | Dwork |
| 2016/0135951 | A1 | 5/2016 | Salahieh |
| 2016/0136412 | A1 | 5/2016 | Mckinnon |
| 2016/0143730 | A1 | 5/2016 | Kheradvar |
| 2016/0143731 | A1 | 5/2016 | Backus |
| 2016/0143734 | A1 | 5/2016 | Shaolian |
| 2016/0151155 | A1 | 6/2016 | Lutter |
| 2016/0157998 | A1 | 6/2016 | Bruchman |
| 2016/0157999 | A1 | 6/2016 | Lane |
| 2016/0158001 | A1 | 6/2016 | Wallace |
| 2016/0158004 | A1 | 6/2016 | Kumar |
| 2016/0158007 | A1 | 6/2016 | Centola |
| 2016/0158011 | A1 | 6/2016 | De Canniere |
| 2016/0158013 | A1 | 6/2016 | Carpentier |
| 2016/0166381 | A1 | 6/2016 | Sugimoto |
| 2016/0166382 | A1 | 6/2016 | Nguyen |
| 2016/0166384 | A1 | 6/2016 | Olson |
| 2016/0175096 | A1 | 6/2016 | Dienno |
| 2016/0193044 | A1 | 7/2016 | Achiluzzi |
| 2016/0193045 | A1 | 7/2016 | Pollak |
| 2016/0193047 | A1 | 7/2016 | Delaloye |
| 2016/0199177 | A1 | 7/2016 | Spence |
| 2016/0199178 | A1 | 7/2016 | Venkatasubramani |
| 2016/0199180 | A1 | 7/2016 | Zeng |
| 2016/0199182 | A1 | 7/2016 | Gorman, III |
| 2016/0213470 | A1 | 7/2016 | Ahlberg |
| 2016/0220363 | A1 | 8/2016 | Peter |
| 2016/0235525 | A1 | 8/2016 | Rothstein |
| 2016/0235530 | A1 | 8/2016 | Thomas |
| 2016/0235531 | A1 | 8/2016 | Ciobanu |
| 2016/0250022 | A1 | 9/2016 | Braido |
| 2016/0250051 | A1 | 9/2016 | Lim |
| 2016/0256168 | A1 | 9/2016 | Nielsen |
| 2016/0256270 | A1 | 9/2016 | Folan |
| 2016/0262884 | A1 | 9/2016 | Lombardi |
| 2016/0270910 | A1 | 9/2016 | Birmingham |
| 2016/0270911 | A1 | 9/2016 | Ganesan |
| 2016/0278922 | A1 | 9/2016 | Braido |
| 2016/0296323 | A1 | 10/2016 | Wulfman |
| 2016/0296333 | A1 | 10/2016 | Balachandran |
| 2016/0302920 | A1 | 10/2016 | Al-Jilaihawi |
| 2016/0302921 | A1 | 10/2016 | Gosal |
| 2016/0302922 | A1 | 10/2016 | Keidar |
| 2016/0310268 | A1 | 10/2016 | Oba |
| 2016/0324640 | A1 | 11/2016 | Gifford, III |
| 2016/0331529 | A1 | 11/2016 | Marchand |
| 2016/0346081 | A1 | 12/2016 | Zeng |
| 2016/0354203 | A1 | 12/2016 | Tuval et al. |
| 2016/0361161 | A1 | 12/2016 | Braido |
| 2016/0374790 | A1 | 12/2016 | Jacinto |
| 2016/0374801 | A1 | 12/2016 | Jimenez |
| 2016/0374802 | A1 | 12/2016 | Levi |
| 2016/0374803 | A1 | 12/2016 | Figulla |
| 2016/0374842 | A1 | 12/2016 | Havel |
| 2017/0079781 | A1 | 3/2017 | Lim |
| 2017/0079785 | A1 | 3/2017 | Li |
| 2017/0079787 | A1 | 3/2017 | Benson |
| 2017/0079790 | A1 | 3/2017 | Vidlund |
| 2017/0086973 | A1 | 3/2017 | Zeng |
| 2017/0095256 | A1 | 4/2017 | Lindgren |
| 2017/0100241 | A1 | 4/2017 | Modine |
| 2017/0105839 | A1 | 4/2017 | Subramanian |
| 2017/0165066 | A1 | 6/2017 | Rothstein |
| 2017/0172737 | A1 | 6/2017 | Kuetting |
| 2017/0202525 | A1 | 7/2017 | Piazza |
| 2017/0209268 | A1 | 7/2017 | Cunningham et al. |
| 2017/0231761 | A1 | 8/2017 | Cohen-Tzemach et al. |
| 2017/0252191 | A1 | 9/2017 | Pacetti |
| 2017/0281193 | A1 | 10/2017 | Asirvatham |
| 2017/0325944 | A1 | 11/2017 | Erzberger et al. |
| 2017/0333102 | A1 | 11/2017 | Peterson et al. |
| 2017/0348098 | A1 | 12/2017 | Rowe |
| 2017/0360570 | A1 | 12/2017 | Berndt et al. |
| 2018/0014830 | A1 | 1/2018 | Neumann |
| 2018/0055629 | A1 | 3/2018 | Oba et al. |
| 2018/0092744 | A1 | 4/2018 | Von Oepen |
| 2018/0104077 | A1* | 4/2018 | Cartledge ................ A61F 2/93 |
| 2018/0116843 | A1 | 5/2018 | Schreck |
| 2018/0116848 | A1 | 5/2018 | Mchugo |
| 2018/0133012 | A1 | 5/2018 | Nathe |
| 2018/0185184 | A1 | 7/2018 | Christakis |
| 2018/0193153 | A1 | 7/2018 | Brenzel et al. |
| 2018/0206983 | A1 | 7/2018 | Noe |
| 2018/0228606 | A1 | 8/2018 | Alon |
| 2018/0256329 | A1 | 9/2018 | Chambers |
| 2018/0296335 | A1 | 10/2018 | Miyashiro |
| 2018/0311039 | A1 | 11/2018 | Cohen |
| 2018/0325664 | A1 | 11/2018 | Gonda |
| 2018/0360602 | A1 | 12/2018 | Kumar |
| 2018/0369006 | A1 | 12/2018 | Zhang |
| 2019/0053898 | A1 | 2/2019 | Maimon et al. |
| 2019/0099265 | A1 | 4/2019 | Braido |
| 2019/0105088 | A1 | 4/2019 | Peterson et al. |
| 2019/0151067 | A1 | 5/2019 | Zucker |
| 2019/0201192 | A1 | 7/2019 | Kruse |
| 2019/0224028 | A1 | 7/2019 | Finn |
| 2019/0247189 | A1 | 8/2019 | Dale |
| 2019/0247190 | A1 | 8/2019 | Nathe |
| 2019/0321530 | A1 | 10/2019 | Cambronne |
| 2019/0321531 | A1 | 10/2019 | Cambronne |
| 2019/0365534 | A1 | 12/2019 | Kramer |
| 2019/0365538 | A1 | 12/2019 | Chambers |
| 2020/0000592 | A1 | 1/2020 | Lee |
| 2020/0030088 | A1 | 1/2020 | Mdlund |
| 2020/0030507 | A1 | 1/2020 | Higgins |
| 2020/0069423 | A1 | 3/2020 | Peterson |
| 2020/0069449 | A1 | 3/2020 | Diedering |
| 2020/0100897 | A1 | 4/2020 | Mclean |
| 2020/0113682 | A1 | 4/2020 | Chang |
| 2020/0113719 | A1 | 4/2020 | Desrosiers et al. |
| 2020/0129294 | A1 | 4/2020 | Hariton |
| 2020/0155306 | A1 | 5/2020 | Bonyuet |
| 2020/0163765 | A1 | 5/2020 | Christianson |
| 2020/0179111 | A1 | 6/2020 | Mdlund |
| 2020/0179115 | A1 | 6/2020 | Chambers |
| 2020/0188101 | A1 | 6/2020 | Chambers |

(56) References Cited

U.S. PATENT DOCUMENTS

| | | | |
|---|---|---|---|
| 2020/0222179 | A1 | 7/2020 | Chambers |
| 2020/0253733 | A1 | 8/2020 | Subramanian |
| 2020/0261219 | A1 | 8/2020 | Kumar |
| 2020/0276013 | A1 | 9/2020 | Chambers |
| 2020/0315678 | A1 | 10/2020 | Mazzio et al. |
| 2020/0337765 | A1 | 10/2020 | Smith |
| 2020/0368023 | A1 | 11/2020 | Kheradvar |
| 2020/0375733 | A1 | 12/2020 | Diedering |
| 2021/0236274 | A1 | 8/2021 | Benson |
| 2021/0236276 | A1 | 8/2021 | Diedering |
| 2021/0275297 | A1 | 9/2021 | Berndt |
| 2021/0275301 | A1 | 9/2021 | Kumar |
| 2021/0290383 | A1 | 9/2021 | Chambers |
| 2022/0031451 | A1 | 2/2022 | Spence |
| 2022/0273433 | A1 | 9/2022 | Kuck et al. |
| 2022/0338979 | A1 | 10/2022 | Benichou |
| 2023/0218397 | A1 | 7/2023 | Chambers et al. |
| 2023/0372089 | A1 | 11/2023 | Kumar |
| 2024/0058124 | A1 | 2/2024 | Montgomery et al. |
| 2024/0138976 | A1 | 5/2024 | Berndt et al. |
| 2024/0341952 | A1 | 10/2024 | Kruse et al. |
| 2024/0366366 | A1 | 11/2024 | Diedering et al. |
| 2025/0049564 | A1 | 2/2025 | Berndt et al. |
| 2025/0057652 | A1 | 2/2025 | Kumar et al. |
| 2025/0248805 | A1 | 8/2025 | Diedering et al. |
| 2025/0248812 | A1 | 8/2025 | Diedering et al. |
| 2025/0255740 | A1 | 8/2025 | Diedering et al. |
| 2025/0288414 | A1 | 9/2025 | Diedering |

FOREIGN PATENT DOCUMENTS

| | | | |
|---|---|---|---|
| AU | 2013201970 | B2 | 3/2016 |
| CN | 2820130 | Y | 9/2006 |
| CN | 100413471 | C | 8/2008 |
| CN | 100444811 | C | 12/2008 |
| CN | 101953723 | A | 1/2011 |
| CN | 101953724 | A | 1/2011 |
| CN | 101953725 | A | 1/2011 |
| CN | 101953728 | A | 1/2011 |
| CN | 101953729 | A | 1/2011 |
| CN | 101961269 | A | 2/2011 |
| CN | 101961273 | A | 2/2011 |
| CN | 102036622 | A | 4/2011 |
| CN | 201870772 | U | 6/2011 |
| CN | 203290964 | U | 11/2013 |
| CN | 103431931 | A | 12/2013 |
| CN | 203379235 | U | 1/2014 |
| CN | 103598939 | A | 2/2014 |
| CN | 103610520 | A | 3/2014 |
| CN | 203619728 | U | 6/2014 |
| CN | 203677318 | U | 7/2014 |
| CN | 104287804 | A | 1/2015 |
| CN | 104352261 | A | 2/2015 |
| CN | 204133530 | U | 2/2015 |
| CN | 204181679 | U | 3/2015 |
| CN | 204246182 | U | 4/2015 |
| CN | 204318826 | U | 5/2015 |
| CN | 104688292 | A | 6/2015 |
| CN | 102985033 | B | 8/2015 |
| CN | 204581598 | U | 8/2015 |
| CN | 204581599 | U | 8/2015 |
| CN | 204683686 | U | 10/2015 |
| CN | 105596052 | A | 5/2016 |
| CN | 105615936 | A | 6/2016 |
| CN | 205286438 | U | 6/2016 |
| CN | 108348270 | A | 7/2018 |
| CN | 109789293 | | 5/2019 |
| CN | 107252363 | B | 4/2020 |
| CN | 106913909 | B | 9/2020 |
| CN | 107007887 | B | 10/2020 |
| DE | 102010021345 | A1 | 11/2011 |
| EP | 2596754 | A1 | 5/2013 |
| EP | 2967858 | A2 | 1/2016 |
| EP | 2982336 | A1 | 2/2016 |
| EP | 2967845 | B1 | 8/2018 |
| EP | 2950752 | B1 | 7/2022 |
| JP | 2016531722 | A | 10/2016 |
| WO | WO1995016476 | A1 | 6/1995 |
| WO | 1996/030060 | | 10/1996 |
| WO | WO2009127973 | A2 | 10/2009 |
| WO | WO2014210299 | A1 | 12/2014 |
| WO | WO2015004173 | A1 | 1/2015 |
| WO | WO2016100806 | A1 | 6/2016 |
| WO | WO2019006387 | | 1/2019 |

OTHER PUBLICATIONS

Reed Miller, Start-Up Spotlight: 4C Addresses Mitral Regurgitation with Unique 'Dome' Device, https://medtech.citeline.com/MT105076/StartUp-Spotlight-4C-Addresses-Mitral-Regurgitation-With-Unique-Dome-Device Published by Citeline on Jun. 29, 2017.

A Novel Transcatheter Mitral Valve Replacement System, Dr. Phillippe Genereux, MD, Jun. 14, 2017.

The AltaValve™. Attributes, Challenges, and Future Programs, Dr. Philippe Genereux, MD, Jun. 22, 2018.

4C Medical's AltaValve: The First-in-Human Experience, Joep Rodes-Cabau, MD, Sep. 21, 2018.

Ferreira-Neto et al., "Transcatheter Mitral Valve Replacement With a New Supra-Annular Valve-First-in-Human Experience with the AltaValve System," https://doi.org/10.1016/j.jcin.2018.10.056, by The American College of Cardiology Foundation Published by Elsevier, Jan. 28, 2019.

Goel et al., "Transcatheter Mitral Valve Therapy with Novel Supra-Annular AltaValve," https://doi.org/10.1016/j.jaccas.2019.10.034, Published by Elsevier on behalf of The American College of Cardiology Foundation, Dec. 18, 2019.

Hatamifar et al., "MRI Evaluation of an Atrial-Anchored Transcatheter Mitral Valve Replacement Implant," https://www.aironline.org/doi/10.2214/AJR.19.22206 American Roentgen Ray Society, Jan. 15, 2020.

Alperi et al., "Device profile of the AltaValve System for Transcatheter Mitral Valve Replacement: Overview of its safety and Efficacy," https://doi.org/10.1080/17434440.2020.1781616, Informa UK Limited, Jun. 25, 2020.

Kumar et al., "AltaValve™—A Transcatheter Mitral Valve Regurgitation Treatment Technology," Transcatheter Mitral Valve Therapy, First Edition, John Wiley & Sons Ltd., Mar. 9, 2021.

The AltaValve Supra-Annular TS System: Device Description and Early Clinical Results, Dr. Vlasis Ninios, Jun. 10, 2022.

Transcatheter Transseptal Treatment of Patients with Severe Mitral Regurgitation using an Atrial Fixation Mitral Valve Replacement Technology, Dr. Vlasis Ninios et al., Jun. 15, 2023.

Hatamifar et al., "MRI Evaluation of an Atrial-Anchored Transcatheter Mitral Valve Replacement Implant," https://www.ajronline.org/doi/10.2214/AJR.19.22206 American Roentgen Ray Society, Jan. 15, 2020.

U.S. Restriction Requirement received in U.S. Appl. No. 19/185,761, filed Jun. 16, 2025.

U.S. Office Action in U.S. Appl. No. 19/186,940, filed Sep. 8, 2025.

U.S. Appl. No. 62/854,584, filed May 30, 2019, Diedering et al.

* cited by examiner

IMPLANT DELIVERY

CROSS-REFERENCE TO RELATED APPLICATIONS

This application is a continuation of U.S. patent application Ser. No. 18/615,450, filed on Mar. 25, 2024, which is a nonprovisional of U.S. Provisional Application No. 63/454,350, filed Mar. 24, 2023, and is a nonprovisional of U.S. Provisional Application No. 63/532,489, filed Aug. 14, 2023, all of which are hereby incorporated herein by reference in their entirety.

BACKGROUND

The native heart valves, e.g., aortic, pulmonary, tricuspid and mitral valves, provide forward-only flow of an adequate supply of blood through the cardiovascular system. Native heart valves may lose functionality over time. Early interventions repaired or displaced dysfunctional valve(s) with the use of open-heart surgery. More recently, gaining access to the valve of interest has been achieved percutaneously via one of at least the following known access routes: transapical, transjugular, transfemoral; transatrial; and transseptal delivery techniques, collectively known as transcatheter techniques.

Typically, in a transcatheter technique, a prosthetic valve is mounted within a stented frame that is capable of achieving collapsed and expanded states. The frame is collapsed and advanced through a sheath or delivery catheter positioned in a blood vessel of the patient until reaching the delivery site. The stented frame is generally released from the catheter or sheath and, by a variety of means, expanded with the valve to a functional size and positioned in the heart in a functional orientation.

It therefore would be desirable to provide apparatus and methods for one or more of engaging, loading, translating, delivering, repositioning, resheathing and deploying an expandable stent to, and within, a heart chamber.

DESCRIPTION

Figure 1:
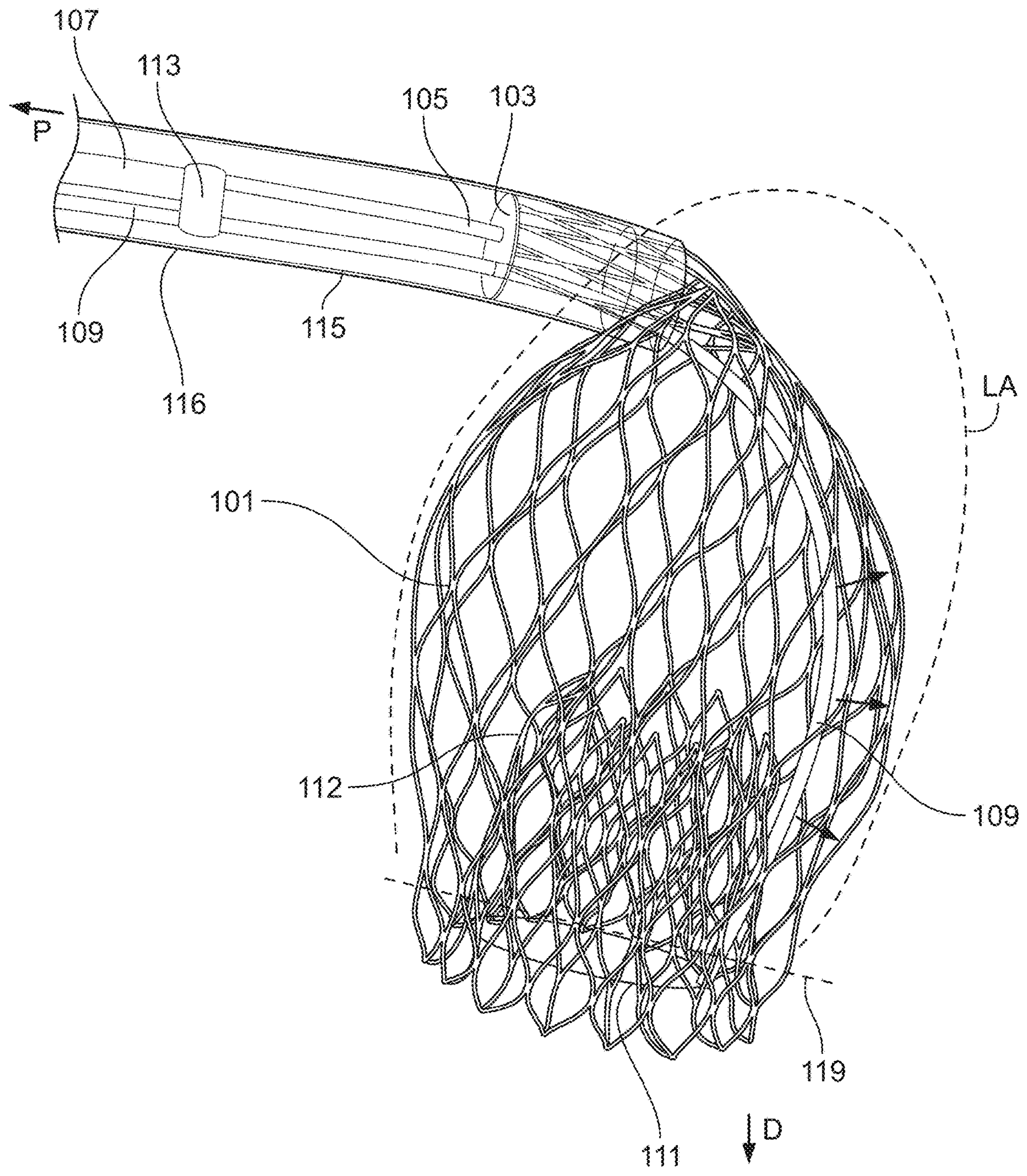
FIG. 1 shows illustrative apparatus and methods in accordance with principles of the invention.

Apparatus and methods for delivering an implant to a body cavity are provided. An implant for implanting in a body cavity may be provided. The body cavity may be a heart chamber, such as a left atrium, a right atrium, a left ventricle, or a right ventricle. The body cavity may be any other suitable location in the human body.

The implant may include one or more of the apparatus and methods described in one or more of U.S. Patent Application Publication No. 2019/0201192, filed on Dec. 31, 2018, U.S. Patent Application Publication No. 2021/0275297, filed on Dec. 4, 2020, and U.S. Patent Application Publication No. 2023/0372089, filed on May 23, 2023, all of which are hereby incorporated by reference herein in their entireties.

The methods may include one or more of the apparatus and methods described in one or more of U.S. Patent Application Publication No. 2019/0201192, filed on Dec. 31, 2018, U.S. Patent Application Publication No. 2021/0275297, filed on Dec. 4, 2020, and U.S. Patent Application Publication No. 2020/0375733, filed on May 19, 2020, all of which are hereby incorporated by reference herein in their entireties.

When the body cavity is a heart chamber, the apparatus and methods may include an implant for implanting in the heart chamber on a side of a heart to replace a valve. The heart chamber may include an annulus at a bottom of the heart chamber. The annulus may define an upper annular surface. The upper annular surface may include a perimeter of the annulus. The implant may include a curved portion for being seated in the heart chamber.

The implant may include an annular ring extending away from the curved portion. When the implant is implanted in the heart chamber, the annular ring may be positioned such that it extends through the annulus and replaces the valve.

The heart chamber may be a right atrium. The side of the heart may be a right side of the heart. The annulus may be a tricuspid valve annulus. The valve may be a tricuspid valve.

The heart chamber may be a left atrium. The side of the heart may be a left side of the heart. The annulus may be a mitral valve annulus. The valve may be a mitral valve.

The implant may include superelastic materials including one or more of nickel and titanium ("Nitinol"), NiTiCu, titanium alloys, nickel alloys, spring steel alloys, carbon fiber composites, carbon-graphene, shape-memory polymers, polyisoprene-based polymers, calcium iron arsenide $CaFe_2As_2$, stainless steel, titanium and similar materials. The implant may be collapsible. The implant may be self-expandable. The implant may expand in response to a force from an instrument.

The implant may include an outer section. The outer section may include the curved portion. The curved portion may be configured to be positioned in the heart chamber.

The outer section may include the annular ring extending away from the curved portion. The annular ring may be sized for being positioned in an annulus at a bottom of the heart chamber.

The implant may include an inner valve support positioned inside the outer section. The inner valve support may be configured to support leaflets. A transition section may extend between the inner valve support and the annular ring. The transition section may support the inner valve support within the outer section.

The outer section, transition section and inner valve support may include cells. The cells of each of the outer section, transition section and inner valve support may define a cell pattern. The cell pattern may be a maximum amount of cells disposed radially about a circumference of the implant. The cell pattern may be a 12-cell pattern. The cell pattern may be a 15-cell pattern. The cell pattern may include any suitable number of cells. The cell patterns of the outer section, transition section and inner valve support may be the same. The cell patterns of the outer section, transition section and inner valve support may be different from each other.

The implant may have a constrained configuration. The constrained configuration may be a configuration in which the implant is compressed by a radial force. The radial force may be an external force exerted on the implant. For example, the constrained configuration may be a configuration in which the implant is compressed in a delivery catheter in order to be delivered to a patient.

The implant may have a relaxed configuration. The relaxed configuration may be a configuration in which there is no radial force exerted on the implant. The relaxed configuration may be a configuration in which a minimal radial force is exerted on the implant. The relaxed configuration may be a configuration in which the radial force exerted on the implant is less than the radial force exerted on the implant when the implant is in a constrained configuration.

The relaxed configuration may be a configuration in which the implant is self-expanded and in which there is no external force other than gravity exerted on the implant, for example, when the implant is outside of a patient or when the implant resting on a flat surface, or when a delivery cable, but no other delivery apparatus, is engaged with the implant.

The implant may include a hub. The hub may include titanium. The hub may include any other suitable material.

The implant may include a strut. The strut may be one of a plurality of struts. The struts may define the cells. The struts may define the cell patterns. The strut may include an end. The end may be configured to be "captured" by the hub cap. Each of the plurality of struts may have a first end. Each of the plurality of struts may have a second end. At least one end may not be configured to be captured by the hub. The first end may be captured by the hub. The second end may not be configured to be captured by the hub.

The hub may receive an end of a strut. The hub may receive an end of each strut included in the plurality of struts. The hub may receive an end of some of the struts included in the plurality of struts.

The end of each strut, captured by the hub, when in the relaxed configuration may define a reference angle. The reference angle may be an angle of the strut end, relative to a longitudinal axis of the hub, in the expanded configuration. The reference angle may be an angle defined when the implant is expanded and placed on a laboratory bench, annular ring down. The reference angle may be curved when the hub is not aligned with the inner valve support.

Table 1 lists illustrative angle ranges that may include the reference angle.

TABLE 1

| Illustrative angle ranges that may include the reference angle. Illustrative angle ranges that may include the reference angle |
|---|
| <0° |
| 0°-15° |
| 15°-30° |
| 30°-45° |
| 45°-60° |
| 60°-75° |
| 75°-90° |
| >90° |

Any other suitable angle ranges

The reference angle for the end of each strut included in the hub may be the same reference angle. The reference angle for the end of each strut included in the hub may vary.

The implant may include a swivel body. The hub may include the swivel body. The swivel body may have a cubed-like shape. The swivel body may have any suitable shape. The swivel body may include titanium. The swivel body may include stainless steel. The swivel body may include any other suitable material. The swivel body may be configured to engage a shaft of the delivery cable. Engagement of the shaft of the delivery cable to the swivel body may couple the shaft to the swivel body.

The shaft may be solid. The shaft may be hollow. The delivery cable may include the shaft and a torque wire. The shaft may be coupled to the torque wire. The delivery cable may be configured to deliver the implant into a heart chamber.

When the implant is disposed in the delivery catheter, the shaft may be colinear with the longitudinal axis of the implant. When the implant is pushed out from the end of the delivery catheter, the swivel block may allow the longitudinal axis to rotate relative to the shaft. This may allow the delivery cable to linearly advance the hub to a deployment location when the implant is being turned for insertion into a valve annulus. When this happens, the swivel block may pass through the reference angle. If the implant is retracted, the swivel block may pass through the reference angle in the other direction. For the sake of simplicity, the reference angle is an angle relative to the longitudinal axis of the hub when the implant is in the expanded state.

The swivel body may define an interior. The interior may be a non-threaded interior. The interior may be a threaded interior. The threaded interior may be a threaded bore. The threaded interior may be configured to receive the shaft.

The shaft may include threads. The shaft may include male threads. The threaded interior may include female threads. The female threads in the threaded interior may be configured to accept the male threads of the shaft. The shaft may be threadingly joined to the threaded interior of the swivel body.

The swivel body may be rotatable when the swivel body is coupled to the shaft. The swivel body may be rotatable when the swivel body is not coupled to the shaft.

The shaft may include a first engagement structure. The first engagement structure may be threads. The implant may include a second engagement structure. The second engagement structure may be included in the hub. The second engagement structure may be included in the swivel body. The second engagement structure may be threads. The threads may be the threaded interior.

The shaft may include a catch. The shaft may be releasably joined to the interior of the swivel body. The shaft may include a release. The swivel body may include a release. The shaft may be removed from the interior of the swivel body when the release is depressed. The shaft may be joined to the swivel body using any suitable engagement structure.

The swivel body may be configured to be rotated through the reference angle. The swivel body may be rotated at angle that is greater than the reference angle.

Table 2 shows illustrative angle ranges that may include an angle of rotation of the swivel body through the reference angle.

TABLE 2

| Illustrative angle ranges that may include an angle of rotation of the swivel body through the reference angle. |
|---|
| 0°-45° |
| 45°-90° |
| 90°-135° |
| 135°-180° |
| 180°-225° |
| 225°-270° |
| 270°-315° |
| 315°-360° |
| >360° |

Any other suitable angle ranges

The implant may include a connector. The connector may extend between the swivel body and the hub. The connector may include a swivel arm. The swivel arm may be configured to rotate inside a receptacle. The swivel arm may extend from the swivel body. The receptacle may be defined by the hub. The swivel arm may extend from the hub. The swivel body may define the receptacle.

The swivel arm may be a first swivel arm. The connector may include a second swivel arm. The second swivel arm may extend away from the swivel body. The first swivel arm may be configured to rotate in a first receptacle. The second swivel arm may be configured to rotate in a second receptacle. The second receptacle may be defined by the hub. The first and second swivel arms may extend axially away from each other.

The first swivel arm, the second swivel arm and the swivel body, together, may be of monolithic construction. The first and second swivel arms may be affixed to the swivel body. The first and second swivel arms may be welded to the swivel body.

The swivel body may be retained by the hub after deployment of the implant. The swivel body may be retained by the hub after withdrawal of the shaft of the delivery cable from a patient. The swivel body may be retained by the hub after closure of an access hole in the patient. The access hole may be a septal crossing. The access hole may be a femoral vein.

The implant may include a hub cover. The hub cover may be disposed on the hub. The hub cover may include a fabric. The hub cover may include any other suitable material. The hub cover may include a suture. The suture may secure the hub cover to the hub. The suture may be connected to a strut from the plurality of struts. The suture may be connected to one or more struts included in the plurality of struts. The suture may be connected to the hub. The hub cover may include a plurality of sutures. The plurality of sutures may be connected to two or more struts included in the plurality of struts. The plurality of sutures may be connected to the hub. The hub cover may be connected to the hub, such that the hub cover does not obstruct access to the swivel body.

The hub may include a hinge block. The hinge block may be a block support. The hinge block may be a frame. The hinge block may be any suitable supporting structure. The swivel body may be configured to rotate with respect to the hinge block. The swivel body may define an axis of rotation with respect to the hinge block. The axis of rotation may be an axis about which the swivel body is configured to rotate. The axis of rotation may be a central axis of the hub. The swivel body may be rotatable at least 90° about the axis of rotation. The swivel body may be rotatable at least 180° about the axis of rotation. The swivel body may be rotatable at least 360° about the axis of rotation.

The hinge block may include a top segment. The hinge block may include a middle segment. The hinge block may include a bottom segment. The top segment may be a top layer of the hinge block. The top segment may define an upper surface of the hub. The middle segment may be a middle layer of the hinge block. The bottom segment may be a bottom layer of the hinge block.

The top segment, the middle segment and the bottom segment may be discoidal. The top segment, the middle segment and the bottom segment may be any suitable shape. The top segment may include an upper face, a bottom face and a thickness. The middle segment may include an upper face, a bottom face and thickness. The bottom segment may include an upper face, a bottom face and a thickness.

The middle segment may define a plurality of "T"-shaped slots. A "T"-shaped slot may include a slot that includes a horizontal cutout. The horizontal cutout may be perpendicular to a vertical cutout. The middle disk may define the first receptacle. The middle disk may define the second receptacle. The first and second receptacles may be straight slots that are configured to capture the first and second swivel arms, respectively. The middle segment may define a gap. The first receptacle may extend away from the gap in a first direction. The second receptacle may extend from the gap in a second direction. The second direction may be opposite the first direction.

The end of each strut configured to be captured by the hub may include a "T"-shaped terminus. The "T"-shaped terminus may include a crossbar. The "T"-shaped terminus may include an arm extending perpendicularly from the crossbar. Each "T"-shaped terminus may be positioned in one of the "T"-shaped slots. The crossbar may be positioned in the horizontal cutout of the "T"-shaped slot. The arm may be positioned in the vertical cutout of the "T"-shaped slot.

The middle segment may include six "T"-shaped slots. The middle segment may include any suitable number of "T"-shaped slots. Each of the "T"-shaped slots may capture an end of one of the struts included in the implant.

The bottom segment may include a plurality of straight slots. Straight slots may include slots that include a vertical cutout. Each of the straight slots included in the bottom segment may be configured to be aligned with the vertical cutout of each "T"-shaped slot included in the middle segment.

The straight slots may trap the crossbar of each "T"-shaped terminus. The crossbar may be trapped in the horizontal cutout. The straight slots may trap the crossbar of each "T"-shaped terminus. The crossbar may be trapped when the bottom segment is attached to the middle segment. Each straight may provide clearance for each strut to angulate relative to a central axis of the hub without releasing the crossbar. The straight slot may enable each strut to pivot, within a "T"-shaped slot, by trapping the crossbar in the horizontal cutout.

The bottom segment may define a gap. The gap may be aligned with the gap defined in the middle segment.

The bottom segment may include six straight slots. Each one of the six straight slots may be aligned with one of the six "T"-shaped slots included in the middle segment. The bottom segment may include any suitable number of straight slots. Each one of the straight slots may be aligned with a corresponding "T"-shaped slot from the plurality of "T"-shaped slots included in the middle segment.

The top segment may include neither "T"-shaped slots nor straight slots. The top segment may prevent struts from disengaging from the hub. The top segment may prevent struts from disengaging from the hub when the top segment is affixed to the middle segment. When the top segment is attached to the middle segment, the top segment may trap the crossbar of each "T"-shaped terminus. The crossbar may be trapped in the horizontal cutout.

The top segment may define a gap. The gap may be aligned with the gap defined in the middle segment and the bottom segment.

The top segment and the bottom segment may include neither the first receptacle nor the second receptacle. The top segment and the bottom segment may prevent the swivel body from disengaging from the hub. The swivel body may be captured in the first and second receptacle. When the top segment and the bottom segment are attached to the middle segment, the swivel body may not disengage from the hub.

The top segment may be attached to the upper face of the middle segment. The bottom segment may be attached to the bottom face of the middle segment. The top segment may be welded to the upper face of the middle segment. The bottom segment may be welded to the bottom face of the middle segment. The top segment and the bottom segment may be attached to the middle segment after the end of the struts are positioned in the "T"-shaped slots and the first second arms are positioned in the first and second receptacles.

Attaching the top segment and the bottom segment to the middle segment may enable each "T"-shaped terminus to pivot within the "T"-shaped slot. Each "T"-shaped terminus may pivot relative to the central axis of the hub. Each "T" shaped terminus may pivot from a first position to a second position. The first position may correspond to a position of the strut relative to the hub in the constrained configuration. The second position may correspond to a position of the strut relative to the hub in the relaxed configuration. The angle between the first position and the second position may define a pivot angle for each "T"-shaped terminus. Table 3 lists illustrative angle ranges that may include the pivot angle of each "T"-shaped terminus.

TABLE 3

| Illustrative angle ranges that may include the pivot angle of each "T"-shaped terminus. |
|---|
| <0° |
| 0°-15° |
| 15°-30° |
| 30°-45° |
| 45°-60° |
| 60°-75° |
| 75°-90° |
| >90° |

Any other suitable angle ranges

The hinge block may include a top segment, an upper middle segment, a lower middle segment and a bottom segment. The top segment may be a top layer of the hinge block. The upper middle segment may be a second layer of the hinge block. The lower middle segment may be a third layer of the hinge block. The bottom segment may be a bottom layer of the hinge block. The top segment, the upper middle segment, the lower middle segment and the bottom segment may be discoidal. The top segment, the upper middle segment, the lower middle segment and the bottom segment may be any suitable shape. The top segment may include an upper face, a bottom face and a thickness. The upper middle segment may include an upper face, a bottom, face and thickness. The lower middle segment may include an upper face, a bottom face, and a thickness. The bottom segment may include an upper face, a bottom face and a thickness.

The upper middle segment may include "T"-shaped slots. The upper middle segment may include the first receptacle and the second receptacle. The "T"-shaped slots may capture "T"-shaped ends from a first group of struts. The first and second receptacles may capture the swivel arms of the swivel body. The first and second receptacles may be straight slots that are configured to capture the first and second swivel arms, respectively. The upper middle segment may define a gap. The first receptacle may extend away from the gap in a first direction. The second receptacle may extend from the gap in a second direction. The first direction may be opposite the second direction.

The lower middle segment may include alternating "T"-shaped slots and straight slots. Each one of the straight slots may be aligned with a "T"-shaped slot from the upper middle segment. The "T"-shaped slots in the lower middle segment may capture "T"-shaped ends from a second group of struts. The straight slots may trap the crossbar of each "T" shaped terminus from the first group of struts. The straight slots may provide clearance for struts from the first group of struts to angulate relative to a central axis of the hub without releasing the crossbar.

The upper middle segment may include four "T"-shaped slots. The lower middle segment may include five "T"-shaped slots alternating with four straight slots. The upper middle disk segment may include any suitable number of alternating "T"-shaped slots. The lower middle segment may include any suitable number of "T"-shaped slots and straight slots. Each of the straight slots in the lower middle segment may be aligned with a "T"-shaped slot from the upper middle segment.

The lower middle segment may define a gap. The gap may be aligned with the gap defined in the upper middle segment.

The bottom disk may include straight slots. The straight slots may trap the crossbar of each "T"-shaped terminus from the second group of struts. The straight slots may provide clearance for struts from the first and second groups of struts to angulate relative to the central axis of the hub without releasing the crossbar.

The bottom disk may include nine straight slots. Each of the nine straight slots may be positioned immediately below and aligned with either a straight slot or a "T"-shaped slot from the lower middle disk. The bottom disk may include any suitable number of straight slots. Each straight slot may be positioned immediately below and aligned with either a straight slot or a "T"-shaped slot from the lower middle disk.

The bottom segment may define a gap. The gap may be aligned with the gap defined in the upper middle segment and lower middle segment.

The top segment may include neither "T"-shaped slots nor straight slots. The top segment may prevent struts from disengaging from the hub. When the top segment is attached to the upper middle segment, the top segment may trap the crossbar of the "T"-shaped terminus of each strut end and prevent the struts from disengaging from the hub.

The top segment and the lower middle segment may include neither the first receptacle nor the second receptacle. The top segment and the lower middle segment may prevent the swivel body from disengaging from the hub. The swivel body may be captured in the first and second receptacle. When the top segment and the lower middle segment are attached to the middle segment, the swivel body may not disengage from the hub.

The top segment may define a gap. The gap may be aligned with the gap defined in the upper middle segment, lower middle segment and the bottom segment.

The top segment may be attached to the upper face of the upper middle segment. The bottom face of the upper middle segment may be attached to the upper face of the lower middle segment. The bottom segment may be attached to the bottom face of the lower middle segment. The top segment may be welded to the upper face of the upper middle segment. The bottom face of the upper middle segment may be welded to the upper face of the lower middle segment. The bottom segment may be welded to the bottom face of the lower middle segment.

The reference angle may be the same for the struts captured in the "T"-shaped slots included in the upper middle segment. The reference angle may be the same for the struts captured in "T"-shaped slots included in the lower middle segment. The reference angle of the struts captured in the "T"-shaped slots included in the upper middle segment may be different than the reference angle of struts captured in "T"-shaped slots included in the lower middle segment. The reference angle of the struts captured in the "T"-shaped slots included in the upper middle segment may be the same as the reference angle of the struts captured in "T"-shaped slots included in the lower middle segment.

The hinge block may include a top segment and a bottom segment. The hinge block may include a single segment. The hinge block may include any suitable number of segments.

The hinge block may circumscribe a cylindrical-like shape. The hinge block may be any other suitable shape. The hinge block may define a gap. The gap may be defined by the top, bottom and middle segments. The gap may be defined by the top, upper middle, lower middle and bottom segments. The gap may extend into an interior of the cylindrical-like shape. The gap may extend into an interior of the hinge block.

The gap may include a rectangular recess. The swivel body may be disposed in the rectangular recess. The rectangular recess may enable access to the swivel body. The gap may include a cylindrical cavity. The cylindrical cavity may extend away from the rectangular recess. The cylindrical body cavity may receive a protrusion from an implant delivery device. The protrusion may be included in a bushing. The hub may be positioned on the bushing. The gap may include a flared opening. The flared opening may extend away from the cylindrical cavity. The flared opening may receive a positioner catheter. The positioner catheter may be included in the implant delivery device. The positioner catheter may be a catheter through which a snare of the implant delivery device extends. The snare may be formed from nitinol, stainless steel, or any other suitable material. The snare may include a loop at a snare distal end.

The apparatus and methods may include apparatus for advancing the implant into the delivery catheter. The apparatus and methods may include apparatus for delivering the implant through a delivery catheter to a heart chamber.

The apparatus may include the pusher catheter. The apparatus may include the delivery cable. The apparatus may include the bushing. The apparatus may include the positioner catheter. The apparatus may include the snare.

The apparatus may be advanced into the delivery catheter such that the implant is loaded in the delivery catheter. When the implant is loaded in the delivery catheter, the hub of the implant may be seated on the bushing, the delivery cable may be coupled to the hub, the positioner may extend through the implant and the snare may circumscribe an inner surface of the implant.

During delivery, the delivery catheter may be advanced through a sheath and into the heart chamber. When the delivery catheter is positioned at, or advanced through, a distal end of the sheath, the apparatus may deploy the implant out of the delivery catheter to the heart chamber.

The bushing may be fixed to an end of the pusher catheter. The bushing may be configured to be moved along a delivery catheter lumen. The bushing may be configured to guide the implant to a keyed position at the bushing.

The implant may be seated at the keyed position during loading of the implant into the delivery catheter. The implant may be seated at the keyed position during advancement of the delivery catheter through the sheath and into the body cavity. The implant may be seated at the keyed position during withdrawal of the delivery catheter from the implant in the body cavity.

The bushing may be configured to be moved to a position outside the delivery catheter lumen. The bushing may be configured to be retracted from the position outside the lumen into the lumen.

The bushing may be advanced (distally) through the delivery catheter to a body cavity or withdrawn (proximally) into the delivery catheter toward a main handle.

The apparatus may include the delivery cable. The delivery cable may be configured to engage the implant. The delivery cable may be configured to draw the implant into the keyed position.

When the delivery cable is engaged with the implant, movement of an end of the delivery cable away from the bushing may disengage the implant from the bushing. The end may be a distal end.

The delivery cable may be configured to disengage the implant from the bushing. The delivery cable may be configured to disengage the implant when the bushing is outside the delivery catheter. The delivery cable may be configured to disengage the implant when the bushing is inside the delivery catheter.

The delivery cable may extend through a lumen of the pusher catheter. The delivery cable may be rotatable within the pusher catheter lumen. The delivery cable may be configured to be moved longitudinally through the pusher catheter. The delivery cable may be configured to be moved in tandem with the pusher catheter.

An end of the delivery cable may include the shaft. The shaft may be configured to removably engage the implant. A portion of the shaft may be threaded. The shaft may be configured to threadingly engage the implant. The shaft may be configured to threadingly engage the hub. The shaft may be configured to threadingly engage the threaded interior of the swivel body.

When the implant is coupled to the delivery cable, the implant may be distal the bushing. Advancing the bushing outside the delivery catheter lumen may push the implant into the heart chamber. Retracting the bushing into the delivery catheter lumen may, initially, load the implant in the delivery catheter and, after deployment, recapture the implant in the delivery catheter. A funnel may be used to collapse the implant during loading.

During deployment, a distal end of the delivery cable may be moved away from the bushing to position the hub of the implant at a desired location in the body cavity. When the body cavity is a heart chamber, the delivery cable may be advanced past the bushing to disengage the hub from the bushing and position the hub at a top of the heart chamber. After the hub has been positioned, the delivery cable may be disengaged from the implant and withdrawn into the delivery catheter. The disengaging of the delivery cable may include rotating the delivery cable to unthread the shaft from the swivel body.

The bushing may define a bore. The bore may be configured to receive the delivery cable. A terminal end of the pusher catheter may be coaxial with the bore. The terminal end of the pusher catheter may be fixedly coupled to the bushing. Because of the coupling of the pusher catheter to the bushing, movement of the pusher catheter may move the bushing.

The bore may be a first bore. The bushing may define a second bore. The second bore may be for engaging a positioner catheter. The positioner catheter may be slidingly received within the second bore.

The bushing may include a protrusion that is configured to engage a recess in the implant. The recess may be a cavity in the hub. The cavity may be the cylindrical cavity. The recess may be an indentation in the hub.

The protrusion may be configured to urge the implant to seat on the bushing in a predetermined rotational orientation. The predetermined rotational orientation may be relative to a central axis of the bushing. When the implant is seated on the bushing and the recess is engaged with the protrusion, the implant may be fixed with respect to rotation about an implant central axis. When the implant is seated on the bushing and the recess is engaged with the protrusion, the implant may be fixed with respect to rotation about the bushing central axis.

The bushing may define a passageway that is configured to receive a positioner catheter. The passageway may be the second bore. The positioner catheter may be configured to extend through the second bore, through the flared opening defined by the hub, and into a volume defined by the implant. The positioner catheter may be configured to be moved through the bushing to change an orientation of the implant relative to a central axis of the delivery catheter.

The apparatus may include a snare that is configured to be moved through the positioner. The snare may be configured to circumscribe an internal section of the implant. The internal section may be the inner valve support. The snare may couple the positioner to the implant. The snare may couple a distal end of the positioner to the implant.

The snare may be configured to circumscribe the annular ring.

The bushing may include the protrusion that is configured to engage the recess in the implant. A distal end of the delivery cable and the protrusion may be configured to urge the implant to seat on the bushing in a predetermined rotational orientation relative to a central axis of the implant. An outer surface of the positioner catheter and the protrusion may be configured to urge the implant to seat on the bushing in a predetermined rotational orientation relative to a central axis of the hub of the implant.

The apparatus and methods may include apparatus for delivering the implant through the delivery catheter to a heart chamber.

The apparatus may include the delivery catheter. The delivery catheter may be configured to deliver the implant. The apparatus may include the delivery cable.

The delivery cable may be configured to be translated in the delivery catheter. The delivery cable may be configured such that, when there is tension between the delivery cable and the implant, the delivery cable may fail.

The failure may include a fracture of the delivery cable. The fracture may be a complete fracture. The fracture may be a partial fracture. The failure may be an incipient fracture.

The delivery cable may fail when the delivery cable is unable to transmit a force to the implant. The delivery cable may fail when the delivery cable experiences a material failure. The delivery cable may fail when the delivery cable breaks into one or more pieces.

The delivery cable may fail under a tension that is less than that at which the implant may fail. The delivery cable may fail at a location inside the implant. A tension at which an apparatus fails may correspond to a failure strength of the apparatus. The delivery cable failure tension may correspond to a delivery cable failure strength. The tension at which the implant may fail may be a predetermined tension. The predetermined tension may correspond to an implant failure strength.

During delivery of the implant, the delivery cable may be removably engaged to the implant.

The delivery cable may have an end that includes the shaft. The end may be a distal end.

The shaft may include a first section. The first section may include the first engagement structure. The first engagement structure may be configured to engage the second engagement structure. The second engagement structure may be in the implant. The second engagement structure may be in the hub of the implant. The second engagement structure may be in the swivel body of the hub. The second engagement structure may be the threaded interior of the swivel body.

The delivery cable may include a tip. The tip may be a delivery cable tip. The tip may be positioned at a distal end of the delivery cable. The shaft may include the tip. The tip may be positioned at a distal end of the shaft.

The tip may define a surface. The tip may have a volume. The tip may not be threaded. The tip may be threaded.

The first section may include the tip. The first section may not include the tip. The tip may be distal the first section.

The delivery cable may not include the tip.

The first engagement structure may be a thread. The second engagement structure may be a thread. One or both of the first and second engagement structures may include one or more protrusions, a catch, an expanding mechanism, or the like.

The shaft may include a second section. The second section may be a section that does not include the first engagement structure. The second section may include a predetermined failure region. The second section may be proximal the first section. The second section may be a neck.

The predetermined failure region may include a failure surface. The delivery cable may fail at the failure surface.

The second section may be the predetermined failure region. When the delivery cable is removably engaged with the implant, the predetermined failure region of the delivery cable may be inside the implant.

The predetermined failure region may be configured to be below a plane defined by a top surface of the hub. The predetermined failure region may be within a region defined by an outer perimeter of the hub.

The system may fail at a location other than the predetermined failure region. The system may fail at a weld between the pusher catheter and the bushing. The system may fail at a weld between the delivery cable and a cylindrical boss. The system may fail at a weld between the pusher catheter and an encasement member. The system may fail at a weld between the third section and the second section. The system may fail at, or adjacent, a weld between the torque wire and the shaft.

The second engagement structure may be disposed in the hub of the implant. When the first engagement structure is engaged with the second engagement structure, the predetermined failure region may be disposed in the hub.

The first section may be positioned at a first end of the delivery cable. The first end may be a distal end. The shaft may include a third section. The third section may extend between the second section and a second end of the delivery cable. The second end may be a proximal end.

The third section may comprise one or more tubes. The third section may have a constant diameter along a length of the third section. The third section may have a diameter that varies along the length of the third section. The third section may have a constant thickness along the length of the third section. The third section may have a thickness that varies along a length of the third section.

The second section may fail at a tension that is less than that at which the third section fails. The second section may fail at a tension that is less than that at which the first section fails. When the first section is engaged with the hub, the second section may fail at a tension that is less than that at which the first section fails.

The second section may have a length. The second section may fail at a location along the length.

During deployment of the implant in the heart chamber, the first engagement structure may be removably engaged with the second engagement structure. In the event the delivery cable fails, the delivery cable may fail at a location on the second section. The delivery cable may fail at a failure surface.

The failure may separate the first section from the third section. After the failure, the first section may be positioned in the hub. The third section may be withdrawn. A portion of the second section extending away from the first section after the failure may be in the hub. Thus, a failure surface, which may be sharp, may be prevented from contacting tissue.

The delivery cable may have an end including the shaft that is configured to removably engage the implant. The shaft may include the first section, the second section, and the predetermined failure region.

The first section may include the predetermined failure region. When the first engagement structure is engaged with the second engagement structure, the predetermined failure region may be disposed in the hub.

The first section and the second section may include the predetermined failure region. When the first engagement structure is engaged with the second engagement structure, the predetermined failure region may be disposed in the hub.

The delivery cable may include the delivery cable tip. A portion of the delivery cable extending between the second section and the tip may include the predetermined failure region. When the first engagement structure is engaged with the second engagement structure, the predetermined failure region may be disposed in the hub.

The second section may have a failure strength that is less than a failure strength of one or more of: the implant, the "T-slots", the swivel body, the swivel arms, the first engagement structure, the second engagement structure, the first section and the third section.

The apparatus and methods may include apparatus for manipulating the implant. The manipulation may include loading the implant into the delivery catheter. The manipulation may include deploying the implant out of the delivery catheter and into a heart chamber. The manipulation may include repositioning the implant within the heart chamber. The manipulation may include recapturing the implant into the delivery catheter after partial deployment of the implant in the heart chamber. The manipulation may include recapturing the implant into the delivery catheter after complete deployment of the implant in the heart chamber. The manipulation may include moving the implant through the delivery catheter.

The apparatus may include a main handle. The apparatus may include a gauge handle.

The apparatus may include the delivery catheter. The apparatus may include the pusher catheter. The apparatus may include the delivery cable.

The main handle may advance and withdraw the delivery catheter. The main handle may advance and withdraw the pusher catheter. The delivery cable may move with the pusher catheter. The delivery cable may move separately from the pusher catheter. The delivery cable may extend through the pusher catheter. The delivery catheter and the pusher catheter may be coaxial. The pusher catheter may be slidable within the delivery catheter.

The apparatus may include a sheath. The sheath and the delivery catheter may be coaxial. The sheath may be advanced or withdrawn over the delivery catheter. A stand may hold the apparatus during deployment of the implant. The stand may withdraw or advance the sheath. The stand may advance the sheath into the heart chamber prior to advancing the delivery catheter to the heart chamber. The sheath may be steerable. The sheath may be steerable within the heart chamber. The delivery catheter may be slidingly mounted within the sheath. The delivery catheter may be steerable via steering of the sheath. The delivery catheter may be unable to be steered independent of the sheath.

A proximal end of the pusher catheter may be removably locked to the gauge handle. A distal end of the pusher catheter may be fixedly coupled to the bushing.

A proximal end of the delivery cable may be removably locked to the gauge handle. A distal end of the delivery cable may be configured to be removably coupled to the hub of the implant. The distal end of the delivery cable may be configured to threadingly engage the hub.

The gauge handle may include a first base. The gauge handle may include a second base. The proximal end of the pusher catheter may be removably locked to the second base. The proximal end of the delivery cable may be removably locked to the first base.

The gauge handle may be disposed proximal the main handle. The gauge handle may be disposed distal the main handle. Positioning of the gauge handle proximal the main handle may reduce or eliminate the need for sterilization of the gauge handle. Positioning of the gauge handle proximal the main handle may reduce or eliminate conflicting needs for positioning other surgical resources, including personnel and equipment.

The gauge handle may include a force gauge. The force gauge may indicate the presence of a force acting on the implant. The force may be a force acting on the implant other than that of the delivery cable. The force gauge may include a display. The display may include an analog display. The display may include a digital display. The display may show a measure of the force.

The force gauge may be coupled to the first base. The force gauge may be coupled to the second base. The first base may be spaced apart from the second base to define a gap. The force gauge may be extended across the gap.

A pin may be disposed in a bore in a first end of the first base and a bore in a first end of the second base. The pin may axially and radially align the first base with the second base. The pin may prevent the first base from rotating relative to the second base. The pin may traverse the gap. The pin may be positioned in the bores via a pressed fit. The pin may define a non-circular cross-section. A shape of a cross-section of the bores may be equivalent as a shape of the cross-section of the pin. The cross-section of the bores may be slightly larger than a cross-section of the pin.

The force gauge may include at least two pins. The force gauge may include a corresponding number of bores to pins on each of the first and second bases. Each of the at least two pins may define a circular cross-section. Each of the at least two pins may define a non-circular cross-section. A shape of a cross-section of the corresponding bores may be equivalent as a shape of the cross-section of the corresponding pins. The cross-section of the bores may be slightly larger than a cross-section of the pin.

An outer surface of the first and second bases may together define a recess. The force gauge may be disposed in the recess. Bosses may extend from the first and second bases. The bosses may extend into the recess. The bosses may support the force gauge across the gap. The first and second bases may be cylindrical. The first and second bases may be any suitable shape. The bosses may include a first boss extending from the first base and a second boss extending from the second base. A first fastener may be inserted through the first boss and threaded into a threaded bore in a first side of the force gauge. A second fastener may be inserted through the second boss and threaded into a threaded bore in a second side of the force gauge. The fasteners may support the force gauge across the gap.

The first base may define a first cannula. The delivery cable may be positioned in the first cannula. A proximal end of the delivery cable may terminate in the first cannula. The delivery cable may be removably locked to the first base inside the first cannula.

The proximal end of the delivery cable may include the cylindrical boss. The delivery cable may be welded to the cylindrical boss. The cylindrical boss may be positioned within the first cannula. The cylindrical boss may be removably locked to the first base via fasteners. The fasteners may be inserted through a thickness of the first base and into threaded bores in the cylindrical boss, locking the cylindrical boss to the first base.

The second base may define a second cannula. The delivery cable may extend through the second cannula. The pusher catheter may be positioned in the second cannula. A proximal end of the pusher catheter may terminate in the second cannula. The pusher catheter may be removably locked to the second base inside the second cannula.

The proximal end of the pusher catheter may include the encasement member. An outer surface of the encasement member may define grooves. The pusher catheter may be welded to the encasement member. The pusher catheter may be held in place within the encasement member by an O-ring. The O-ring may be a thermoplastic O-ring. The O-ring may include any suitable material.

The pusher catheter may be removably locked to the second base via a biased lock. The biased lock may be operable from outside the gauge handle.

The biased lock may include a spring. The spring may be disposed between a top of the lock and second base to bias the biasing lock in a non-depressed state. When the pusher catheter is locked to the second base the biased lock may engage the grooves defined in the encasement member. Depressing the biased lock may disengage the biased lock from the grooves to unlock the pusher catheter from the second base.

The biased lock may include first, second and third cutouts. The first and second cutouts may receive pins. The pins may be configured to prevent removal of the lock from the second base. The third cutout may define a circular section and an elongated section. The circular section may be shaped to receive the encasement member. The elongated section may be shaped to engage the grooves.

The main handle may move the pusher catheter. The movement may include advancing and withdrawing the pusher catheter. Moving the pusher catheter via the main handle, when the delivery cable is locked to the first base and the pusher catheter is locked to the second base, may move the gauge handle, the pusher catheter and the delivery cable in unison relative to the main handle.

The force gauge may indicate the presence of a force acting on the implant other than that of the delivery cable. The force may include a differential force. The differential force may be between the delivery cable and the pusher catheter. The differential force may include a tensile force. The differential force may include a compressive force.

A force may act on the implant while the implant is being manipulated.

The force gauge may include a mark to indicate a threshold force. A force greater than the threshold force may cause portions of the apparatus to materially fail. A force greater than the threshold force may cause a portion of the apparatus subject to the force to fail. A force greater than the threshold force may cause an incipient fracture. The portion may be the predetermined failure region. The portion may be apparatus different from the predetermined failure region, such as a weld between the delivery catheter and the cylindrical boss or a weld between the pusher catheter and the encasement member.

The threshold force may be 35, 40, 45, 50, 55, 60, 65, 70 or any suitable number of pounds force ("lbf").

The apparatus and methods may include methods for loading the implant into the apparatus. The methods may include sliding an implant loading device onto the distal end of the delivery catheter. The implant loading device may be a funnel. The methods may include flushing the delivery catheter with biocompatible fluid. The biocompatible fluid may be saline. The delivery catheter may be tilted such that the implant loading device fills with the biocompatible fluid and is purged of air.

The methods may include removably coupling the implant to the delivery cable. The removable coupling may be via a threaded engagement between the implant and the delivery catheter. The methods may include drawing the implant completely into the delivery catheter of the apparatus. During the drawing the delivery catheter may be continuously flushed with the biocompatible fluid. During the drawing a display of the force gauge may be observed. When the observed force exceeds a loading force threshold the drawing may be paused. The loading force threshold may vary based on characteristics of the implant. The characteristics may include a size, shape, stiffness, density or any other suitable characteristic of the implant. The loading force threshold may be 35, 40, 45, 50, 55, 60, 65, 70 or any suitable number of pounds force ("lbf").

The observed force exceeding the loading force threshold may indicate the implant has a catch. A catch may include a portion of the implant experiencing drag from or being snagged by the apparatus. A strut of the implant may experience drag from or be snagged by the implant loading device. The strut of the implant may experience drag from or be snagged by the delivery catheter. A skirt of the implant may experience drag from or be snagged by the implant loading device. The skirt of the implant may experience drag from or be snagged by the delivery catheter. The observed force exceeding the loading force threshold may indicate portions of the apparatus are close to a failing.

The methods may include assessing the implant and the delivery catheter while the drawing is paused. The methods may include assessing the delivery catheter for buckling. The methods may include assessing a tip of the delivery catheter for crimps or deformations. The delivery catheter tip may be positioned at a distal end of the delivery catheter. The methods may include assessing the implant for catches. The methods may include assessing the implant for size.

The methods may include stretching the delivery catheter by hand or replacing the delivery catheter when the delivery catheter becomes buckled. The methods may include straightening out or replacing the tip of the delivery catheter when the tip of the delivery catheter becomes crimped or deformed. The snags may damage the implant. The methods may include unsnagging or replacing the implant when the implant becomes snagged. The methods may include replacing the implant when the implant is determined to be mis-sized.

The methods may include removing the implant loading device after the implant is completely drawn into the delivery catheter.

The apparatus and methods may include methods for recapturing the implant from a heart chamber into the apparatus. In the context of this application recapture may be defined as withdrawing a partially deployed implant out of a heart chamber and into the delivery catheter. A partially deployed implant may be defined as an implant partially pushed out of the delivery catheter while the hub remains within the delivery catheter.

The methods may include tightening the positioner to cinch and reduce a diameter of the annular ring of the implant. The methods may include withdrawing the implant into the delivery catheter until the inner valve support of the implant is positioned at the tip of the delivery catheter. The tip of the delivery catheter may be the distal end of the delivery catheter. The methods may include verifying the location of the implant via fluoroscopic imaging. The methods may include partially straightening the sheath.

The methods may include positioning the delivery catheter radiopaque ("RO") marker band a predetermined distance past a tip of the sheath. The sheath tip may be positioned at a distal end of the sheath. The predetermined distance may include 5, 6, 7, 8, 9, 10 mm or any suitable number of mm past the tip of the sheath. The methods may include advancing the sheath over the delivery catheter and over the implant to collapse the inner valve support and the annular ring.

When the observed force exceeds a recapturing force threshold, the advancing may be paused. The recapturing force threshold may vary based on characteristics of the implant. The characteristics may include a size, shape, stiffness, density or any other suitable characteristic of the implant. The recapturing force threshold may be 35, 40, 45, 50, 55, 60, 65, 70 or any suitable number of pounds force ("lbf"). The recapturing force threshold may be smaller than the loading force threshold.

The observed force exceeding the recapturing force threshold may indicate the implant has a catch. A catch may include a portion of the implant getting snagged or stuck on the apparatus. A strut of the implant may snag on the sheath. The strut of the implant may snag on the delivery catheter. A skirt of the implant may snag on the sheath. The skirt of the implant may snag on the delivery catheter. The observed force exceeding the recapturing force threshold may indicate portions of the apparatus are close to material failure. The observed force exceeding the recapturing force threshold may indicate the occurrence of an incipient fracture.

The methods may include assessing the implant and the delivery catheter while the advancing is paused. The methods may include assessing the delivery catheter for buckling. The methods may include assessing a tip of the delivery catheter for crimps or deformations. The methods may include assessing the implant for snags or catches. The assessing may be performed under fluoroscopy. One or more of the delivery catheter tip, a pusher catheter tip and the sheath tip may include a radiopaque ("RO") band. The pusher catheter tip may be positioned at a distal end of the pusher catheter. The RO band may be viewed under fluoroscopy. The RO band may indicate the position of the delivery catheter tip, pusher catheter tip and sheath tip inside the body, while under fluoroscopy.

The methods may include withdrawing the sheath from the delivery catheter when the implant becomes snagged. The methods may include repositioning or tightening the cinch of the positioner, after the sheath is withdrawn. The methods may include advancing the sheath over the delivery catheter again, after the cinch is repositioned or tightened, to recapture the implant. The methods may include withdrawing the sheath from the delivery catheter when the delivery catheter buckles or deforms. The methods may include repositioning or tightening the cinch of the positioner, after the sheath is withdrawn. The methods may include advancing the sheath over the delivery catheter again, after the cinch is repositioned or tightened, to recapture the implant.

The methods may include straightening the sheath after the sheath is completely advanced over the implant. The methods may include drawing the implant into the delivery catheter. The methods may include removing the delivery catheter from the sheath. Removing the delivery catheter from the sheath may remove the delivery catheter from the patient.

The methods may include methods for loading the implant. The methods may include one or more of the following:

1. Slide the implant loading device onto the distal end of the delivery catheter, then angle the delivery catheter and flush with saline so the implant loading device is filled with saline and purged of air;
2. Connect the implant to the delivery catheter;
3. Connect the snare to the inner valve support of the implant and cinch;
4. Draw the implant completely into the delivery catheter while flushing with saline;
5. While drawing the implant into the delivery catheter, observe the loading force on the force gauge display;
6. If the loading force becomes ≥a predetermined force, the predetermined force may be 35, 40, 45, 50, 55, 60 or any other suitable force, stop and re-assess the delivery catheter. Use delivery catheter controls to reduce the force to ≤the predetermined force prior to continuing to step 7;
7. If determined necessary, obtain a new delivery catheter/implant, and repeat steps 1-6;
8. Remove the implant loading device.

The methods may be performed in any suitable order.

The methods may include methods for recapturing the implant. The methods may include one or more of:

1. Tighten the snare to cinch and reduce an annular ring diameter;
2. Use delivery catheter controls to recapture the implant until the inner valve support is at the delivery catheter tip;
3. Verify implant location via fluoroscopy;
4. Partially unsteer the sheath and retract the system to position the sheath RO marker band near the septal puncture site and orient the system towards the left pulmonary veins;
5. Position the delivery catheter RO marker band approximately 5-10 mm past the sheath tip;
6. Use stand controls to advance the sheath over delivery catheter and over the implant to collapse the inner valve support and annular ring. Do not use any other knobs for recapture;
7. While performing step 6, observe the recapture force on the force gauge display; The force to recapture the implant within the sheath may be ≤a predetermined
8. force, the predetermined force may be 35, 40, 45, 50, 55, 60 or any other suitable force;
9. If the recapture force becomes ≥the predetermined force, stop and re-access the delivery system. Use the stand and delivery catheter controls to reduce ≤the predetermined force prior to continuing to step 10;
10. Unsteer the sheath;
11. Use delivery catheter deployment knobs to completely draw the implant into the delivery catheter;
12. Remove the delivery catheter while aspirating sheath and maintaining the sheath position in the left atrium ("LA");
13. Cover the sheath hemostasis valve with a finger and aspirate the sheath;
14. Remove the sheath from the patient. If needed, an appropriately sized closure device may be used to close the septal hole after sheath removal;
15. Close the femoral access hole using standard methods.

The methods may be performed in any suitable order.

If the implant hemodynamics are unstable and/or other events occur that require the implant procedure to be stopped, the physician may recapture the implant prior to hub placement. Hub placement may include extending the hub away from the bushing by advancing, in the proximal direction the delivery catheter away from the bushing. After hub the delivery cable may be unthreaded from the hub.

The implant may not be re-deployed after recapture.

Illustrative annular ring diameters may be one or more of 32 mm, 36 mm, 40 mm, 42 mm, 44 mm, 46 mm, 50 mm, 54 mm, 56 mm, 58 mm and any other suitable number of millimeters.

The methods may include methods for deploying the implant. The methods may include one or more of:

1. Advancing the pusher catheter, the delivery cable, and the implant toward a target site;
2. Advancing the positioner into the implant;
3. Deploying the snare within the implant;
4. Adjusting the limit screw to a desired position;

5. Pressing the biased lock to unlock the pusher catheter and the delivery cable;
6. Moving the limit screw to the main handle, causing the pusher catheter to push the implant;
7. Deploying the implant;
8. Positioning the implant at the correct location;
9. Removing the positioner from the implant;
10. Rotating the delivery cable to disconnect the delivery cable from the hub;
11. Removing the delivery cable and the pusher catheter from the target site.

The methods may be performed in any suitable order.

The methods may include methods for deploying the implant. The methods may include one or more of:

1. Positioning a guidewire in a heart chamber;
2. Advancing a dilator and a sheath over the guidewire into the heart chamber;
3. Removing the dilator from the sheath;
4. Using the main handle to advance the delivery catheter loaded with the implant to the heart chamber;
5. Advancing the delivery catheter out of the sheath to a location within the heart chamber. The location may be a target site. When the heart chamber is a left atrium, the location may be the mitral valve plane, below the mitral valve plane, or above the mitral valve plane;
6. Deploying the annular ring of the implant by withdrawing the delivery catheter. The deploying may position the annular ring in an annulus at a bottom of the heart chamber;
7. Cinching the snare around the inner valve support;
8. Withdrawing the delivery catheter a few millimeters;
9. Adjusting a depth of the implant within the heart chamber;
10. Deploying the inner valve support by withdrawing the delivery catheter and loosening the snare from around the inner valve support;
11. Withdrawing the delivery catheter until a midpoint of the heart chamber;
12. Adjusting the positioner catheter during the releasing of the implant to maintain a depth of the implant at the target site;
13. Ensuring that the positioner catheter extends along an outer curve of the implant throughout the releasing of the implant;
14. Withdrawing the delivery catheter until the hub of the implant is visibly out of the sheath;
15. Loosening the limit screw;
16. Positioning the hub at the top of the heart chamber by extending the delivery cable. The delivery cable may be extended by advancing the gauge handle toward the limit screw;
17. Uncinching the snare from around the inner valve support and withdrawing the snare into the positioner catheter;
18. Removing the positioner catheter by unlocking the positioner catheter control handle and retracting the positioner catheter into the delivery catheter;
19. Releasing the delivery cable from the hub by rotating the delivery cable;
20. Retracting the delivery cable into the delivery catheter by retracting the gauge handle away from the limit screw;
21. Removing apparatus from the heart chamber using the main handle, the apparatus including the delivery catheter, the pusher catheter, the delivery cable, and the positioner catheter.
22. Removing the sheath from the patient.
23. Closing the access hole.

The methods may be performed in any suitable order.

The apparatus and methods may include measuring force between elements of an implant delivery system.

The delivery system may include the delivery catheter. The implant may be translated along a lumen of the delivery catheter. The delivery system may include the pusher catheter. The pusher catheter may include a pusher. The pusher may be translated inside the delivery catheter. The pusher may be configured to push the implant.

The delivery system may include the delivery cable. The delivery cable may include a cap attachment. The cap attachment may include the torque wire and the shaft. The torque wire may include a metal tube. The shaft may include a torque coil. The metal tube may be welded to the torque coil.

The cap attachment may be disposed inside the pusher. The cap attachment may rotate independent of the pusher. The implant may include the hub. The hub may include a cap. The cap may comprise the swivel body. The swivel body may include a threaded part. The threaded part may be a female threaded part. The threaded part may be pivotably attached to the cap. The cap attachment may include the shaft. The shaft may include a male threaded part. The male threaded part may be configured to thread into the female threaded part. The cap attachment may include the neck.

Movement of the pusher may change an amount of force being applied to the implant. Movement of the cap attachment may change an amount of force being applied to the implant. The delivery system may fail if the force applied to the implant increases above a failure strength.

The delivery system may include a positioner catheter. The positioner catheter may include a snare. The snare may be configured to position the implant at a target site. The target site may be the body cavity. The target site may be the heart chamber. The positioning of the implant may impact the amount of force applied to the implant.

The delivery system may include the main handle. The main handle may include a primary handle. The primary handle may be configured to advance the sheath into a patient and to a target site. The sheath may be a steerable sheath. The primary handle may provide steering and orientation functions for manipulating the sheath. Surgical instruments may be advanced and retracted along a lumen of the sheath.

The delivery catheter may be slidingly mountable within the sheath. The delivery catheter may be advanced and retracted along the lumen of the sheath. The delivery catheter may be steerable via steering of the sheath. The delivery catheter may not be steerable independent of the sheath. The delivery catheter may be steerable independent of the sheath. The implant may be delivered via the delivery catheter. The implant may be a unitary structure. The implant may be monolithic structure. The implant may be formed from a laser-cut tube. The implant may be formed from two or more attached structures.

The apparatus may include the first base. The first base may include a first segment. The apparatus may include the second base. The second base may include a second segment. The first and second segments may together form the gauge handle. The gauge handle may be a secondary handle. The secondary handle may include steel. The secondary handle may include stainless steel. The secondary handle may include polymeric materials. The secondary handle may include any other suitable material.

The secondary handle may include the force gauge. The force gauge may be coupled to the first and second segments. The force gauge may bridge across the gap between the first segment and the second segment. The force gauge may include a transducer. The transducer may convert force into a signal. The force gauge may include an output port. The output port may be configured to provide a signal that is representative of force applied to the transducer. The apparatus may include the display. The display may show an indication of the signal.

The force gauge may include a gauge such as that available from Futek, Irvine, California under the trade name Miniature S-Beam Jr. Load Cell 2.0, Model No. LSB205. The force gauge may include a gauge such as that available from Futek, Irvine, California, under the trade name Digital Hand Held Display Pro, Model No. IHH500.

The first segment may be coupled to the pusher. The pusher may include a first element of the delivery system. The pusher may include an elongated body. The elongated body may include a tube, a rod, braided wire or any other suitable structure. The pusher may be advanced through the delivery catheter to push the implant through the delivery catheter.

The second segment may be coupled to the cap attachment. The cap attachment may include a second element of the delivery system. The cap attachment include a tube, a rod, braided wire or any other suitable structure. The cap attachment may be advanced through the delivery catheter to push the implant through the delivery catheter. The cap attachment may be engaged with the implant. The cap attachment may be retracted through the delivery catheter to retract the implant through the delivery catheter.

The apparatus may include a positioner catheter control handle. The positioner catheter control handle may include a third handle. The positioner may be disposed in the third handle. The positioner may be an elongated body. The elongated body may include a tube, a rod, braided wire or any other suitable structure. The positioner may be advanced through the delivery catheter. The positioner may provide control over a position of the implant during the deployment. In operation, the positioner may be coupled to the implant.

The positioner may extend along some or all of a length of the implant. The positioner may be fixed to an end of the implant. The positioner may extend around an outer or inner surface defined by the implant. The portion of the positioner encircling the surface of the implant may be the snare. The snare may include a stabilizer. The stabilizer may include a loop. The stabilizer may include a nickel-titanium alloy under the tradename Nitinol. The stabilizer may be formed of any other suitable material.

The positioner may be used to maintain a depth of the implant at the target site throughout deployment of the implant at the target site. The positioner may be disposed in a catheter lumen. The positioner may include the stabilizer at an end of the positioner. The stabilizer may be configured to expand inside an implant. The stabilizer may control the deployment of the implant.

A force measured by the transducer may be representative of a force, at a location inside the delivery system, between the pusher and the cap attachment. The location may be at or near the proximal ends of the pusher and the cap attachment.

The second element may be configured to be translated along a lumen of the first element.

The apparatus and methods may include the delivery system. The delivery system may be configured to deliver the implant to a site in a patient. The delivery system may define a proximal direction (away from the patient's heart) and a distal direction (toward the patient's heart).

The secondary handle may be disposed proximal the primary handle. The secondary handle may be disposed distal the primary handle. Positioning of the secondary handle proximal the primary handle may reduce or eliminate the need for sterilization of the secondary handle. Positioning of the secondary handle proximal the primary handle may reduce or eliminate conflicting needs for positioning other surgical resources, including personnel and equipment.

The force may be a proxy for force between the first and the second element. The force may be a proxy for shear force on a linkage to a cap of an implant.

The cap attachment may be rotated to detach the male threaded part from the female threaded part of the cap. The force from the movement of the pusher or the movement of the cap attachment may be exerted on a predetermined failure region of the cap attachment. The predetermined failure region may be at the neck of the cap attachment. The force applied to the predetermined failure region may be measured using the apparatus for measuring force. The predetermined failure region may include a designated failure point.

The pusher and the cap attachment may be disposed in separate catheters. The pusher and cap attachment may not be disposed in separate catheters. The positioner and the cap attachment may be arranged in parallel.

The steps of illustrative methods may be performed in an order other than the order shown or described herein. Some embodiments may omit steps shown or described in connection with the illustrative methods. Some embodiments may include steps that are neither shown nor described in connection with the illustrative methods. Illustrative method steps may be combined. For example, one illustrative method may include steps shown in connection with another illustrative method.

Some embodiments may omit features shown or described in connection with the illustrative apparatus. Some embodiments may include features that are neither shown nor described in connection with the illustrative apparatus. Features of illustrative apparatus may be combined. For example, one illustrative embodiment may include features shown in connection with another illustrative embodiment.

Embodiments may involve some or all of the features of the illustrative apparatus or some or all of the steps of the illustrative methods.

Embodiments may include features that are neither shown nor described in connection with the illustrative apparatus. Features of illustrative apparatus may be combined. For example, an illustrative embodiment may include features shown in connection with another illustrative embodiment. It is to be understood that structural, functional and procedural modifications or omissions may be made without departing from the scope and spirit of the present invention.

The illustrative apparatus and methods will now be described with reference to the accompanying Figures, which form a part hereof. It is to be understood that other embodiments may be utilized and that structural, functional and procedural modifications may be made without departing from the scope and spirit of the present disclosure.

FIG. 1 shows illustrative implant 101 positioned for deployment in left atrium ("LA") and valve annulus 119. Implant 101 is shown as being partially deployed. Implant 101 may include hub 103. Hub 103 may retain ends of struts of implant 101. Hub 103 may be configured to be engaged with a distal end ("D") of delivery cable 105. Delivery cable 105 may be translated proximally ("P") and distally within pusher catheter 107. Pusher catheter 107 may be translated proximally and distally within delivery catheter 115. Implant 101 may include leaflets for replacing the mitral valve (not shown).

Delivery cable 105 and pusher catheter 107 may be mechanically linked in a proximal handle (not shown) that may include the force gauge configured to indicate a differential force between delivery cable 105 and pusher catheter 107.

One or both of delivery cable 105 and pusher catheter 107 may be translated to advance (distally) or withdraw (proximally) implant 101 relative to the heart chamber.

Positioner catheter 109 may be used to position implant 101 within the heart chamber. Positioner catheter 109 may be used to maintain a depth of implant 101 within the heart chamber during release of implant 101 from delivery catheter 115. Snare 111 may extend along a lumen of positioner catheter 109. Snare 111 may be positioned around inner valve support 112. Snare 111 may be positioned around inner valve support 112 to encircle inner valve support 112. Snare 111 may be positioned on inner valve support 112 such that snare 111 is below leaflets supported by inner valve support 112. Snare 111 may be drawn around inner valve support 112 to a desired tension. Snare 111 may be positioned at the base (distal) of inner valve support 112. Snare 111 may retain the base near the distal end of positioner catheter 109.

Positioner catheter 109 may have sufficient stiffness to push implant 101 distally. Positioner catheter 109 may have sufficient flexibility to curve within implant 101. The curve may push outwardly (arrows) on a side of implant 101. Positioner catheter 109 may thus be used to push implant 101 toward annulus 119 and orient implant 101 at an angle relative to left atrium LA and valve annulus 119 that is appropriate for deployment of implant 101.

Bushing 113 may include a lumen through which delivery cable 105 may translate. Bushing 113 may include a lumen through which positioner catheter 109 may translate. Bushing 113 may be fixed to the distal end of pusher catheter 107. Pusher catheter 107 may thus be used to position bushing 113 within delivery catheter 115. Pusher catheter 107 may thus be used to position bushing 113 beyond the distal end of delivery catheter 115. Delivery catheter 115 may be configured to prevent bushing 113 from moving beyond the distal end of delivery catheter 115.

Delivery catheter 115 may be moved within sheath 116. In preparation for an implant procedure, implant 101 may be loaded into delivery catheter 115. Implant 101 may be delivered by advancing delivery catheter 115 out of sheath 116 and then out of delivery catheter 115. The relative positions of implant 101, delivery catheter 115 and sheath 116 may be coordinated to provide controlled expansion of implant 101 as it is delivered to a heart chamber and positioned within the heart chamber.

The distal end of delivery catheter 115 may be positioned distal an access hole in a septum. The distal end of delivery catheter 115 may be positioned in LA and valve annulus 119 for delivering a supplemental or replacement mitral valve. The distal end of delivery catheter 115 may be positioned in the right atrium for delivering a supplemental or replacement tricuspid valve. The distal end of delivery catheter 115 may be positioned in the inferior vena cava for delivering a supplemental or replacement tricuspid valve.

Figure 2:
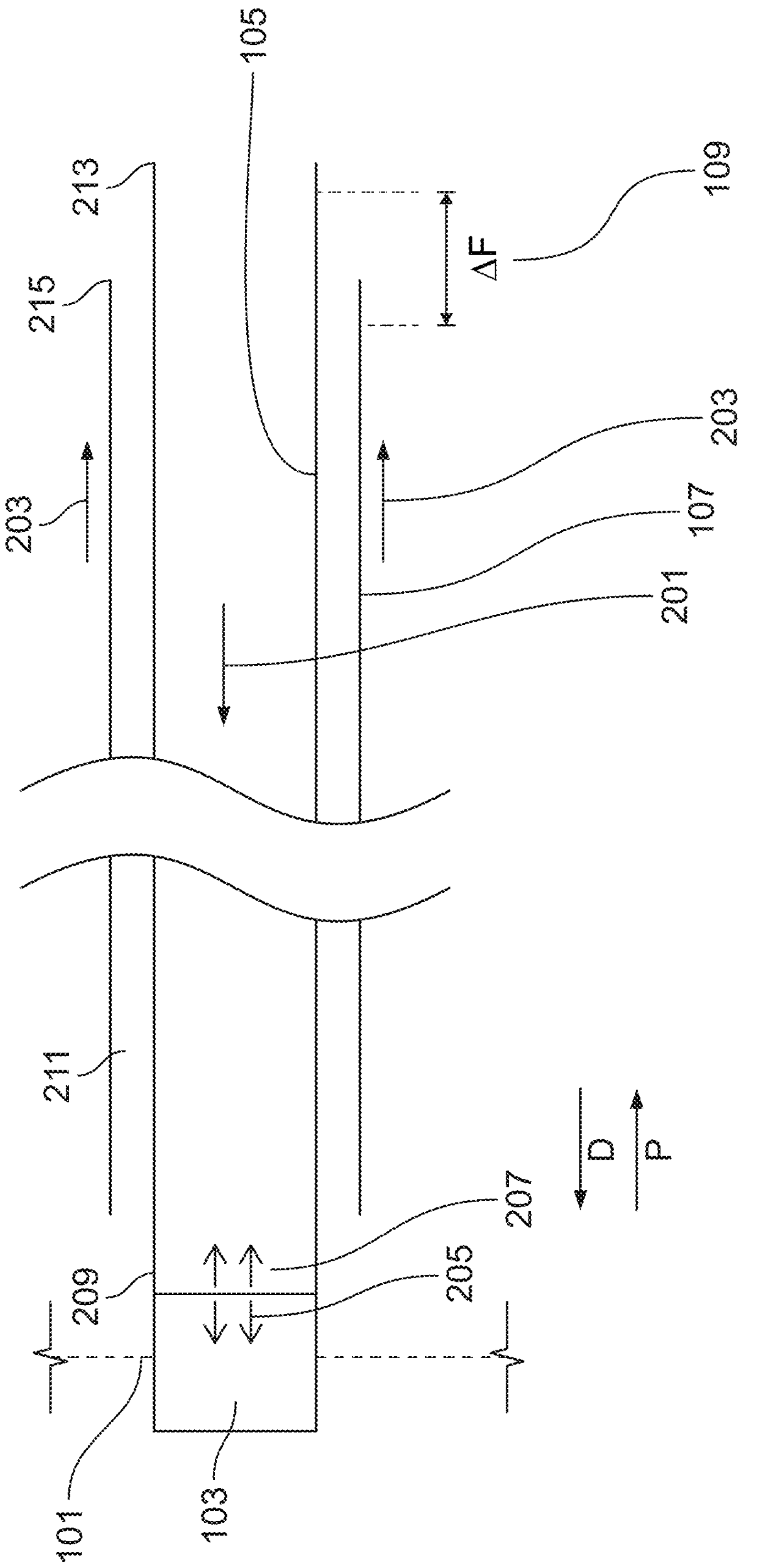
FIG. 2 shows schematically illustrative apparatus and methods in accordance with principles of the invention.

FIG. 2 shows schematically that implant 101 may include hub 103. Hub 103 may be removably coupled to distal end 209 of delivery cable 105. Delivery cable 105 may extend along lumen 211 of pusher catheter 107. Proximal end 213 of delivery cable 105 may be coupled to proximal end 215 of pusher catheter 107 via the force gauge (not shown). Delivery cable 105 and pusher catheter 107 may be movable in unison via the force gauge. A main handle (not shown) may advance in distal direction D or withdraw in proximal direction P pusher catheter 107. Advancing pusher catheter 107 may advance delivery cable 105 via the force gauge. Withdrawing pusher catheter 107 may withdraw delivery cable 105 via the force gauge.

Delivery cable 105 may manipulate implant 101. Manipulation of implant 101 may generate forces on one or more of implant 101, delivery cable 105 and pusher catheter 107. Differential force ΔF may be generated between delivery cable 105 and pusher catheter 107 during manipulation. The force gauge may measure differential force ΔF.

Withdrawing pusher catheter 107 may withdraw delivery cable 105. Withdrawing delivery cable 105 may withdraw implant 101. During the withdrawal, implant 101 may encounter an obstruction (not shown) such as an implant loading device, a delivery catheter, a delivery catheter edge, a bend in the delivery catheter, a delivery catheter interior wall, patient anatomy or the like. Force against the obstruction may generate force on implant 101. The obstruction may generate force 201 on delivery cable 105. Force 201 may be negligible or zero when there is no obstruction.

Pusher catheter 107, when at rest, may be held in place by the main handle. Withdrawing pusher catheter 107, e.g., via the main handle, may generate force 203 on pusher catheter 107.

Force 201 may contribute to differential force ΔF between delivery cable 105 and pusher catheter 107. Force 201 may contribute when pusher catheter 107 is held in place. Force 201 may contribute when pusher catheter 107 is moving. Force 203 may contribute to differential force ΔF when force 201 is present. It may be that in the absence of an obstruction, force 203 does not contribute to differential force ΔF when pusher catheter 107 moves in unison with delivery cable 105.

Forces commensurate or nearly commensurate with differential force ΔF may register as a compressive force across the force gauge. Forces commensurate or nearly commensurate with differential force ΔF may register as a tensile force across the force gauge. Differential force ΔF may act along some or all of the entire length of delivery cable 105. Differential force ΔF may act on hub 103. Differential force ΔF may act on pusher catheter 107 from its connection to the force gauge to where it is held by the main handle. Differential force ΔF may act on the connection between hub 103 and delivery cable 105. Force commensurate with differential force ΔF may be present as a tension between hub 103 and delivery cable 105. The tension may result from first force 205 and second force 207.

The predetermined failure region may include a failure strength. It may be necessary to assess implant 101 when the force gauge indicates a threshold force that is equal to or greater than a predetermined amount less than the failure strength.

Figure 3:
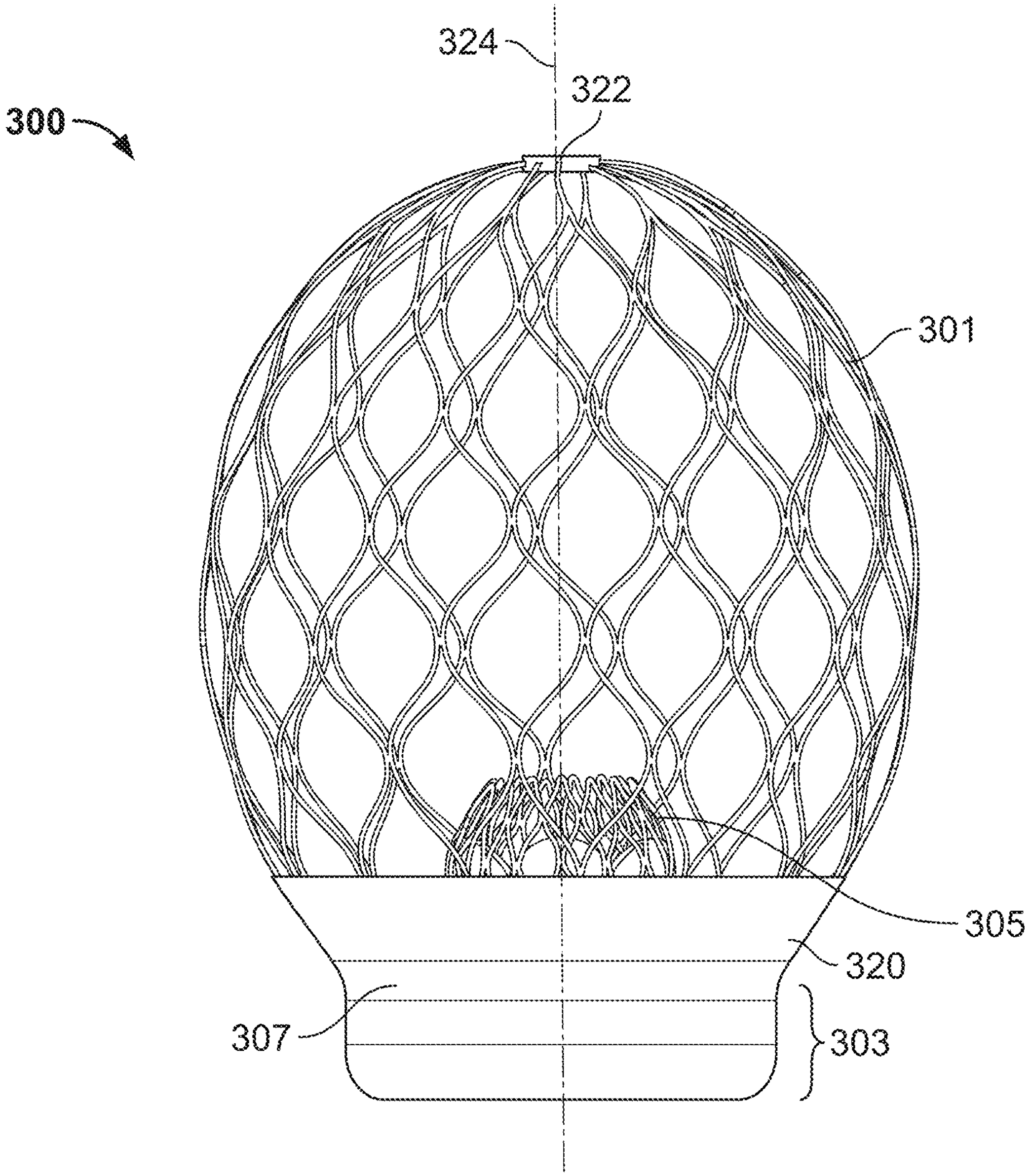
FIG. 3 shows illustrative apparatus in accordance with principles of the invention.

FIG. 3 shows illustrative implant 300. Axis 324 may be a central axis of implant 300. Implant 300 may include curved portion 301. Implant 300 may be formed from cells. Implant 300 may include annular ring 303. Annular ring 303 may be covered with covering 307. Bottom portion 320 of curved portion 301 may also be covered by covering 307. Annular ring 303 may extend away from curved portion 301.

Implant 300 may include a transition section at a bottom of implant 300. Implant 300 may include inner valve support 305. Implant 300 may include hub 322. Hub 322 may be positioned at a top of implant 300. Ends of cells of implant

300 may be captured in hub 322 and configured to rotate within hub 322 to enable implant 300 to collapse and expand. The ends of the cells may be the struts.

Figure 4:
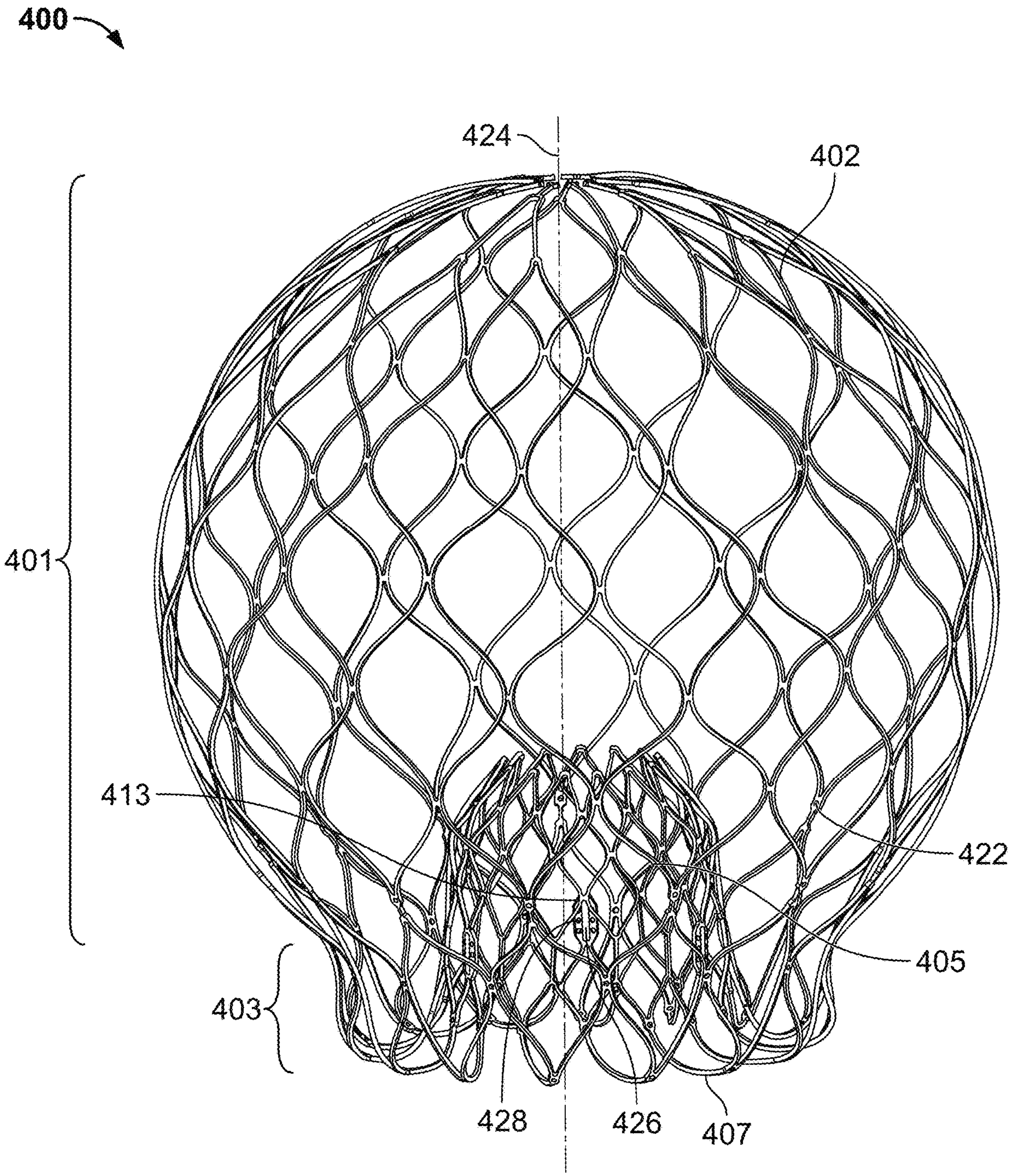
FIG. 4 shows illustrative apparatus in accordance with principles of the invention.

FIG. 4 shows illustrative implant 400. Axis 424 may be a central axis of implant 400.

Implant 400 may include curved portion 401. Implant 400 may be formed from cells 402. Implant 400 may include annular ring 403. Annular ring 403 may be covered with a covering (not shown). Annular ring 403 may extend away from curved portion 401.

Implant 400 may include transition section 407 and inner valve support 405. Implant 400 may include the hub (not shown) at a top of implant 400.

Cells of the implant may include opening 422 for suturing the covering to the implant. Inner valve support 405 may include a plurality of leaflet extension attachment features ("LEAF") 428 for securing the leaflets to LEAF 428. LEAF 428 may include slot 426 for receiving ends of adjacent leaflets and holes 413 for suturing the leaflets to LEAF 428.

Figure 5:
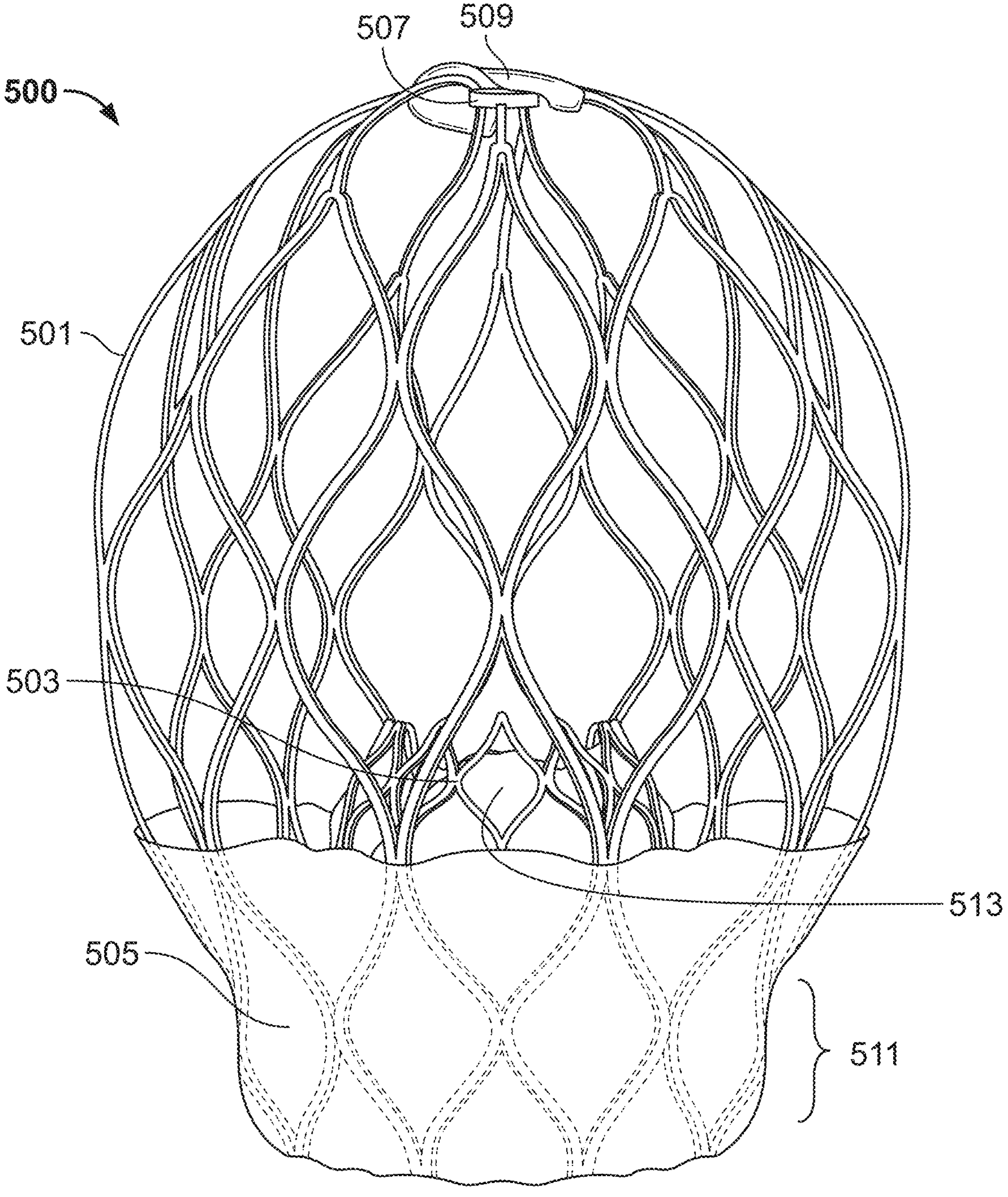
FIG. 5 shows illustrative apparatus in accordance with principles of the invention.

FIG. 5 shows illustrative implant 500. Implant 500 may include curved portion 501. Implant 500 may be formed from cells. Implant 500 may include annular ring 511. Annular ring 511 may be covered with covering 505. A bottom portion of curved portion 501 may also be covered by covering 505. Annular ring 511 may extend away from curved portion 501.

Implant 500 may include a transition section at a bottom of implant 500. Implant 500 may include inner valve support 503. Inner valve support may support leaflets 513.

Implant 500 may include hub 507. Hub 507 may be positioned at a top of implant 500. Ends of cells of implant 500 may be captured in hub 507 and configured to pivot within hub 507 to enable implant 500 to collapse and expand. The ends of the cells may be the struts. Implant 500 may include cover 509. Cover 509 may cover hub 507.

Figure 6:
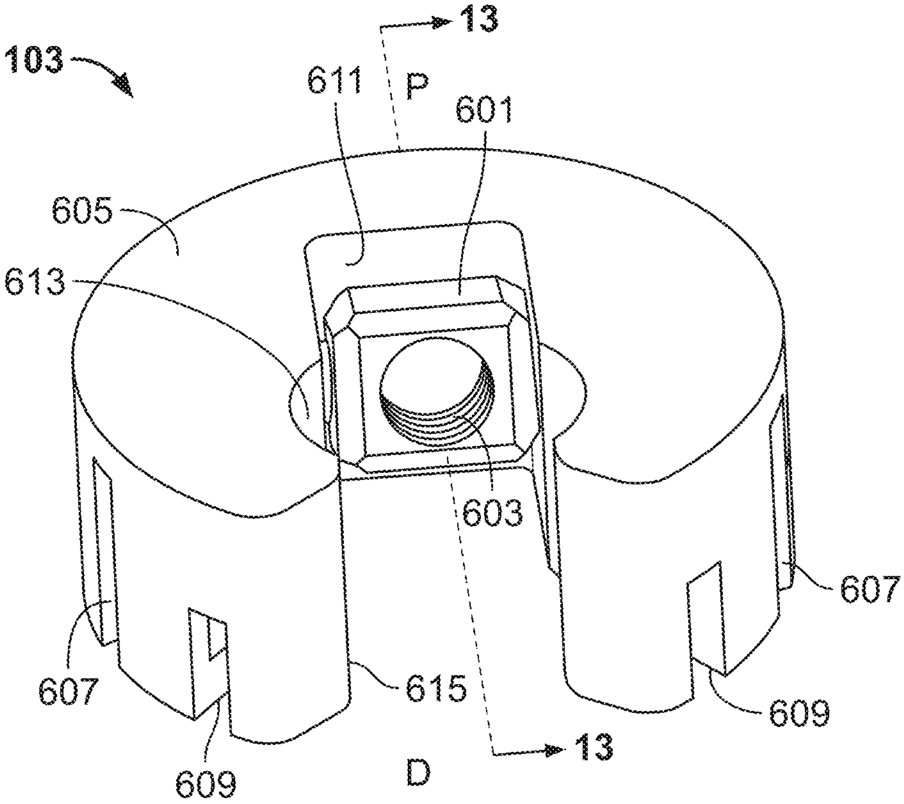
FIG. 6 shows illustrative apparatus in accordance with principles of the invention.

FIG. 6 shows a front view of hub 103. Hub 322 and hub 507 may have one or more features in common with hub 103. Hub 103 may include hinge block 605. Hub 103 may include swivel body 601. Swivel body 601 may define threaded interior 603. Threaded interior 603 may include threads. Threaded interior 603 may include female threads.

Hinge block 605 may define rectangular recess 611. Swivel body 601 may be disposed in rectangular recess 611. Swivel body 601 may be accessible through rectangular recess 611. Swivel body 601 may be rotatable within rectangular recess 611 with respect to hinge block 605. Hinge block 605 may define cylindrical cavity 613. Cylindrical cavity 613 may be shaped to receive the protrusion. Hinge block 605 may define flared opening 615. Flared opening 615 may be shaped to receive the positioner catheter.

Hub 103 may include slots 607 and 609. Slots 607 and 609 may be configured to accept ends of struts included in the implant, such as the struts that included in implant 101, implant 300, implant 400 and implant 500. Slots 607 and 609 may enable the ends of the struts to pivot within hinge block 605.

Figure 7:
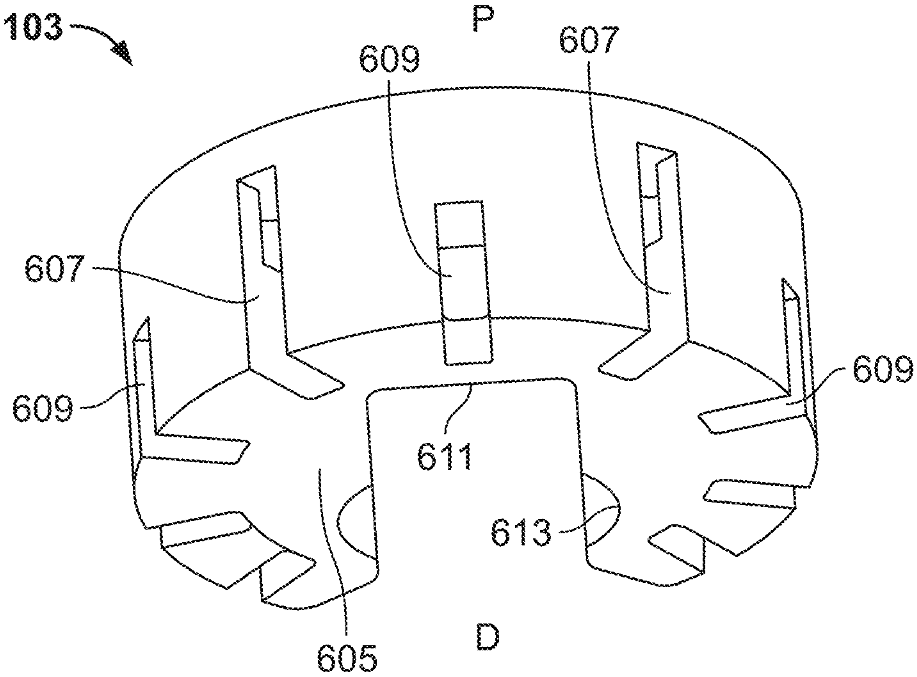
FIG. 7 shows illustrative apparatus in accordance with principles of the invention.

FIG. 7 shows a back view of hub 103.

Figure 8:
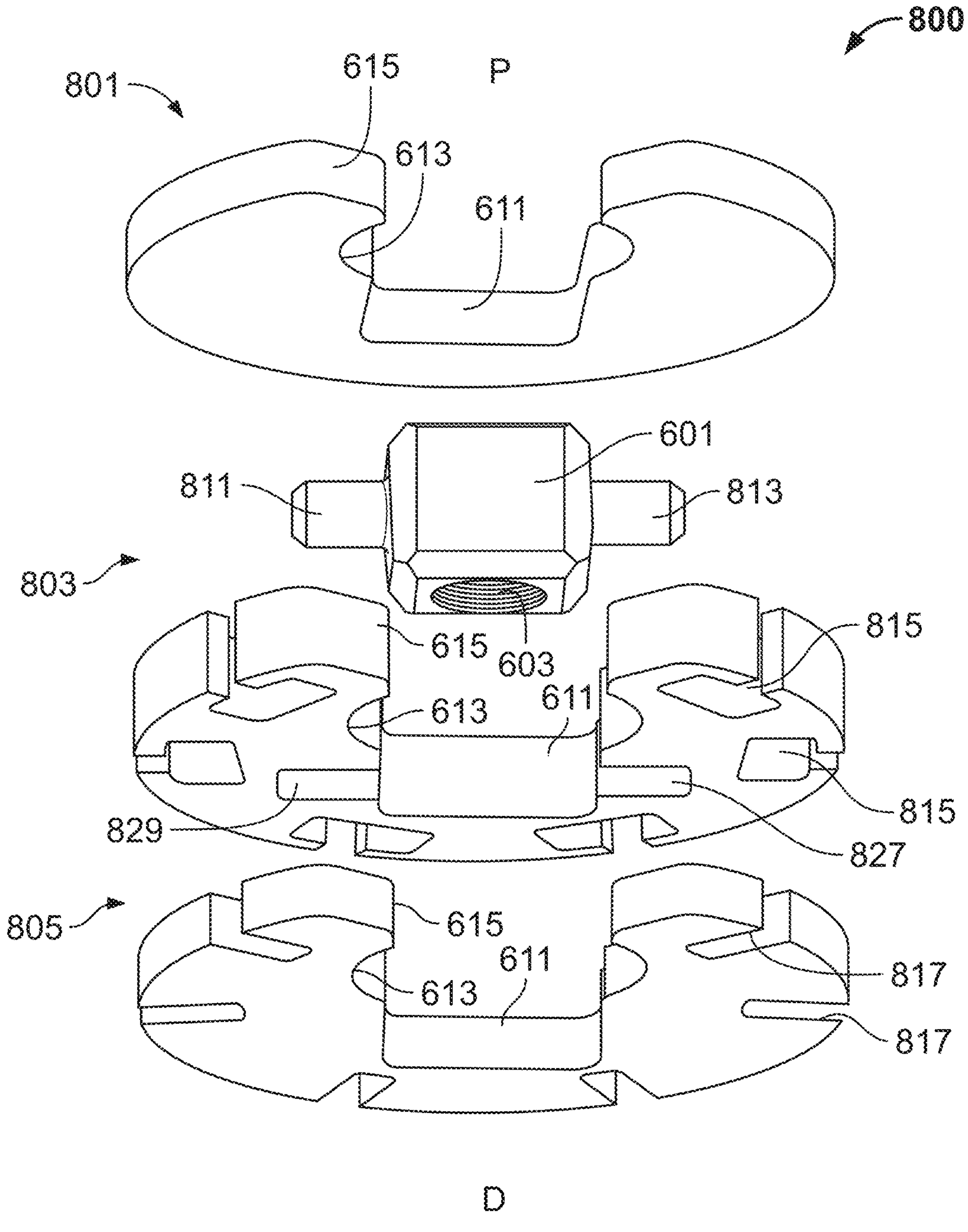
FIG. 8 shows illustrative apparatus in accordance with principles of the invention.

FIG. 8 shows an illustrative exploded view of hub 800. Hub 800 may have one or more features in common with hub 103. Hub 800 may include the hinge block. The hinge block may include top segment 801. The hinge block may include middle segment 803. The hinge block may include bottom segment 805. Hub 800 may include swivel body 601.

Top segment 801, middle segment 803 and bottom segment 805 may be discoidal. Each of top segment 801, middle segment 803 and bottom segment 805 may include an upper face, a bottom face and a thickness.

Middle segment 803 may include "T"-shaped slots 815. "T"-shaped slots 815 may be disposed circumferentially around middle segment 803. Each of "T"-shaped slots 815 may include a horizontal cutout. Each of "T"-shaped slots 815 may include a vertical cutout. The vertical cutout may extend perpendicularly from the horizontal cutout. The horizontal cutout may be shaped to receive a crossbar included in the end of each strut. The vertical cutout may be shaped to receive an arm extending from the crossbar include in the end of each strut.

Middle segment 803 may define rectangular recess 611. Middle segment 803 may define cylindrical cavity 613. Middle segment 803 may define flared opening 615. Middle segment 803 may include receptacle 827. Middle segment 803 may include receptacle 829. Receptacle 827 may be a straight slot that may receive swivel arm 813 of swivel body 601. Receptacle 829 may be a straight slot that may receive swivel arm 811 of swivel body 601. Receptacle 827 may extend from rectangular recess 611. Receptacle 829 may extend from rectangular recess 611. Receptacle 827 and receptacle 829 may extend colinearly away from each other. Receptacle 827 may extend in a first direction. Receptacle 829 may extend in a second direction.

Bottom segment 805 may include straight slots 817. Each of straight slots 817 may include a vertical cutout. Straight slots 817 may be disposed circumferentially around bottom segment 805. Each straight slot included in straight slots 817 may be aligned with a "T"-shaped slot included in "T"-shaped slots 815.

Bottom segment 805 may define rectangular recess 611. Bottom segment 805 may define cylindrical cavity 613. Bottom segment 805 may define flared opening 615.

Top segment 801 may include neither "T"-shaped slots nor straight slots. Top segment 801 may define rectangular recess 611. Top segment 801 may define cylindrical cavity 613. Top segment 801 may define flared opening 615.

The bottom face of top segment 801 may be fixedly attached to the top face of middle segment 803. The top face of bottom segment 805 may be fixedly attached to the bottom face of middle segment 803.

Top segment 801 may not include receptacles 827 and 829. Bottom segment 805 may not include receptacles 827 and 829. When the top segment 801 and bottom segment 805 are fixedly attached to middle segment 803, swivel body 601 may be trapped in receptacles 827 and 829. When swivel body 601 is trapped in receptacles 827 and 829, swivel arms 813 and 811 may be rotatable. Swivel arms 813 and 811 may be rotatable within receptacles 827 and 829. Top segment 801 and bottom segment 805 may prevent swivel body 601 from disengaging from the hinge block.

When the top segment 801 and bottom segment 805 are fixedly attached to middle segment 803, ends of struts may be captured in "T"-shaped slots 815. Top segment 801 and bottom segment 805 may prevent the ends of the struts from disengaging from the hinge block. Straight slots 817 included in bottom segment 805 may enable the ends of the struts to pivot. The horizontal cutout included in each "T"-shaped slot 815 may trap the crossbar at the end of each strut. The vertical cutout included in each "T"-shaped slot 815 and straight slot 817 may enable each strut to pivot within the hinge block. Each strut may pivot from a first position to a second position. The first position may correspond to a constrained state of the implant. The second position may correspond to a relaxed state of the implant.

Figure 9:
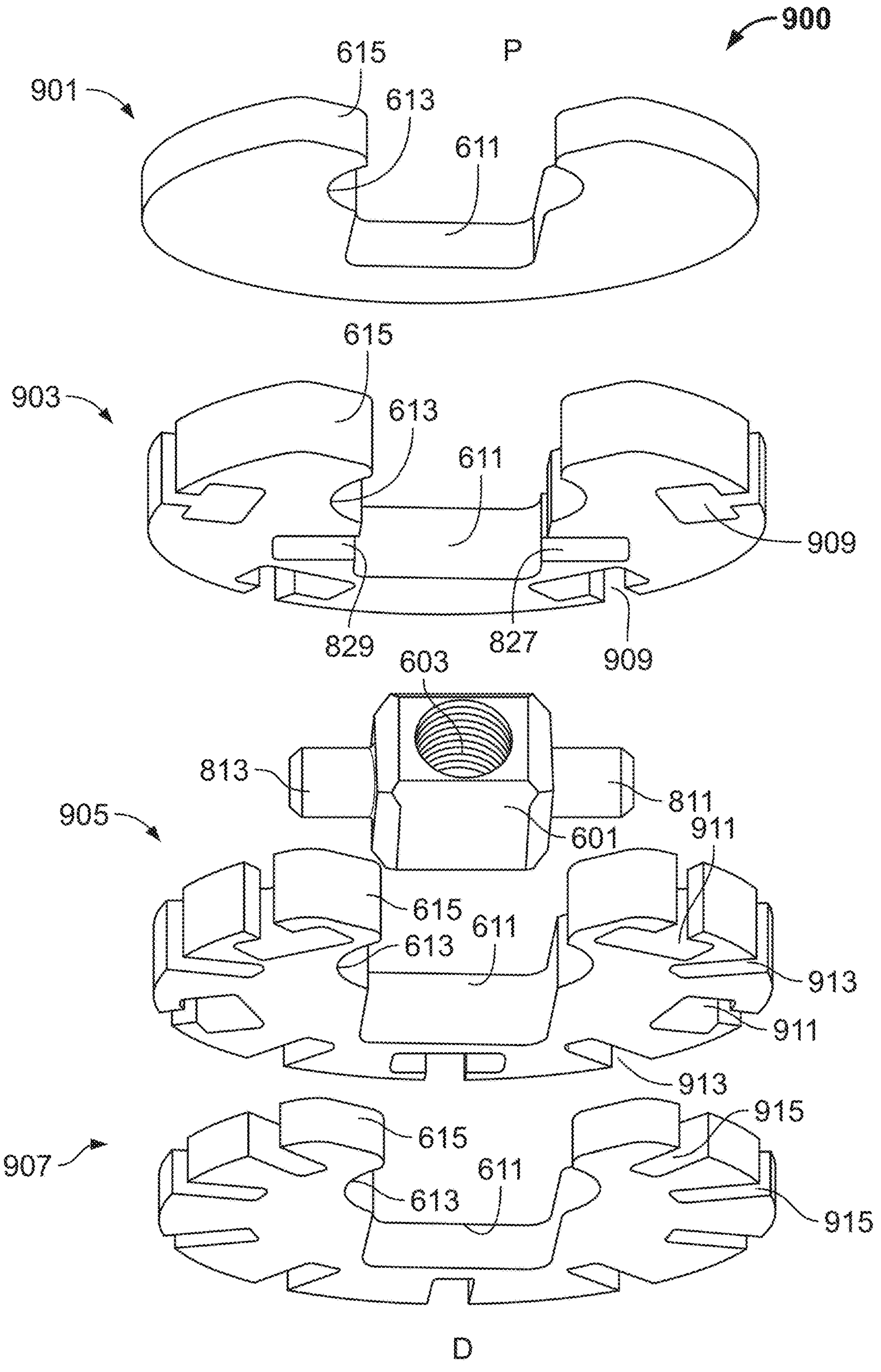
FIG. 9 shows illustrative apparatus in accordance with principles of the invention.

FIG. 9 shows an illustrative exploded view of hub 900. Hub 900 may have one or more features in common with one or more of hub 103 and hub 800. Hub 800 may be used for an implant having a first cell pattern. The cell pattern may be a 8, 10, 12, 14, 15, 16, 18, or any other suitable cell, cell pattern. Hub 900 may be used for an implant having a second cell pattern. The second cell pattern may be different from the first cell pattern. The second cell pattern may have more cells than the first cell pattern. The second cell pattern may have less cells than the first cell pattern. The second cell pattern may be the first cell pattern.

Hub 900 may include the hinge block. The hinge block may include top segment 901. The hinge block may include upper middle segment 903. The hinge block may include lower middle segment 905. The hinge block may include bottom segment 907. Hub 900 may include swivel body 601.

Top segment 901, upper middle segment 903, lower middle segment 905 and bottom segment 907 may be discoidal. Each of top segment 901, upper middle segment 903, lower middle segment 905 and bottom segment 907 may include an upper face, a bottom face and a thickness.

Upper middle segment 903 may include "T"-shaped slots 909. "T"-shaped slots 909 may be disposed circumferentially around upper middle segment 903. Each of "T"-shaped slots 909 may include a horizontal cutout. Each of "T"-shaped slots 909 may include a vertical cutout. The vertical cutout may extend perpendicularly from the horizontal cutout. The horizontal cutout may be shaped to receive a crossbar included in the end of each strut. The vertical cutout may be shaped to receive an arm extending from the crossbar include in the end of each strut.

Upper middle segment 903 may define rectangular recess 611. Upper middle segment 903 may define cylindrical cavity 613. Upper middle segment 903 may define flared opening 615. Upper middle segment 903 may include receptacle 827. Upper middle segment 903 may include receptacle 829.

Lower middle segment 905 may include alternating "T"-shaped slots 911 and straight slots 913. Alternating "T"-shaped slots 911 and straight slots 913 may be disposed circumferentially around lower middle segment 905. Each of "T"-shaped slots 911 may include a horizontal cutout. Each of T"-shaped slots 911 may include a vertical cutout. The vertical cutout may extend perpendicularly from the horizontal cutout. The horizontal cutout may be shaped to receive a crossbar included in the end of each strut. The vertical cutout may be shaped to receive an arm extending from the crossbar include in the end of each strut.

Each of straight slots 913 may include a vertical cutout. Each straight slot included in straight slots 913 may be aligned with a "T"-shaped slot included in "T"-shaped slots 909.

Lower middle segment 905 may define rectangular recess 611. Lower middle segment 905 may define cylindrical cavity 613. Lower middle segment 905 may define flared opening 615.

Bottom segment 907 may include straight slots 915. Each of straight slots 915 may include a vertical cutout. Straight slots 915 may be disposed circumferentially around bottom segment 907. Each straight slot included in straight slots 915 may be aligned with either "T"-shaped slot included in "T"-shaped slots 911 or a straight slot included in straight slots 913.

Bottom segment 907 may define rectangular recess 611. Bottom segment 907 may define cylindrical cavity 613. Bottom segment 907 may define flared opening 615.

Top segment 901 may include neither "T"-shaped slots nor straight slots. Top segment 901 may define rectangular recess 611. Top segment 901 may define cylindrical cavity 613. Top segment 901 may define flared opening 615.

The bottom face of top segment 901 may be fixedly attached to the top face of upper middle segment 903. The bottom face of upper middle segment 903 may be fixedly attached to the upper face of lower middle segment 905. The top face of bottom segment 907 may be fixedly attached to the bottom face of lower middle segment 905.

Top segment 901 may not include receptacles 827 and 829. Lower middle segment 905 may not include receptacles 827 and 829. Bottom segment 907 may not include receptacles 827 and 829. When the top segment 901 and lower middle segment 905 are fixedly attached to upper middle segment 903, swivel body 601 may be trapped in receptacles 827 and 829. Top segment 901 and lower middle segment 905 may prevent swivel body 601 from disengaging from the hinge block.

When the top segment 901 and bottom segment 907 are fixedly attached to upper middle segment 903 and lower middle segment 905, ends of the struts may be captured in "T"-shaped slots 909 and "T"-shaped slots 911. Top segment 901 and bottom segment 907 may prevent the ends of the struts from disengaging from the hinge block. Straight slots 913 and 915 may enable the ends of the struts to pivot. The horizontal cutout included in each "T"-shaped slots 909 and 911 may trap the crossbar included in the end of each strut. The vertical cutout included in each of "T"-shaped slots 909 and 911 and straight slots 913 and 915 may enable each strut to pivot within the hinge block.

Figure 10:
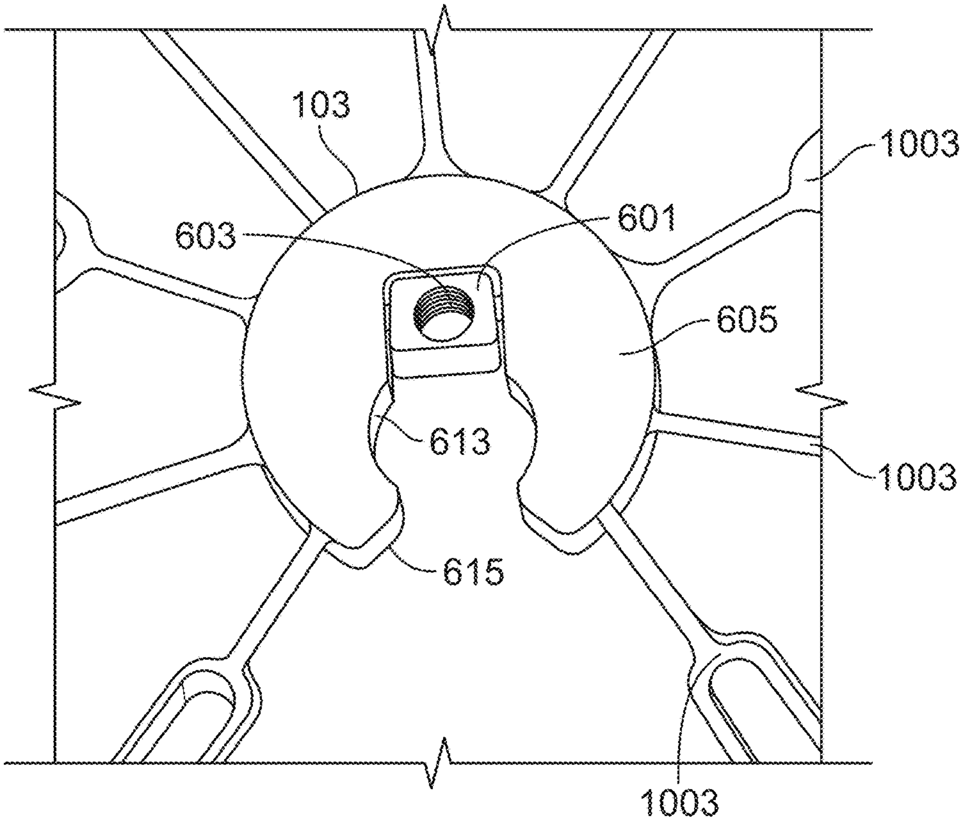
FIG. 10 shows illustrative apparatus in accordance with principles of the invention.

FIG. 10 shows a perspective view of hub 103. Hub 103 may capture struts 1003. Hub 103 may capture struts 1003. Struts 1003 may be included in the implant, such as struts included in implant 101, implant 300, implant 400 and implant 500.

Figure 11:
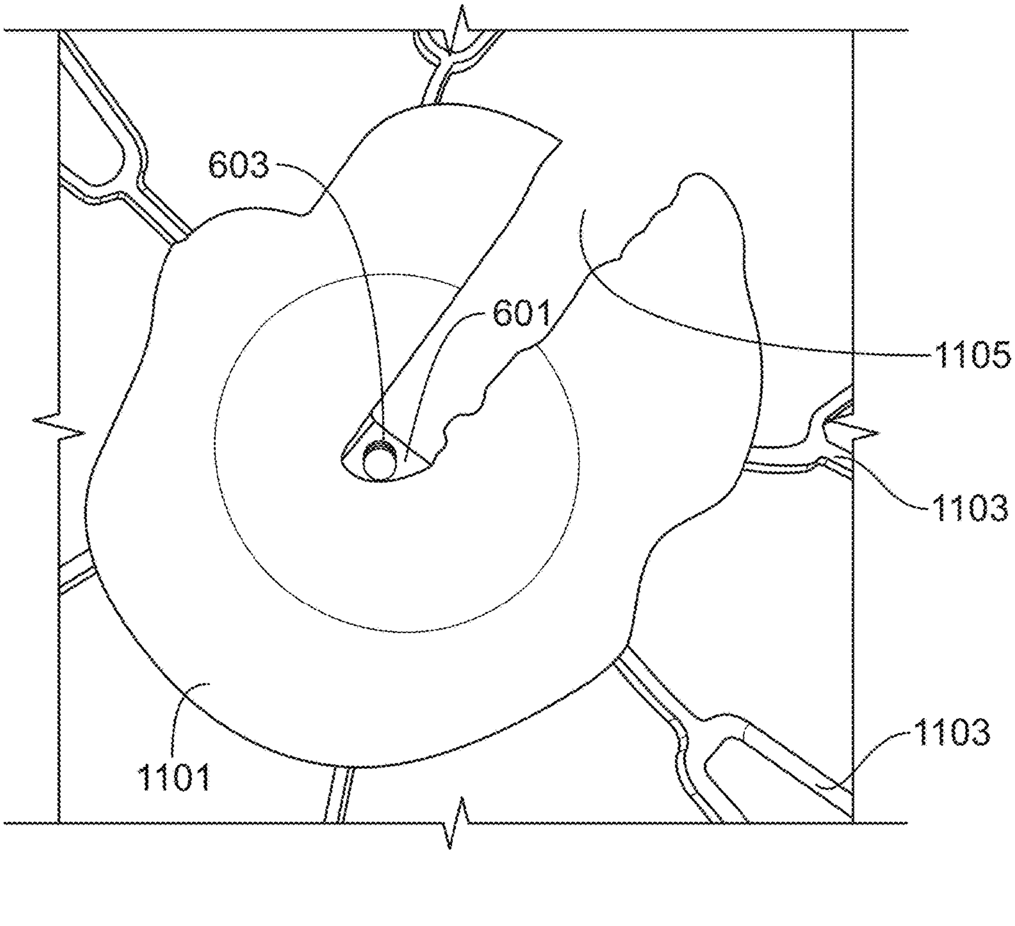
FIG. 11 shows illustrative apparatus in accordance with principles of the invention.

FIG. 11 shows a perspective drawing of hub 103 with hub cover 1101. Hub 103 may capture struts 1103. Hub cover 1101 may be disposed on top of hub 103. Hub cover 509 may have one or more features in common with hub cover 1101.

Hub cover 1101 may include a fabric. Hub cover 1101 may include a slit. The slit may form opening 1105 in hub cover 1101. Opening 1105 may provide access to swivel body 601 even when hub cover 1101 is disposed on hub 103. The delivery cable may extend through opening 1105 to gain access to threads 603 of swivel body 601 delivery cable 105.

Figure 12:
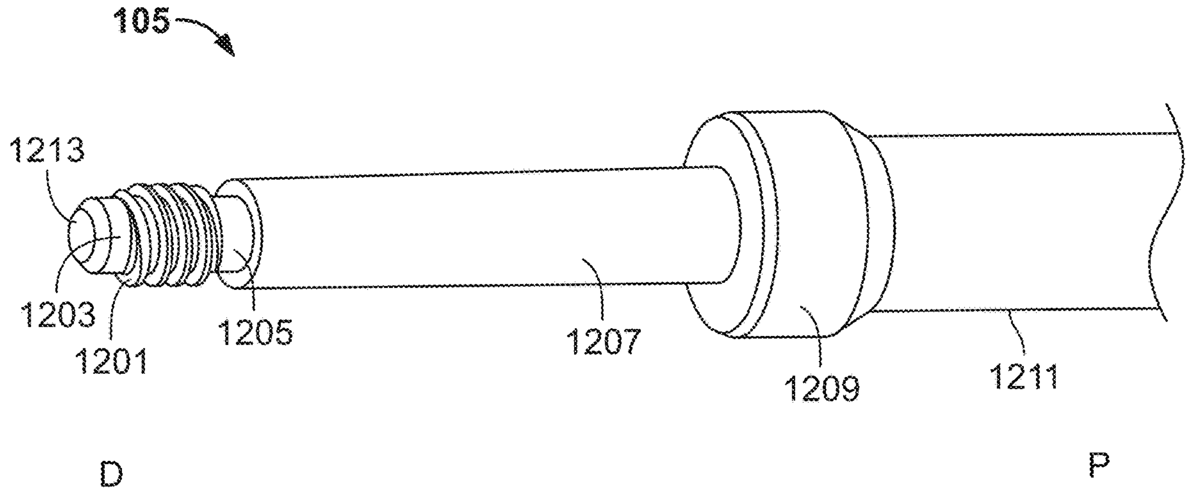
FIG. 12 shows illustrative apparatus in accordance with principles of the invention.

FIG. 12 shows a portion of delivery cable 105.

Delivery cable 105 may include threads 1201 and tip 1203. Tip 1203 may include end 1213 of delivery cable 105. The first segment may include threads 1201 and tip 1203. The first segment may include threads 1201.

Delivery cable 105 may include neck 1205. The second segment may include neck 1205. Delivery cable may include cylindrical body 1207, cylindrical body 1209 and cylindrical body 1211. Cylindrical bodies 1207, 1209 and 1211 may be included in the third segment. The third segment may extend between neck 1205 and a proximal end of delivery cable 105.

Cylindrical bodies 1207, 1209 and 1211 may each define different outer diameters. In some embodiments, one or more of cylindrical bodies 1207, 1209 and 1211 may have the same outer diameter.

The second segment may have a failure strength that is less than a failure strength of the first segment and the second segment. The second segment may have a failure strength that is less than a failure strength of a remaining portion of delivery cable 105.

Figure 13:
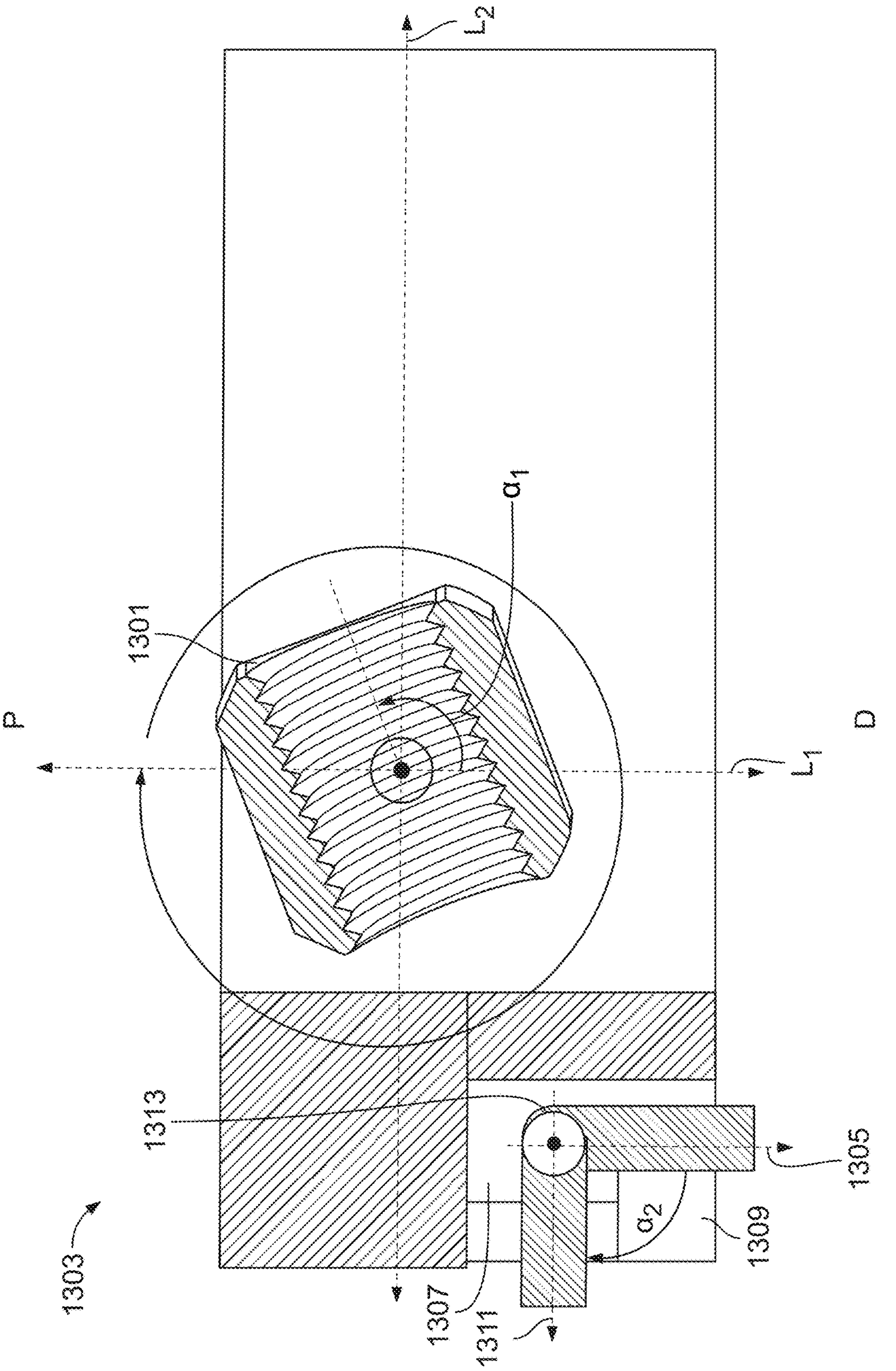
FIG. 13 shows a partial cross-section taken along view lines 13-13 (shown in FIG. 6)

FIG. 13 shows a cross-sectional view of hub 1303. Hub 1303 may have one or more features in common with hub 103. Hub 1303 may include swivel body 1301. Swivel body 1301 may have one or more features in common with swivel body 601.

Axis $L_1$ may be a central axis of hub 1303. Axis $L_2$ may be a horizontal axis of hub 1303.

Hub 1303 may define "T"-shaped slot 1307. "T"-shaped slot 1307 may have one or more features in common with one or more of "T"-shaped slots 815, 909 and 911. Hub 1303 may define straight slot 1309. Straight slot 1309 may have one or more features in common with straight slots 817, 913 and 915.

Hub 1303 may be configured to capture strut 1313. Strut 1313 may be captured by "T"-shaped slot 1307 and straight slot 1309. Strut 1313 may be pivotable within "T"-shaped slot 1307 and straight slot 1309. Strut 1313 may be pivotable from position 1305 to position 1311. Position 1305 may correspond to a position of strut 1313 when the implant is in a constrained configuration. The constrained configuration may include when the implant is in a compressed state. Position 1311 may correspond to a position of strut 1313 when the implant is in a relaxed configuration. The relaxed configuration may include when the implant is in an expanded state.

Pivoting from position 1305 to position 1311 may define angle $\alpha_2$. Angle $\alpha_2$ may define a reference angle relative to axis $L_2$.

Swivel body 1301 may be rotated relative to axis $L_2$. Swivel body 1301 may be rotated relative to axis $L_1$. Swivel body 1301 may be rotated at angle $\alpha_1$. Swivel body 1301 may be rotated through the reference angle. Angle $\alpha_1$ may include and may be greater than angle $\alpha_2$.

Figure 14A:
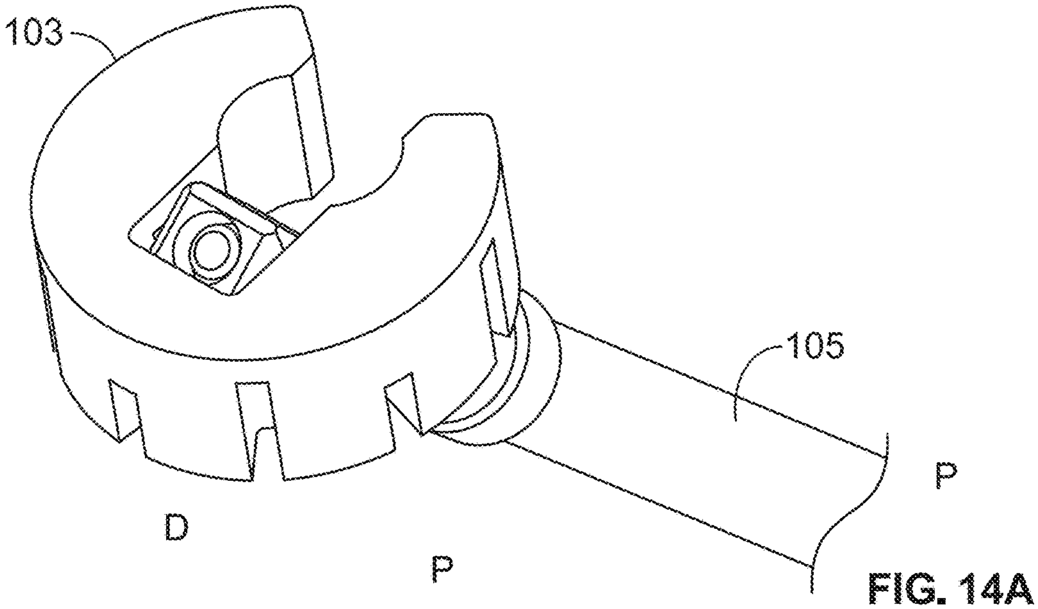
FIG. 14A shows illustrative apparatus and methods in accordance with principles of the invention.

FIG. 14A shows a view of hub 103 connected to delivery cable 105, when delivery cable 105 is in a rotated position. In a rotated position, delivery cable 105 may be connected to hub 103 at angle defined by an intersection between a hub longitudinal axis and a delivery cable longitudinal axis. The angle may be 90°. The angle may be less than 90°. The angle may be greater than 90°.

Figure 14B:
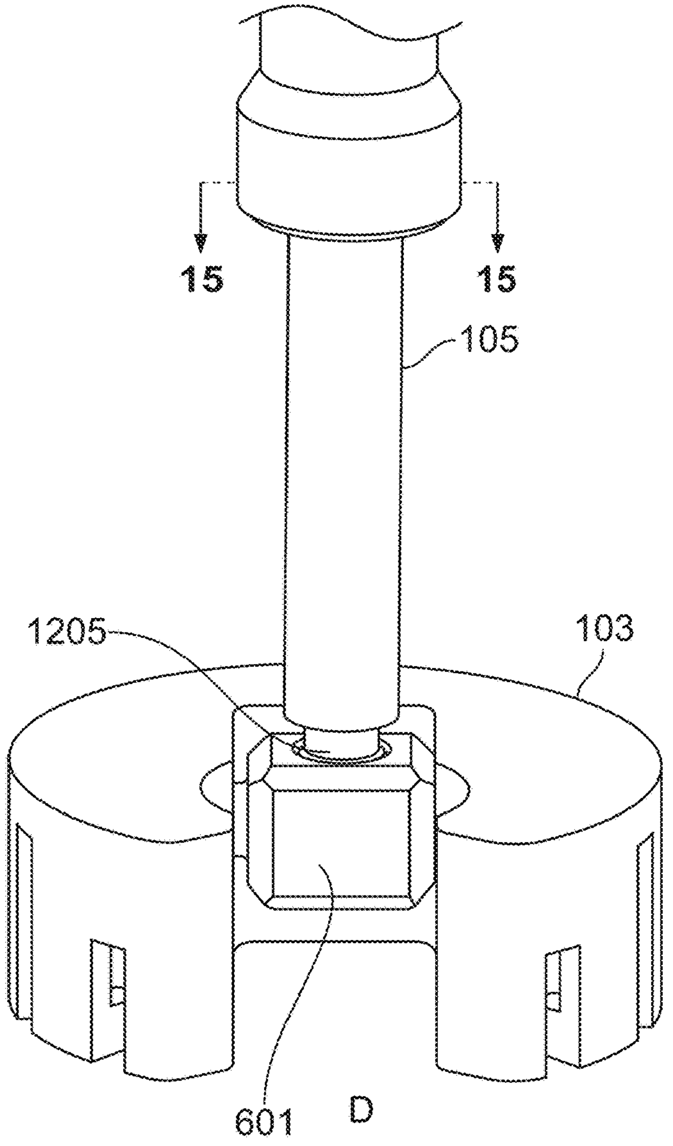
FIG. 14B shows illustrative apparatus and methods in accordance with principles of the invention.

FIG. 14B shows a view of hub 103 connected to delivery cable 105, when delivery cable 105 is in a non-rotated position. Neck 1205 is shown extending away from swivel body 601.

Figure 15:
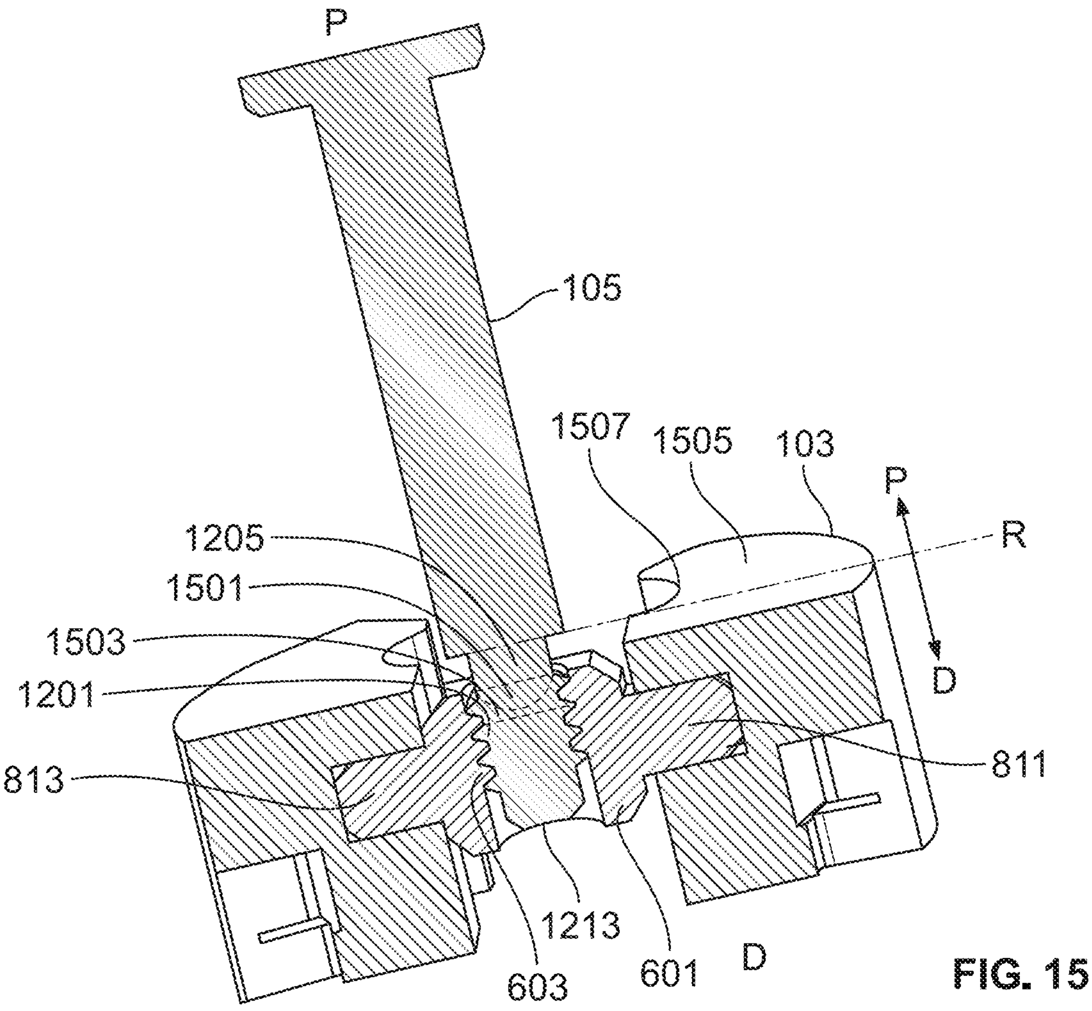
FIG. 15 shows a partial cross-section taken along view lines 15-15 (shown in FIG. 14B)

FIG. 15 shows a partial cross-sectional view of hub 103 connected to delivery cable 105 when delivery cable 105 is in a non-rotated position.

FIG. 15 shows illustrative regions that may be the predetermined failure region. A region extending between neck 1205 and end 1213 may be the predetermined failure region. Neck 1205 may be the predetermined failure region. Region 1501 may be the predetermined failure region. Region 1503 may be the predetermined failure region. Two or more of neck 1205, region 1501 and region 1503 may be the predetermined failure region.

A proximal end of neck 1205 may be the failure surface. A distal end of neck 1205 may be the failure surface. A volume extending between the proximal and distal ends of neck 1205 may be the predetermined failure region.

Upper surface 1505 of hub 103 may have rim 1507. The failure surface may be at the same level or distal of position R of rim 1507.

The failure surface may be no higher than a plane extending across upper surface 1505 of hub 103.

Figure 16:
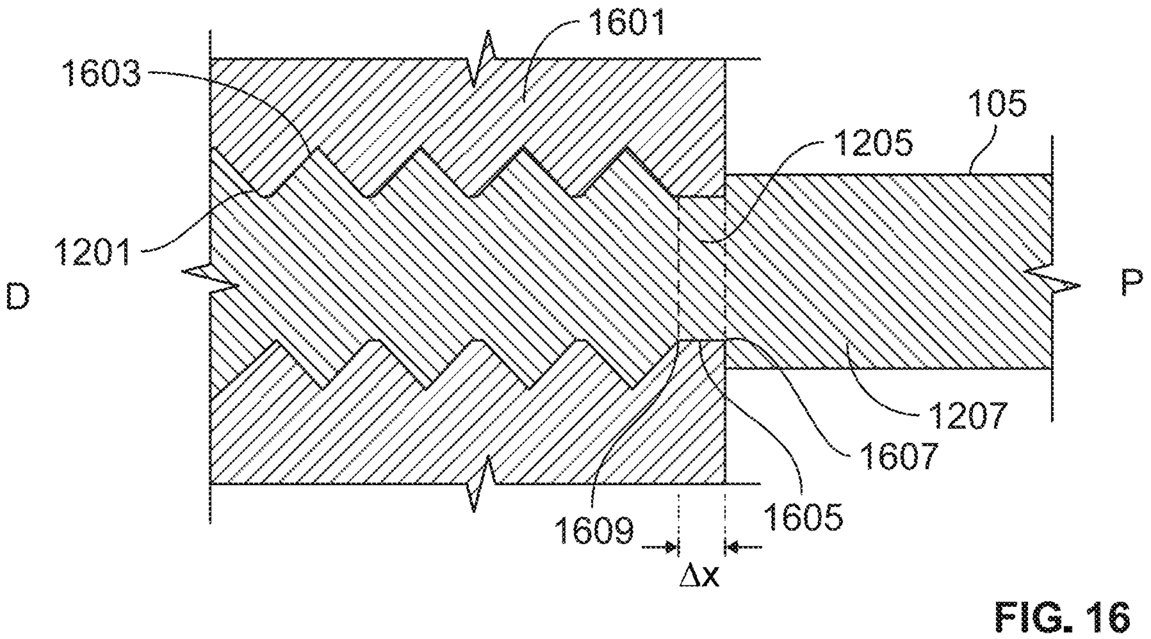
FIG. 16 shows schematically illustrative apparatus and methods in accordance with principles of the invention.

FIG. 16 shows a cross-sectional view of illustrative delivery cable 105 engaged with swivel body 1601. Swivel body 1601 may have one or more features in common with swivel body 601.

An interior of swivel body 1601 may include threads 1603 and non-threaded region 1605. Non-threaded region 1605 may have a length less than or equal to a length of neck 1205. Neck 1205 may have a length $\Delta x$. When threads 1201 are engaged with threads 1603, neck 1205 may be positioned in non-threaded surface 1605.

When neck 1205 is positioned in non-threaded surface 1605, a failure surface of delivery cable 105 may be at location 1607. Location 1607 may be a location where cylindrical body 1207 of delivery cable 105 contacts or is near an upper surface of swivel body 1601.

When neck 1205 is positioned in non-threaded surface 1605, a failure surface of delivery cable 105 may be at location 1609.

When neck 1205 is positioned in non-threaded surface 1605, a failure surface of delivery cable 105 may be within neck 1205.

The predetermined failure region may be neck 1205. The predetermined failure region may extend between neck 1205 and tip 1213. The predetermined failure region may extend between location 1609 and tip 1213.

Figure 17:
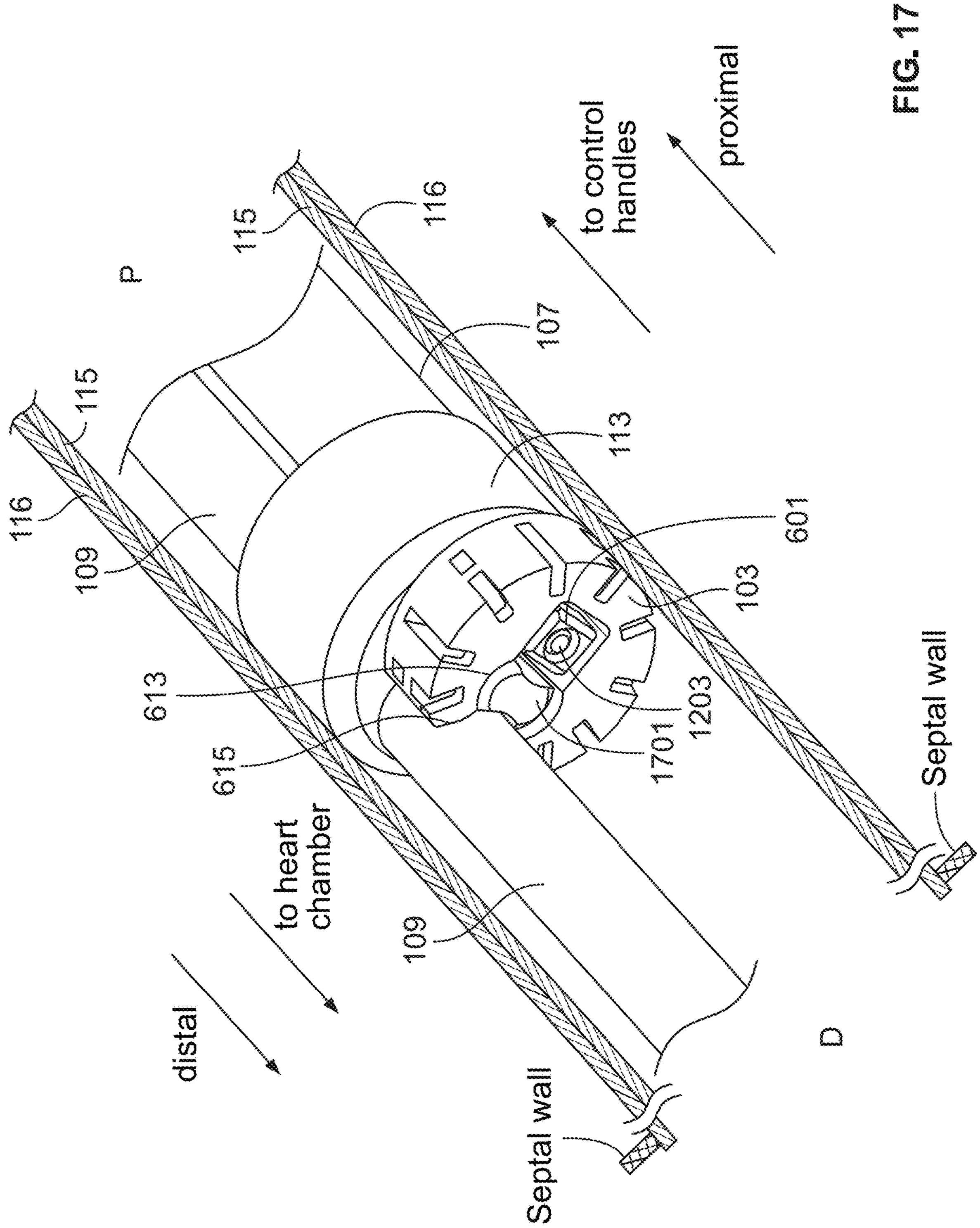
FIG. 17 shows illustrative apparatus and methods in accordance with principles of the invention.

FIG. 17 shows a partial cross-sectional view of illustrative apparatus. In FIG. 17, bushing 113 may be positioned in delivery catheter 115. Delivery catheter 115 is within sheath 116. Bushing 113 is mounted on the distal end of pusher catheter 107. Positioner catheter 109 extends through bushing 113.

Hub 103 (implant 101 not shown) is seated on bushing 113. Bushing 113 may include protrusion 1701, which is shown extending distally through hub 103. Tip 1203 of delivery cable 105 (extending through pusher catheter 107) is engaged with swivel block 601 of hub 103. Distal advancement of delivery cable 105 may advance hub 103 distally away from bushing 113. When hub 103 is positioned distally of bushing 113, proximal motion of delivery cable 105 may draw hub 103 into a predetermined keyed position with bushing 113. Cylindrical cavity 613 may engage with protrusion 1701 to guide hub 103 into the keyed position. Hub 103 may include flared opening 615. Flared opening 615 may be formed to conform to the outer diameter of positioner catheter 109. The conformance may orient hub 103 relative to bushing 113 when hub 103 is drawn into the keyed position. One or both of the conformance and protrusion 1701 may reduce or prevent axial rotation of hub 103 relative to bushing 113.

Figure 18:
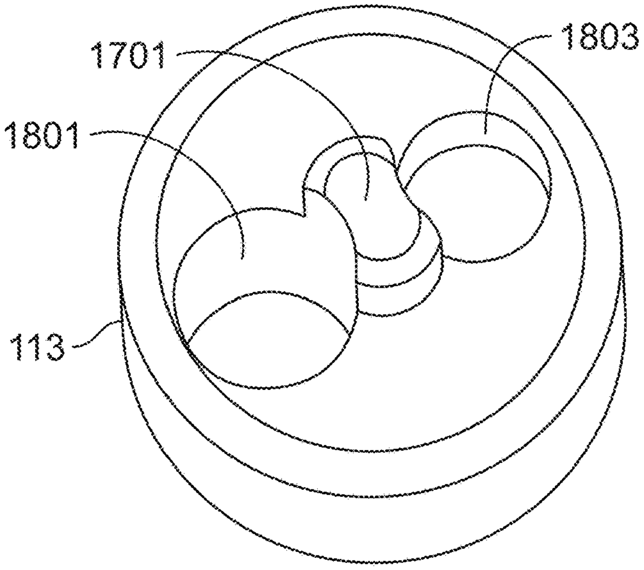
FIG. 18 shows illustrative apparatus in accordance with principles of the invention.
Figure 19:
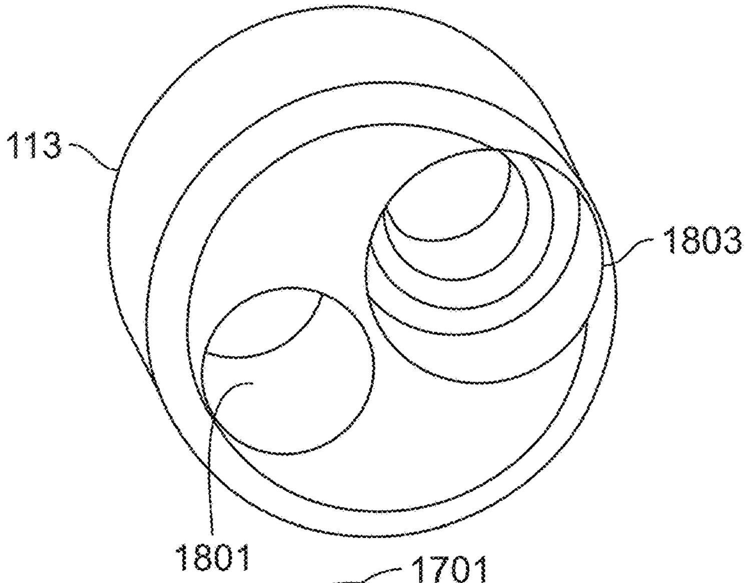
FIG. 19 shows illustrative apparatus in accordance with principles of the invention.

FIG. 18 shows a top view of bushing 113. Bushing 113 defines first bore 1803 and second bore 1801. Bushing 113 includes protrusion 1701. When the implant is drawn towards bushing 113, protrusion 1701 may guide the implant to the keyed position on bushing 113. FIG. 19 shows a bottom view of bushing 113.

Figure 20:
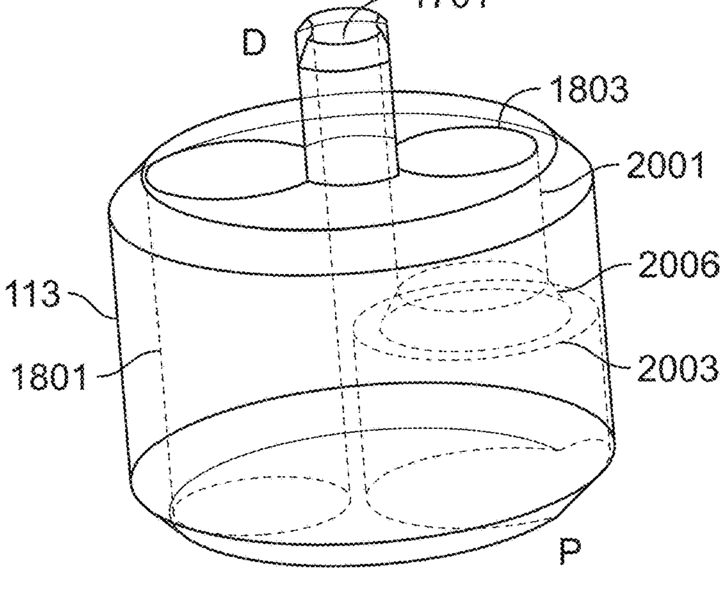
FIG. 20 shows illustrative apparatus in accordance with principles of the invention.

FIG. 20 shows a view of bores 1803 and 1801 extending through bushing 113. Bore 1801 have a constant cross-section along a length of bore 1801. Bore 1801 may be cylindrical. Bore 1801 may receive the positioner catheter. Bore 1801 may be smooth to allow for the positioner catheter to be in sliding engagement with bore 1801.

Bore 1803 may define first cylindrical segment 2001, second tapered segment 2006 and third cylindrical segment 2003. The pusher catheter may be fixedly coupled to third cylindrical segment 2003. The pusher catheter may be fixedly coupled to second tapered segment 2006.

The delivery cable may be in sliding engagement with first cylindrical segment 2001. The delivery cable may be in sliding engagement with bore 1803. The pusher catheter may have an inner diameter equal to a diameter of first cylindrical segment 2001.

Figure 21:
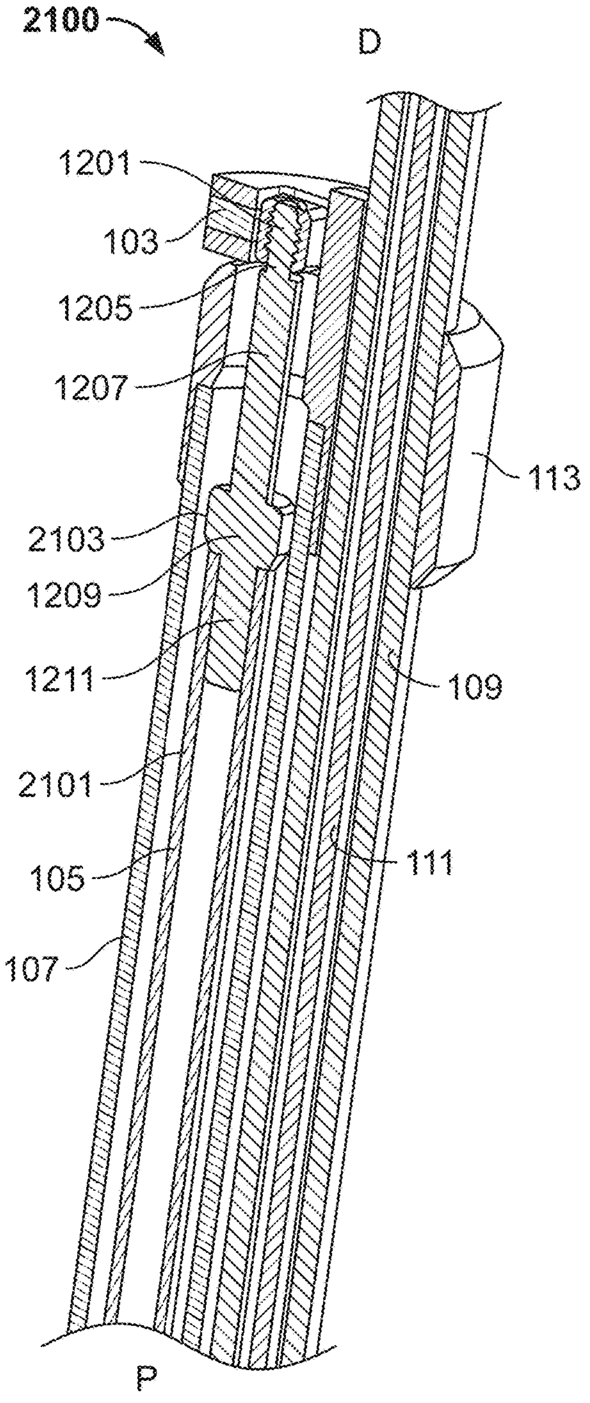
FIG. 21 shows illustrative apparatus and methods in accordance with principles of the invention.

FIG. 21 shows an illustrative partial cross-sectional view of apparatus 2100. FIG. 21 may show apparatus 2100 configured for loading the implant into the delivery catheter. FIG. 21 may show apparatus 2100 configured for deployment of implant 101 through the delivery catheter and into the heart chamber.

Delivery cable 105 may include torque wire 2101 and shaft 2103. Torque wire 2101 may be hollow. Torque wire 2101 may include a coil. Torque wire 2101 may be metal. Torque wire 2101 may be welded to shaft 2103. Shaft 2103 may be pressed fit into torque wire 2101. Shaft 2103 may include threads 1201, neck 1205, and cylindrical bodies 1207, 1209 and 1211. Hub 103 (implant 101 not shown) may be threadedly engaged with the threads 1201. Hub 103 may be seated on bushing 113.

Pusher catheter 107 be fixed to bushing 113. Pusher catheter 107 may be fixed to bushing such that pusher catheter terminates within bushing 113. Positioner catheter 109 and snare 111 may extend past bushing 113.

Figure 22:
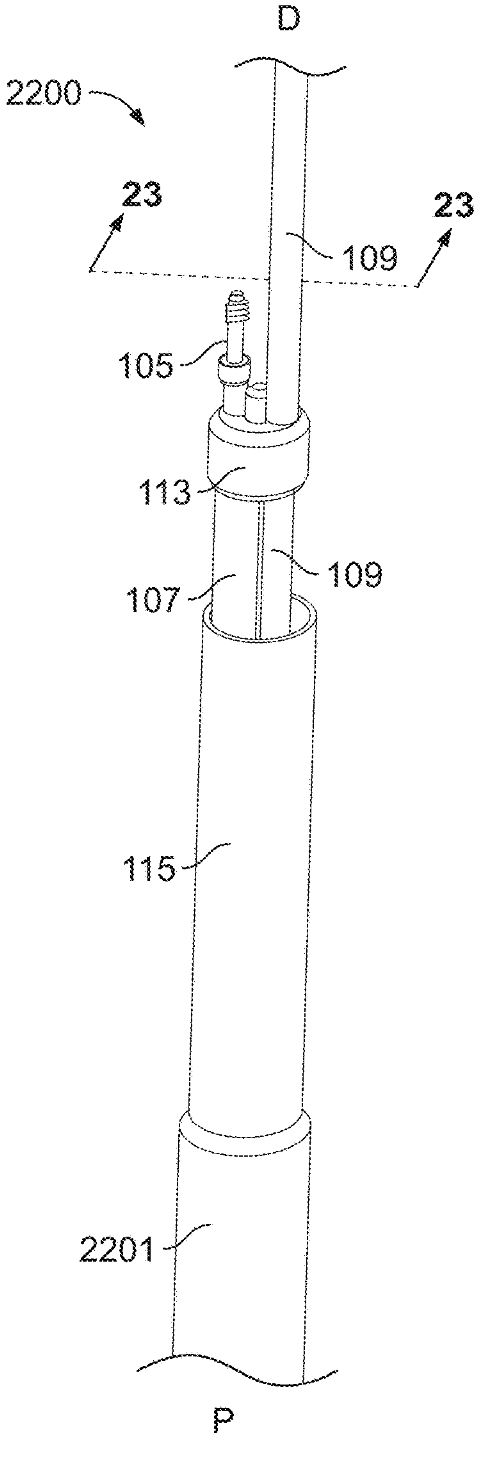
FIG. 22 shows illustrative apparatus and methods in accordance with principles of the invention.

FIG. 22 shows an illustrative view of apparatus 2200. Apparatus 2200 may be configured for partial deployment of implant 101 in the heart chamber. Delivery catheter may be advanced past sheath 2201. Bushing 113 may be advanced away from delivery catheter 115. Delivery cable 105 may be slightly extended past bushing 113 to disengage implant 101 from bushing 113 and to begin the positioning of the hub of the implant in the heart chamber.

Figure 23:
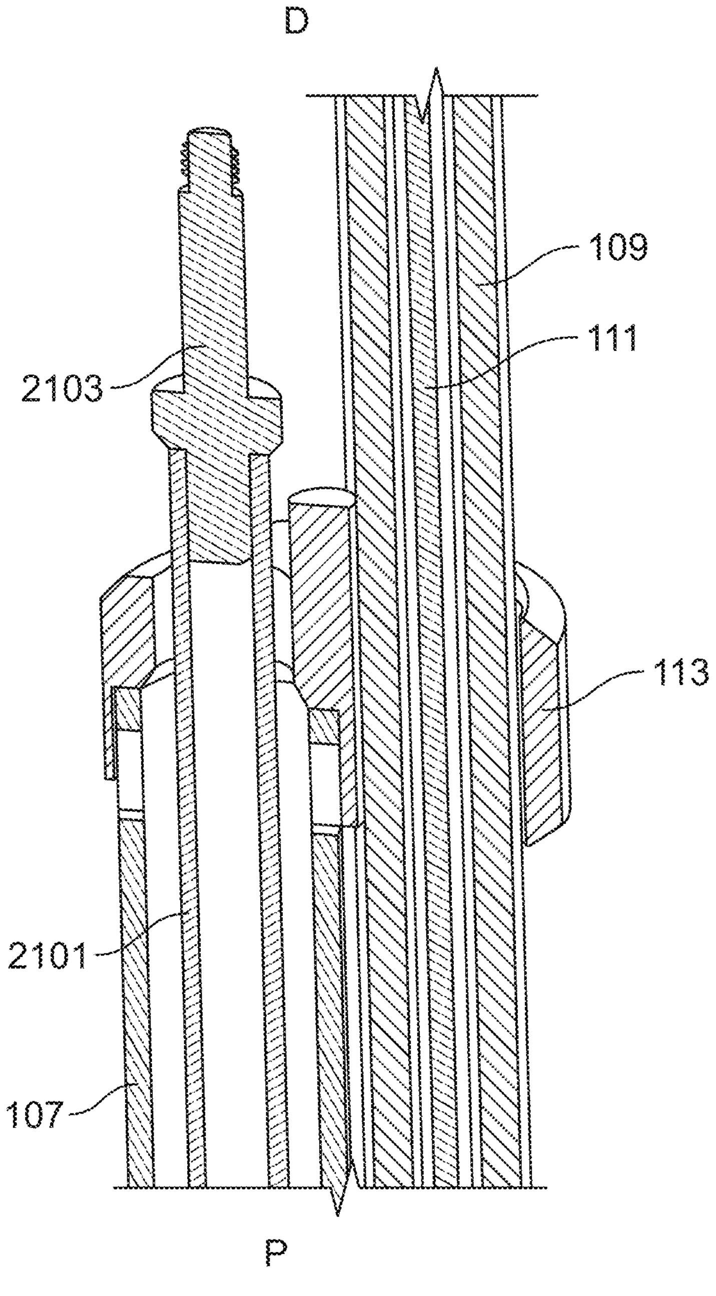
FIG. 23 shows a partial cross-section taken along view lines 23-23 (shown in FIG. 22)

FIG. 23 shows an illustrative partial cross-section of a portion of the apparatus illustrated in FIG. 22. In FIG. 23, torque wire 2101 may be advanced distally from pusher catheter 107. Torque wire 2101 may be advanced away from bushing 113.

Figure 24:
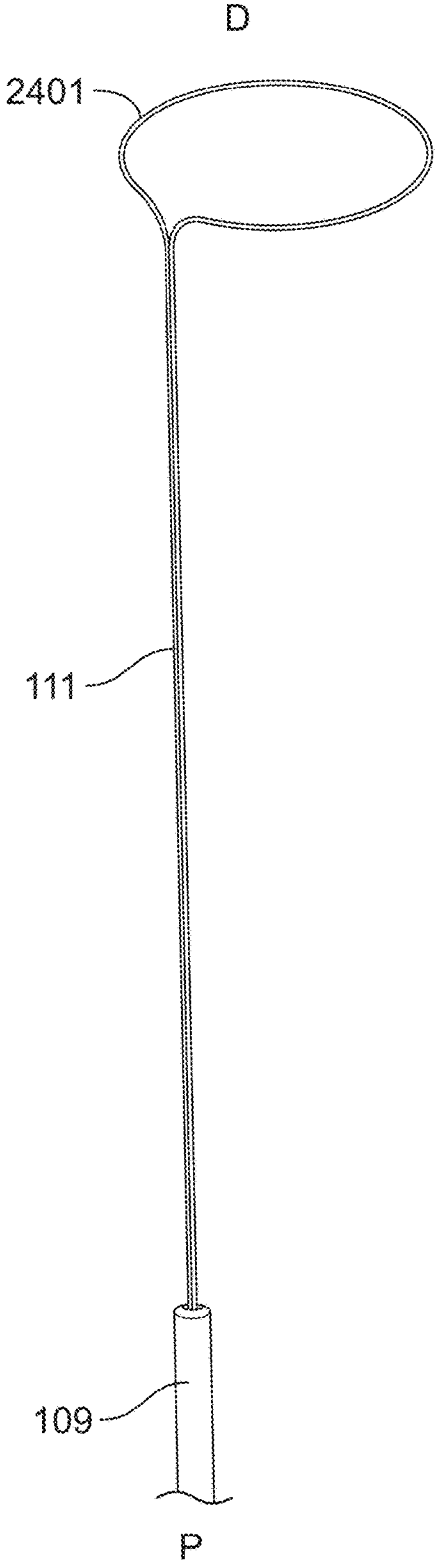
FIG. 24 shows illustrative apparatus in accordance with principles of the invention.

FIG. 24 shows an illustrative view of positioner catheter 109. Snare 111 may extend past positioner catheter 109. Snare 111 may end in a looped portion 2401. Snare 111 may generally be positioned within positioner catheter 109 except for looped portion 2401 which may generally extend out of positioner catheter 109. Looped portion 2401 may be retracted into positioner catheter 109 prior to withdrawal of positioner catheter 109 from implant 101 after deployment of implant 101 in the heart chamber.

Figure 25:
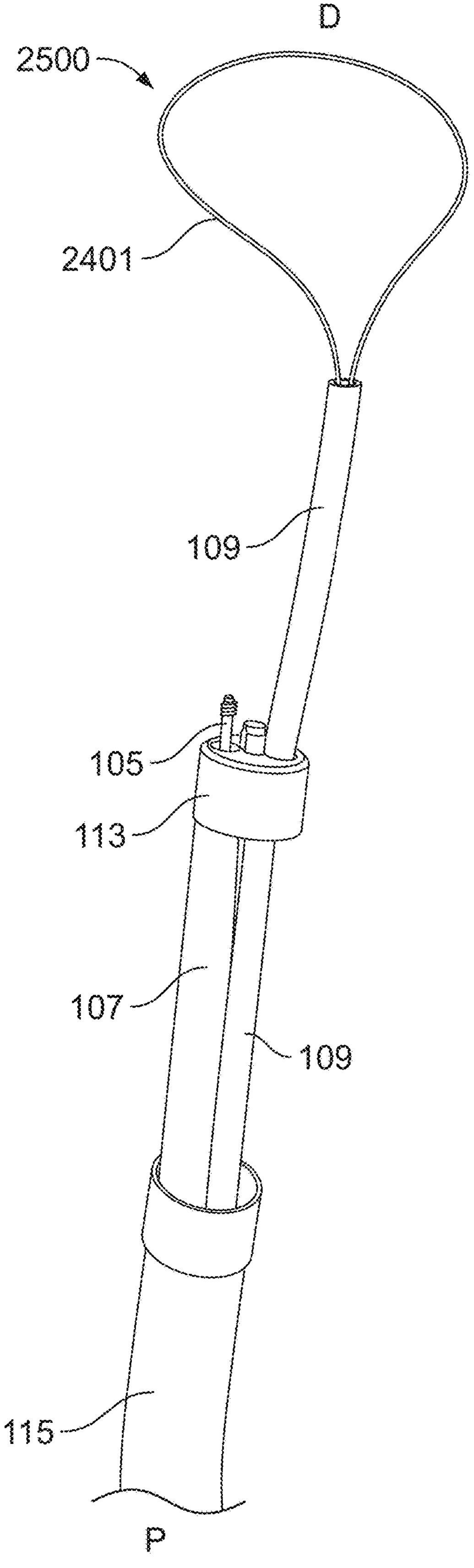
FIG. 25 shows illustrative apparatus in accordance with principles of the invention.

FIG. 25 shows an illustrative view of apparatus 2500. Positioner catheter 109 may be extended past bushing 113. In FIG. 25, looped portion 2401 of snare 111 may be partially withdrawn into positioner catheter 109. Withdrawing snare 111 into positioner catheter 109 may make looped portion 2401 smaller. Making looped portion 2401 smaller may tighten looped portion 2401 around implant 101. In this manner snare 111 may be tightened around an inner valve support of the implant to maintain the implant in a collapsed or partially-collapsed state.

Figure 26:
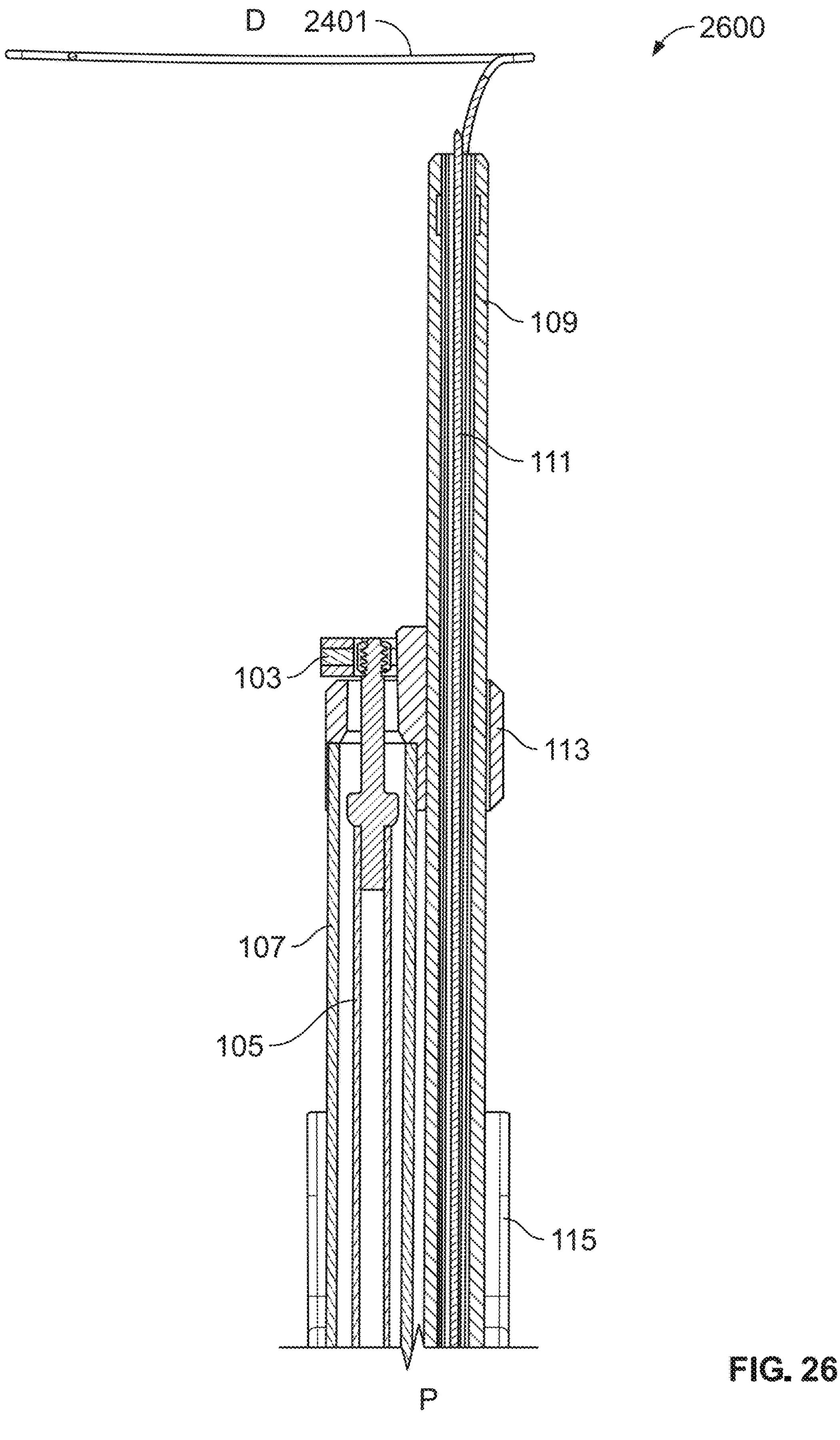
FIG. 26 shows illustrative apparatus in accordance with principles of the invention.

FIG. 26 shows an illustrative cross-sectional view of apparatus 2600. FIG. 26 may illustrate hub 103, delivery cable 105, pusher catheter 107, positioner catheter 109, snare 111, bushing 113, delivery catheter 115 and looped portion 2401.

Figure 27:
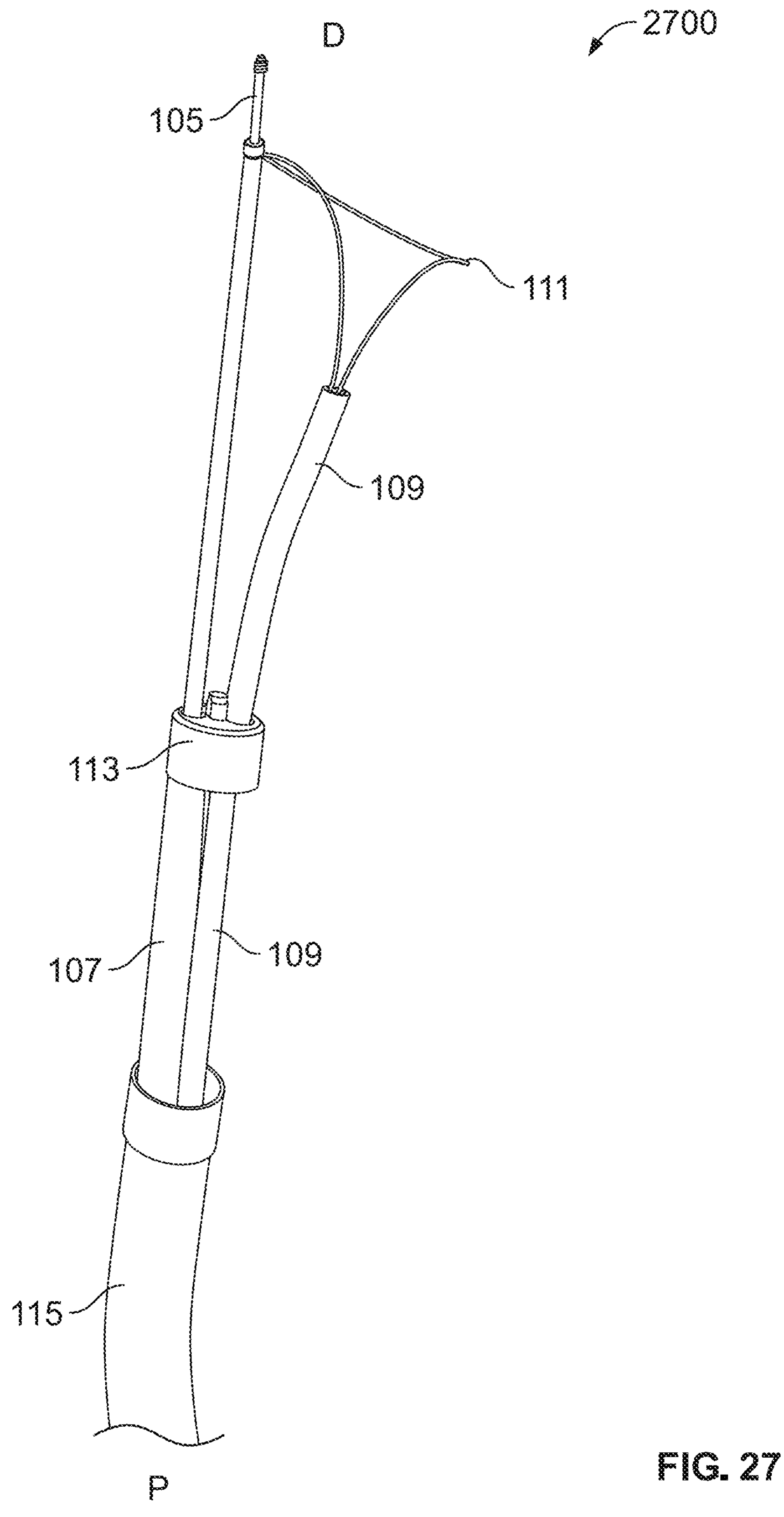
FIG. 27 shows illustrative apparatus in accordance with principles of the invention.

FIG. 27 shows an illustrative view of apparatus 2700. Apparatus 2700 may be configured for complete deployment of implant 101. Delivery cable 105 may be extended past bushing 113 to position the hub at the top of the left atrium. Snare 111 may be extended to release the inner valve support of implant 101. Delivery cable may be rotated to release implant 101 from delivery cable 105.

Figure 28:
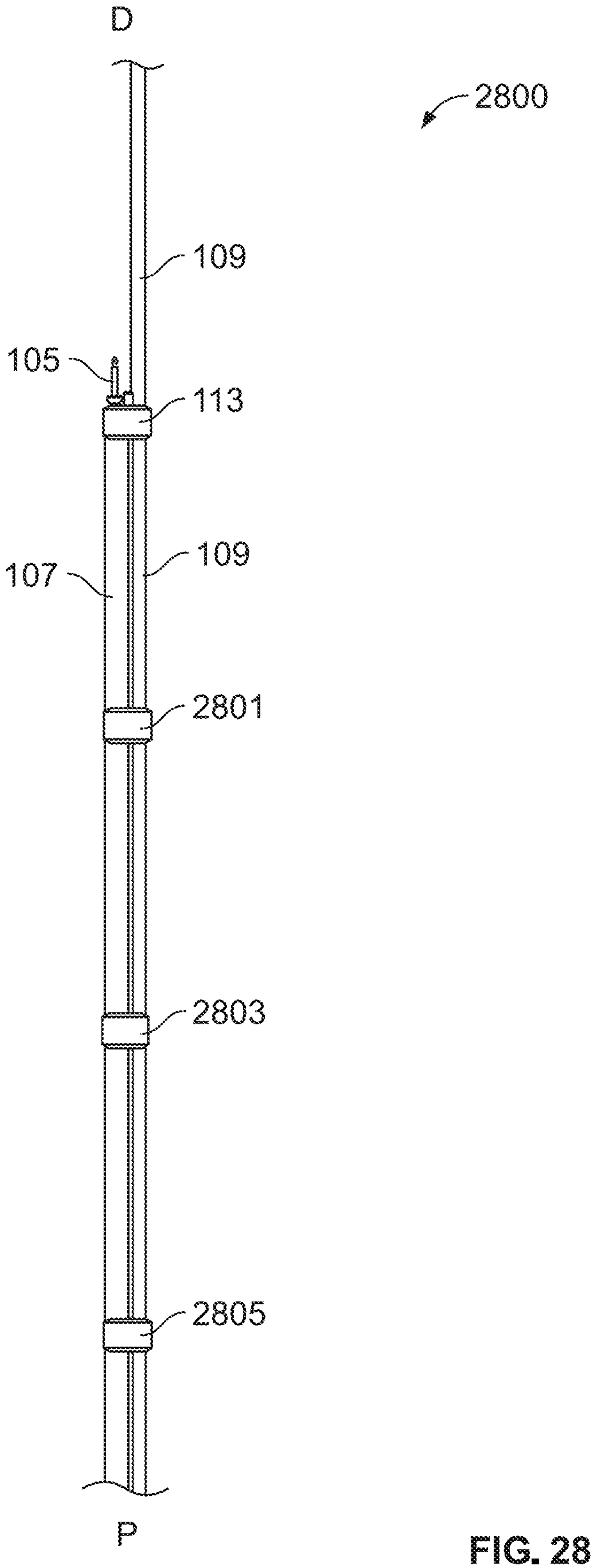
FIG. 28 shows illustrative apparatus in accordance with principles of the invention.

FIG. 28 shows illustrative apparatus 2800. Apparatus 2800 may include bushing 113. Apparatus 2800 may include one or more additional bushings 2801, 2803 and 2805. Each of additional bushings 2801, 2803 and 2805 may be fixed to pusher catheter 107. Each of additional bushings 2801, 2803 and 2805 may be slidingly engaged with positioner catheter 109.

One or more of additional bushings 2801, 2803 and 2805 may be slidingly engaged with pusher catheter 107.

Apparatus 2800 may be loaded into delivery catheter 115. Additional bushings 2801, 2803 and 2805 may provide delivery catheter 115 with increased strength to prevent bunching of delivery catheter 115 while manipulating implant 101.

Figure 29:
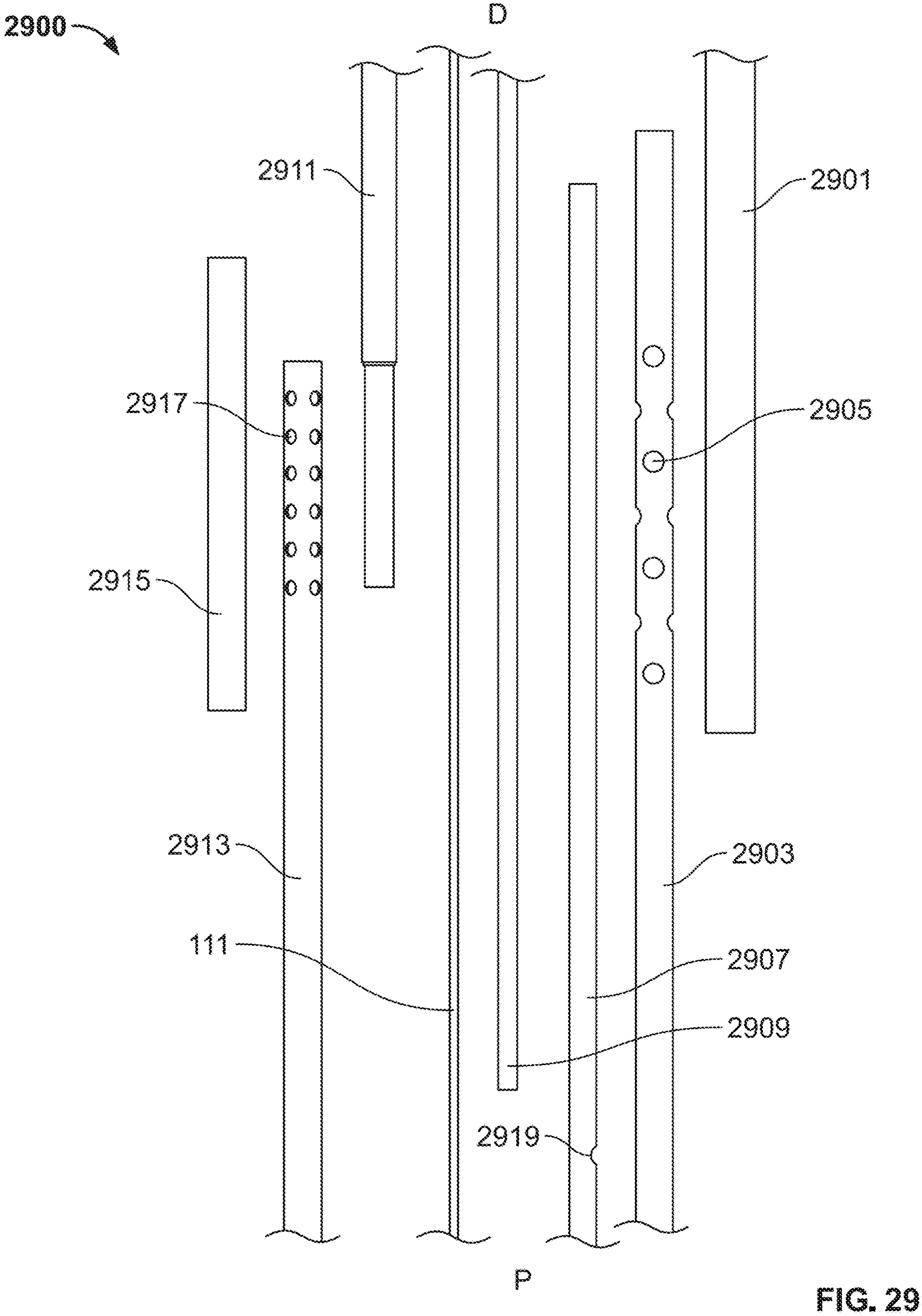
FIG. 29 shows illustrative apparatus in accordance with principles of the invention.

FIG. 29 shows an exploded view of apparatus 2900. Pusher catheter 107 may include distal pusher catheter 2901 and proximal pusher catheter 2903. Proximal pusher catheter 2903 may be welded to distal pusher catheter 2901. Proximal pusher catheter 2903 may be pressed fit to distal pusher catheter 2901. Proximal pusher catheter 2903 may include holes 2905. Holes 2905 may reflow distal pusher catheter 2901 onto proximal pusher catheter 2903 to attach proximal pusher catheter 2903 and distal pusher catheter 2901 together.

Delivery cable 105 may include proximal delivery cable 2907 and distal delivery cable 2909. Proximal delivery cable 2907 may be welded to distal delivery cable 2909. Proximal delivery cable 2907 may be pressed fit to distal delivery cable 2909.

Positioner catheter 109 may include proximal positioner catheter 2911 and distal positioner catheter 2913. Proximal positioner catheter 2911 may include a smaller diameter end. The smaller diameter end may fit into distal positioner catheter 2913. Sheath 2915 may extend over a portion of proximal positioner catheter 2911 and distal positioner catheter 2913, including extending over a connection point between proximal positioner catheter 2911 and distal positioner catheter 2913. Distal positioner catheter 2913 may include holes 2917. Holes 2917 may reflow distal positioner catheter 2913 onto proximal positioner catheter 2911 to attach distal positioner catheter 2913 and proximal positioner catheter 2911 together.

Proximal delivery cable 2907 may include hole 2919. There may be 1, 2, 3, 4 or any suitable number of holes 2919 along proximal delivery catheter 2907. Hole 2919 may direct the biocompatible fluid injected into the proximal end of delivery cable 105 into pusher catheter 107. The biocompatible fluid may fill pusher catheter 107. The biocompatible fluid may flow from pusher catheter 107 past bushing 113 and over implant 101. During loading the biocompatible fluid may flow over implant 101 and into the implant loading device. When pusher catheter 107 and bushing 113 are within delivery catheter 115, such as during deployment or recapture, delivery catheter 115 may be filled with the biocompatible fluid.

Figure 30:
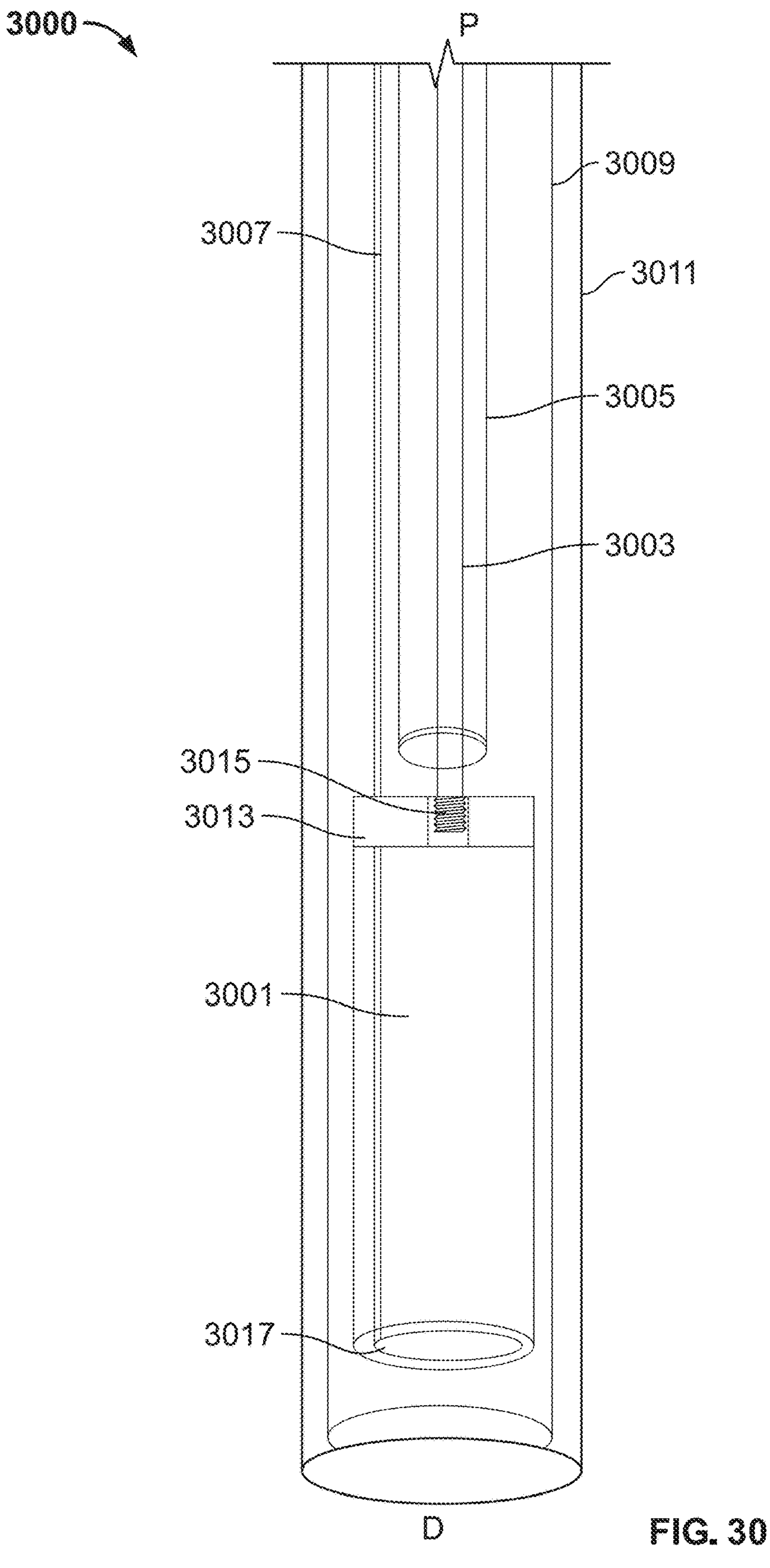
FIG. 30 shows schematically illustrative apparatus in accordance with principles of the invention.

FIG. 30 shows illustrative apparatus 3000. Apparatus 3000 may include implant 3001, delivery cable 3003, pusher catheter 3005, snare 3007, delivery catheter 3009 and sheath 3011. Implant 3001 may include hub 3013. Hub 3013 may threadedly engage threaded end 3015 of delivery cable 3003. Snare 3007 may include looped portion 3017 at an end of snare 3007.

Figure 31:
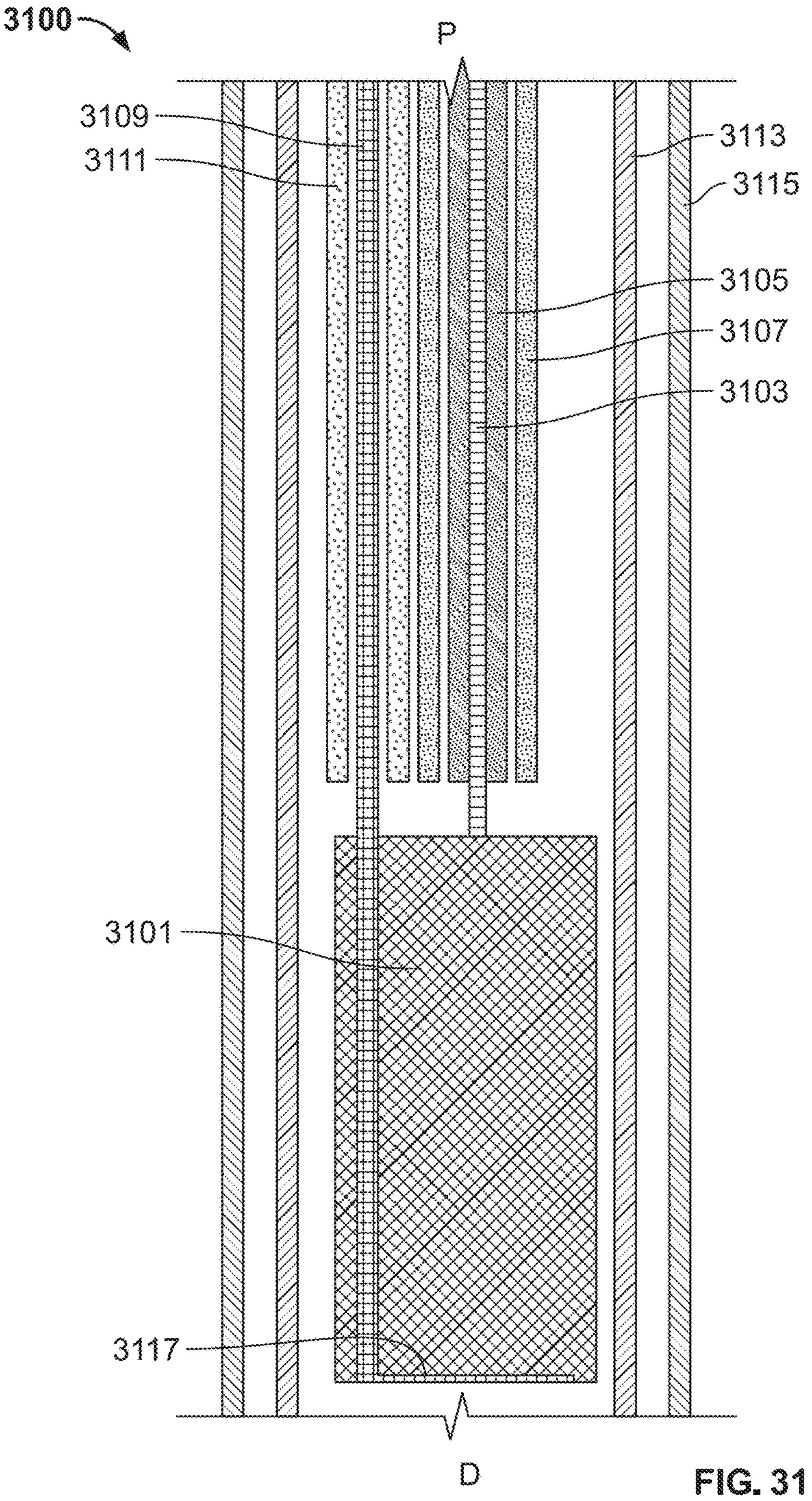
FIG. 31 shows schematically illustrative apparatus in accordance with principles of the invention.

FIG. 31 shows a cross-sectional view of illustrative apparatus 3100. Apparatus 3100 may include implant 3101, delivery cable 3103, first pusher catheter 3105, second pusher catheter 3107, snare 3109, positioner catheter 3111, delivery catheter 3113 and sheath 3115. Snare 3109 may include looped portion 3117 at an end of snare 3109.

Figure 32:
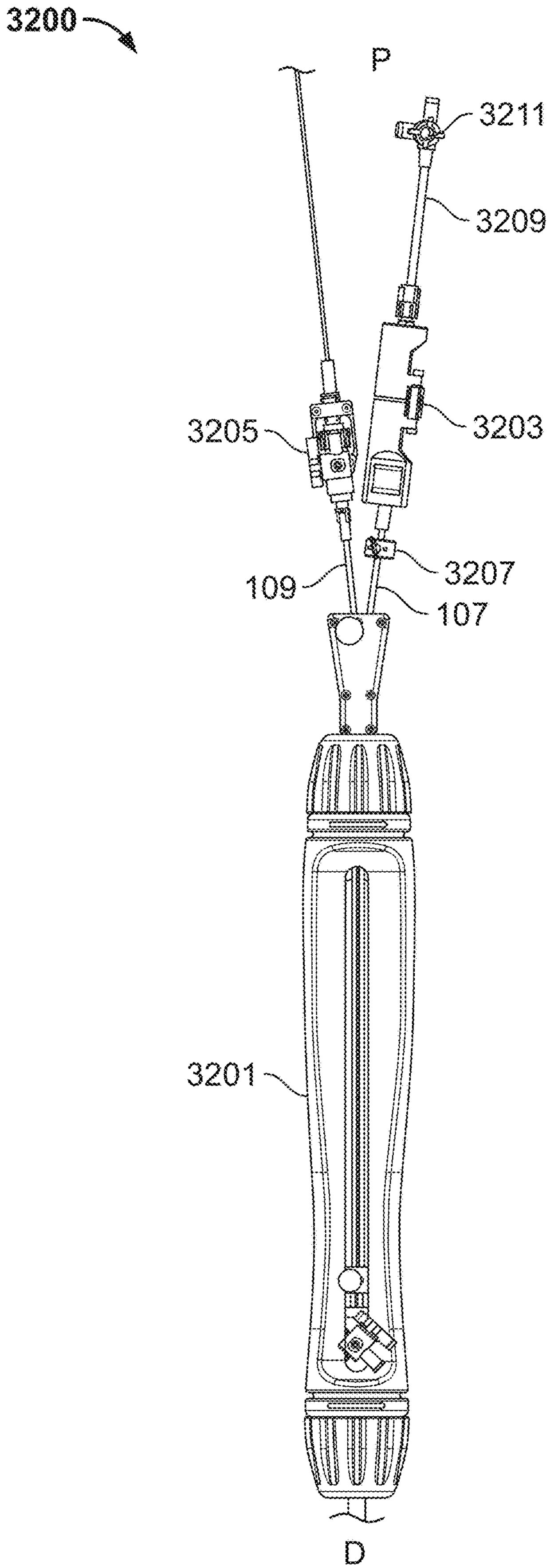
FIG. 32 shows illustrative apparatus in accordance with principles of the invention.

FIG. 32 shows illustrative apparatus 3200. Apparatus 3200 may include main handle 3201, gauge handle 3203, positioner catheter control handle 3205, limit screw 3207, tubing 3209 and valve 3211. Limit screw 3207 may clamp onto an outer surface of pusher catheter 107. Limit screw 3207 may limit how far pusher catheter 107 is advanced into the body. When limit screw 3207 reaches main handle 3201, limit screw 3207 may prevent pusher catheter 107 from any further distal advancement.

Tubing 3209 may receive the biocompatible fluid through valve 3211. The biocompatible fluid may flow to the delivery cable. The delivery cable may be hollow to receive the biocompatible fluid. The biocompatible fluid may be used to flush the implant and the implant loading device during the loading.

Figure 33:
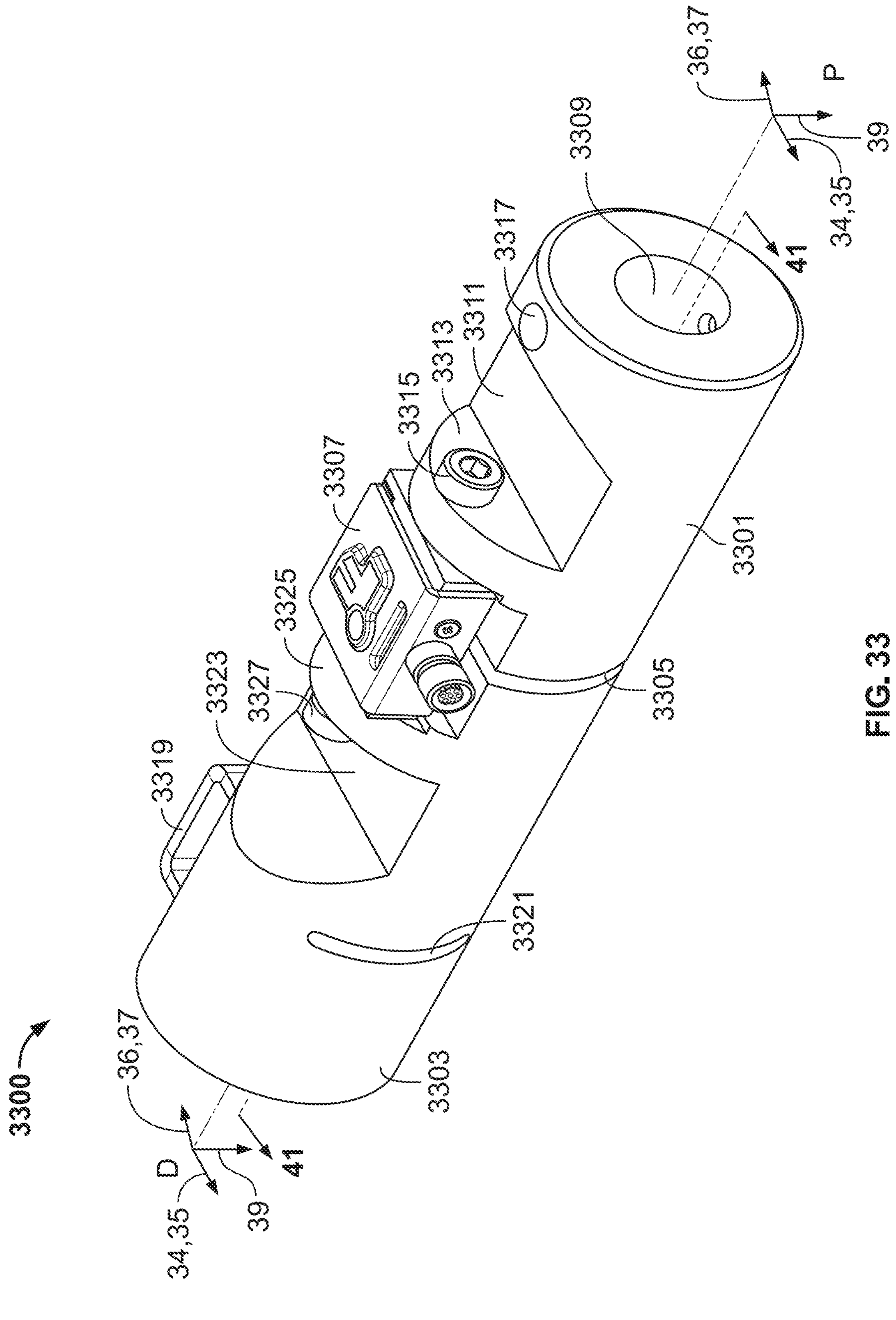
FIG. 33 shows illustrative apparatus (delivery cable and pusher catheter removed) in accordance with principles of the invention.

FIG. 33 shows illustrative gauge handle 3300 with the delivery cable and the pusher catheter removed. Gauge handle 3300 may include first base 3301. Gauge handle 3300 may include second base 3303. First base 3301 may be spaced apart from second base 3303 to define gap 3305. Gauge handle 3300 may include force gauge 3307. Force gauge 3307 may extend across gap 3305. First base 3301 may be coupled to a first end of force gauge 3307. Second base 3303 may be coupled to a second end of force gauge 3307. Force gauge 3307 may display the force differential between the pusher catheter and the delivery cable. Gauge handle 3300 may be used to hold the pusher catheter, delivery cable and force gauge 3307 during a manipulation of the implant.

First base 3301 may hold the delivery cable. First base 3301 may support force gauge 3307. First base 3301 may define lumen 3309. Lumen 3309 may receive the delivery cable. First base 3301 may define recess 3311. Recess 3311 may receive force gauge 3307. First base 3301 may include boss 3313. Boss 3313 may extend into recess 3311. Boss 3313 may define a bore. Screw 3315 may be inserted through the bore and into a threaded bore defined in force gauge 3307. First base 3301 may define holes 3317. Fasteners may be inserted through holes 3317 to couple first base 3301 to the delivery cable.

Second base 3303 may hold the pusher catheter. Second base 3303 may support force gauge 3307. Second base 3303 may include biased lock 3319. Second base 3303 may define recess 3323. Second base 3303 may include boss 3325 and screw 3327.

Biased lock 3319 may be positioned inside slot 3321 defined in second base 3303. Biased lock 3319 may couple second base 3303 to the pusher catheter. Second base 3303 may define recess 3323. Recess 3323 may receive force gauge 3307. Second base 3303 may include boss 3325. Boss 3325 may define a bore. Screw 3327 may be inserted through the bore and into a threaded bore defined in force gauge 3307.

Figure 34:
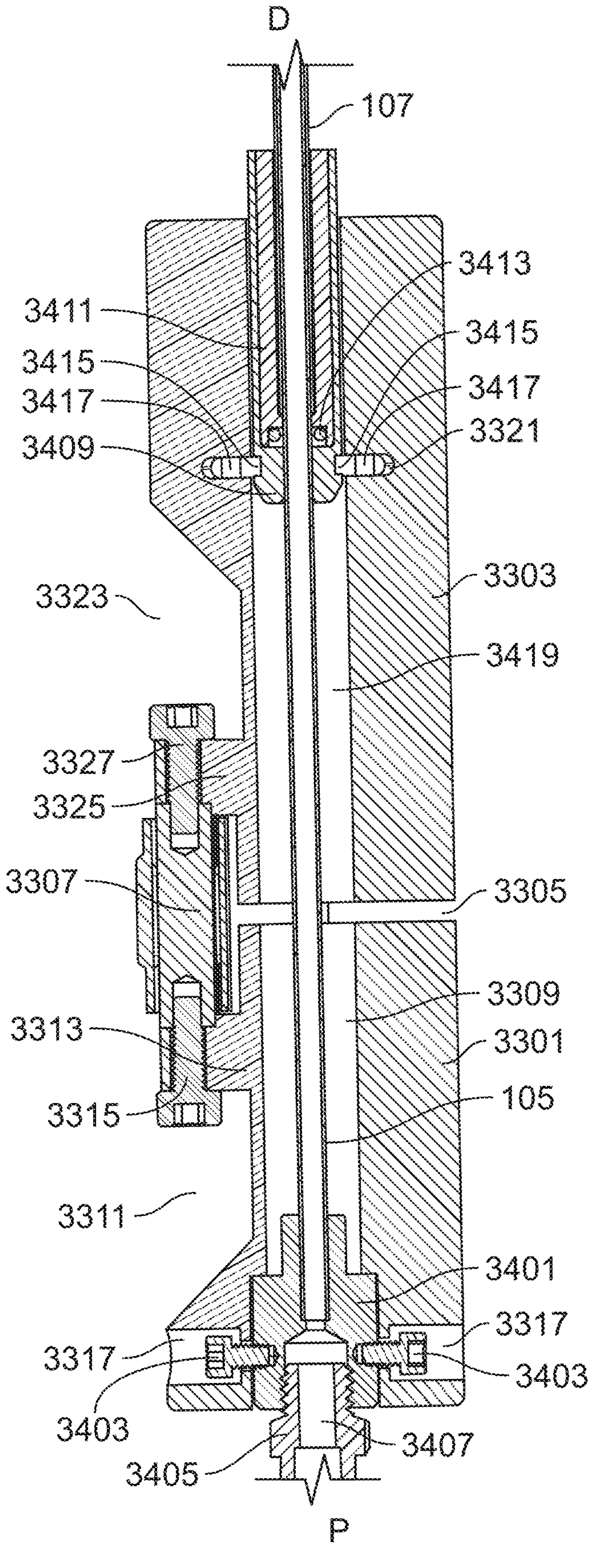
FIG. 34 shows a cross-section taken along view lines 34-34 (shown in FIG. 33) (delivery cable and pusher catheter included)

FIG. 34 shows a cross-section of illustrative gauge handle 3300 taken along lines 34-34 of FIG. 33 with delivery cable 105 and pusher catheter 107 included.

Delivery cable 105 may be coupled to first base 3301 via cylindrical boss 3401. Screws 3403 may be inserted through holes 3317 and into threaded bores in cylindrical boss 3401 to couple delivery cable 105 to first base 3301.

Delivery cable 105 may receive biocompatible fluid. The biocompatible fluid may flow into a hollow center in delivery cable 105. The biocompatible fluid may be used to flush the implant and the implant loading device during the loading. Threaded end cap 3405 may be removably coupled with cylindrical boss 3401. Threaded end cap 3405 may be threaded into an end of cylindrical boss 3401. Threaded end cap 3405 may define lumen 3407. Lumen 3407 may receive the biocompatible fluid. The biocompatible fluid may be saline.

Pusher catheter 107 may be removably coupled to second base 3303. Pusher catheter 107 may be coupled via biased lock 3319. Pusher catheter 107 may include outer encasement member 3409, inner encasement member 3411 and O-ring 3413. O-ring 3413 may be positioned between inner encasement member 3411 and delivery cable 105. O-ring 3413 may be positioned between inner encasement member 3411 and pusher catheter 107. O-ring 3413 may be positioned anywhere along inner encasement member 3411.

Biased lock 3319 may engage pusher catheter 107 via groove 3415 defined in outer encasement member 3409. Biased lock 3319 may couple pusher catheter 107 to second base 3303 via engagement with groove 3415.

To prevent removal of biased lock 3319 from second base 3303, pins 3417 may extend through biased lock 3319.

Pusher catheter 107 may be coupled to second base 3303 inside lumen 3419 defined in second base 3303. Pusher catheter 107 may be positioned in, and terminate within, lumen 3419. Delivery cable 105 may be positioned within lumen 3419.

Pusher catheter 107 may be coupled to delivery cable 105 when delivery cable 105 is locked to first base 3301 and pusher catheter 107 is locked to second base 3303. In this configuration, advancing pusher catheter 107 may advance delivery cable 105 via force gauge 3307 such that pusher catheter 107 and delivery cable 105 move in unison.

Pusher catheter 107 and delivery cable 105 may move separately relative to the main handle when delivery cable 105 is unlocked from first base 3301 and pusher catheter 107 is unlocked from second base 3303.

Figure 35:
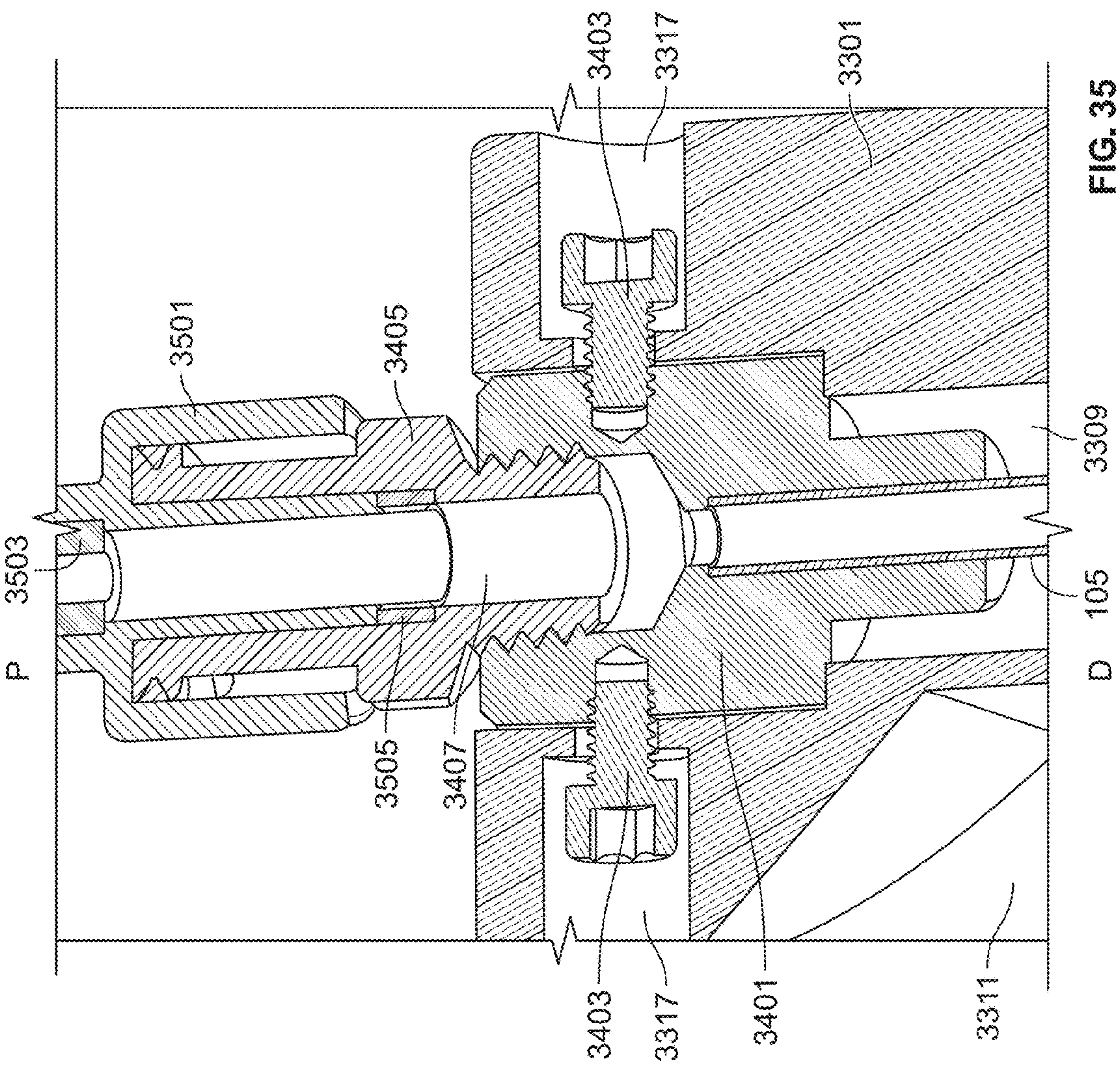
FIG. 35 shows a partial cross-section taken along view lines 35-35 (shown in FIG. 33) (delivery cable included)

FIG. 35 shows a partial cross-section of a portion of illustrative gauge handle 3300 taken along lines 35-35 of FIG. 33 with delivery cable 105 included.

The biocompatible fluid may be injected into delivery cable 105 via knob 3501 and tube 3503. Knob 3501 may be threaded onto threaded end cap 3405. Tube 3503 may deliver the biocompatible fluid to threaded end cap 3405. Gasket 3505 may seal a connection between knob 3501 and threaded end cap 3405. The biocompatible fluid may fill delivery cable 105, pusher catheter 107 and delivery catheter 115.

Figure 36:
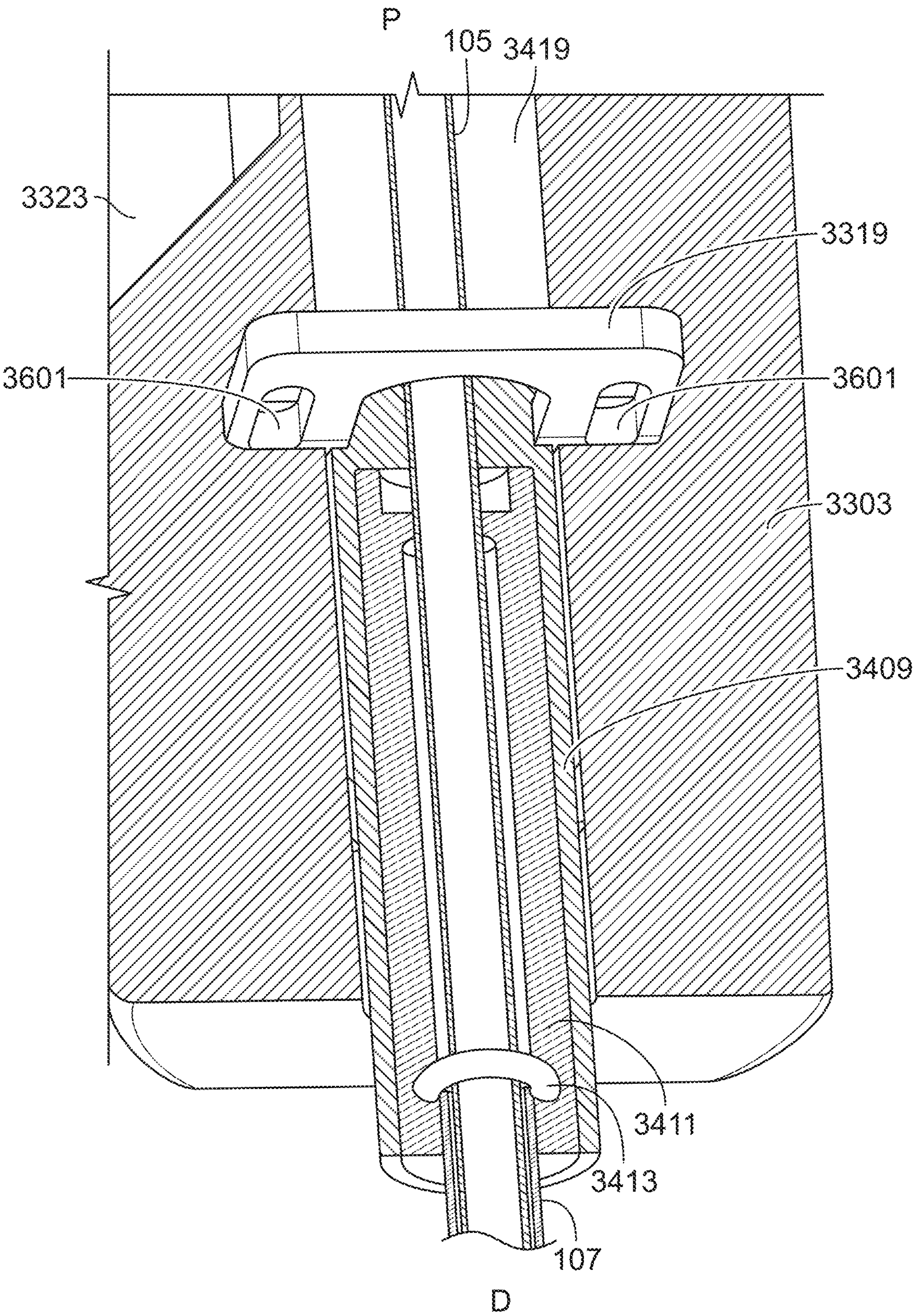
FIG. 36 shows a partial cross-section taken along view lines 36-36 (shown in FIG. 33) (delivery cable and pusher catheter included)

FIG. 36 shows a partial cross-section of illustrative gauge handle 3300 taken along lines 36-36 of FIG. 33 with delivery cable 105 and pusher catheter 107 included. Biased lock 3319 may engage grooves 3415 to lock pusher catheter 107 to second base 3303. Biased lock 3319 may include first and second cutouts 3601. Cutouts 3601 may receive pins 3417. Pins 3417 may prevent removal of biased lock 3319 from second base 3303.

Figure 37:
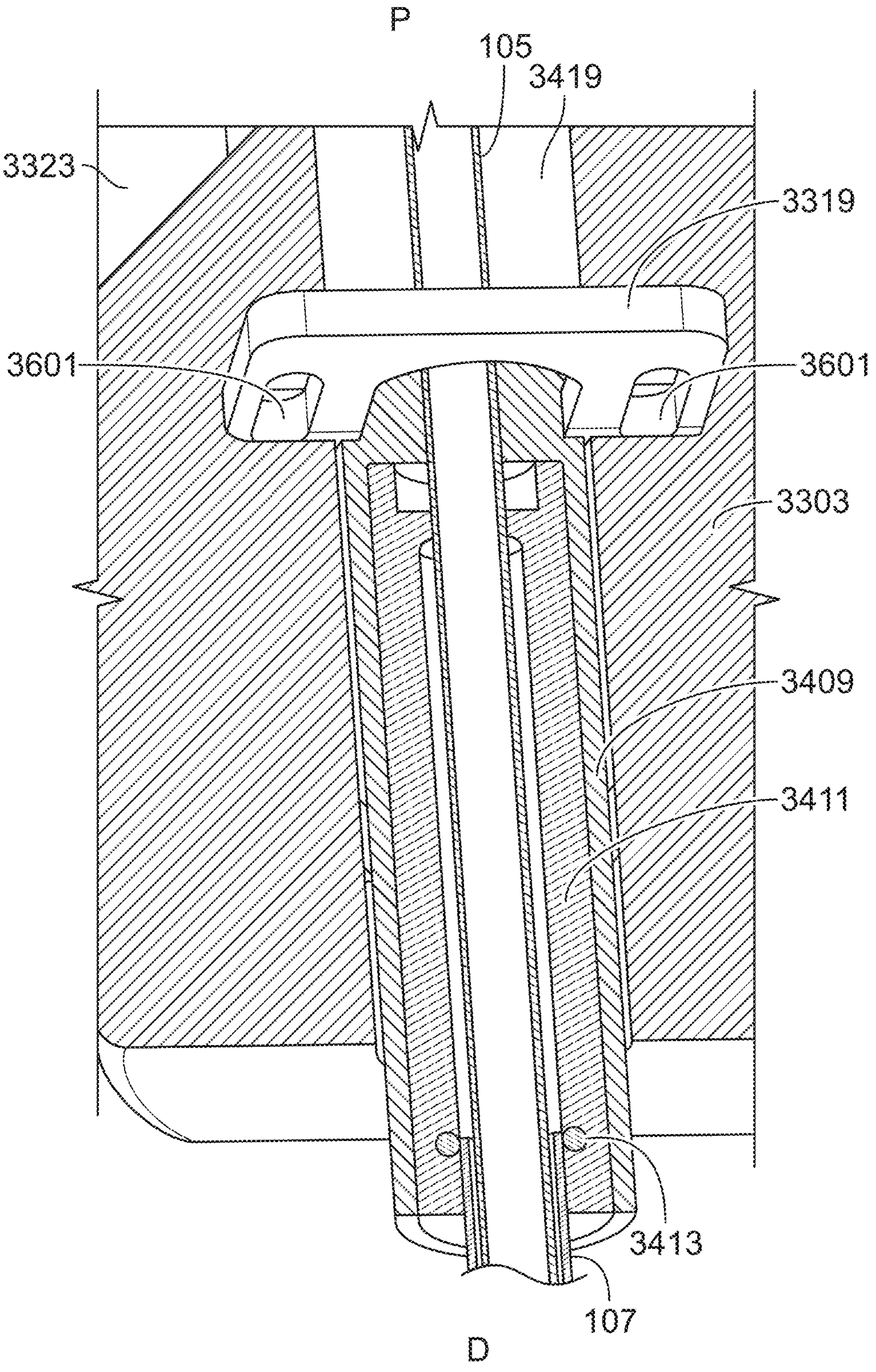
FIG. 37 shows a partial cross-section taken along view lines 37-37 (shown in FIG. 33) (delivery cable and pusher catheter included)

FIG. 37 shows a partial cross-section of illustrative gauge handle 3300 taken along lines 37-37 of FIG. 33. A cross-section of O-ring 3413 may be seen in FIG. 37.

Figure 38:
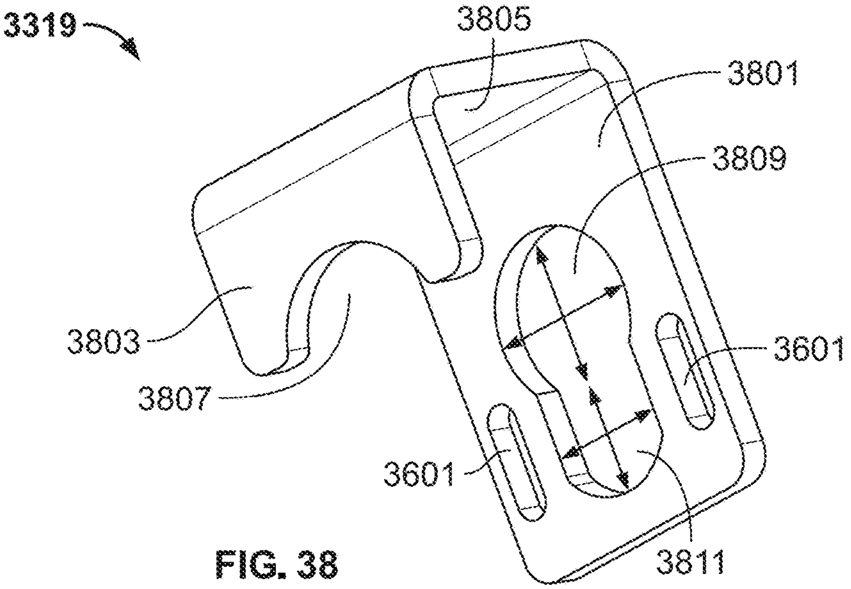
FIG. 38 shows illustrative apparatus in accordance with principles of the invention.

FIG. 38 shows illustrative biased lock 3319. Biased lock 3319 may removably lock pusher catheter 107 to second base 3303. Biased lock 3319 may include first plate 3801, second plate 3803 and top plate 3805. Top plate 3805 may connect first plate 3801 and second plate 3803. Biased lock 3319 may define groove 3807, first and second cutouts 3601 and a third cutout including circular section 3809 and elongated section 3811. First and second cutouts 3601 may receive pins 3417 to prevent biased lock 3319 from falling out of second base 3303. Groove 3807 may be sized to surround outer encasement member 3409. Circular section 3809 may be sized to receive outer encasement member 3409. Elongated section 3811 may be sized to engage grooves 3415.

First plate 3801 may be shaped to be positioned in slot 3321. Second plate 3803 may be shaped to be positioned in second base 3303.

Figure 39:
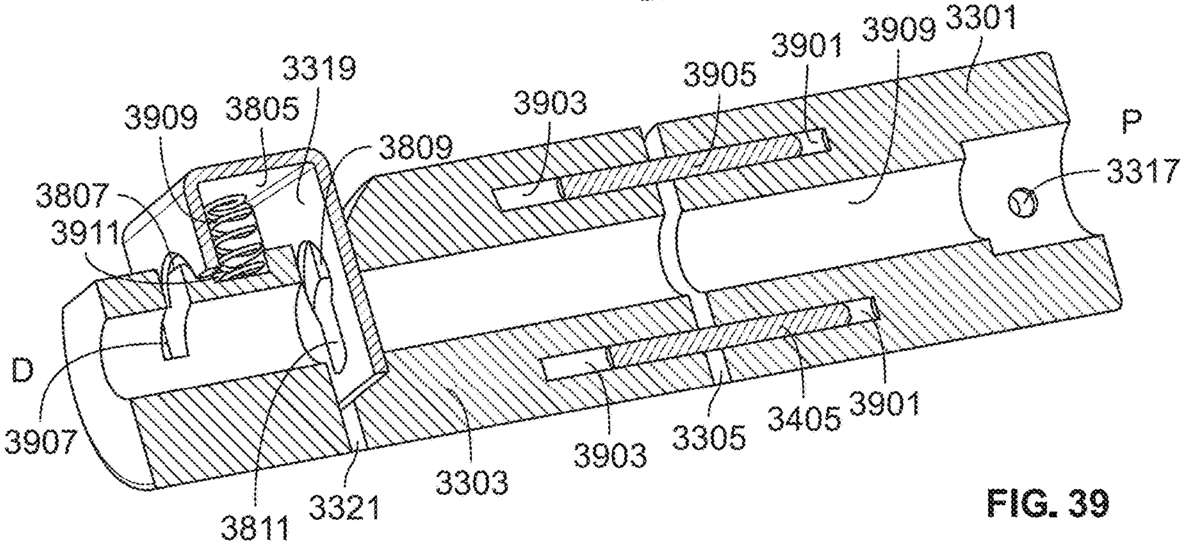
FIG. 39 shows a partial cross-section taken along view lines 39-39 (shown in FIG. 33)

FIG. 39 shows a partial cross-section of illustrative gauge handle 3300 taken along lines 39-39 of FIG. 33. First base 3301 may be aligned with second base 3303 via pins 3905. First base 3301 may define first bores 3901. Second base 3303 may define second bores 3903. A number of second bores 3903 may correspond to a number of first bores 3901. Pins 3905 may be positioned within first bores 3901 and second bores 3903 to align first base 3301 with second base 3303.

A number of pins 3905 may correspond to the number of first bores 3901. There may be 1, 2, 3, 4 or any suitable number of first bores 3901. When there is one first bore 3901, a cross-section of the first bore 3901 and second bore 3903 may be non-circular. When there is more than one first bore 3901, a cross-section of the first bore may be circular or non-circular. The cross-section of the pins 3905 may correspond to the cross-section of the first bore 3901 and the second bore 3903.

Second base 3303 may receive biased lock 3319. Biased lock 3319 may be received via first plate 3801 and second plate 3803. First plate 3801 may be received in slot 3321. Second plate 3803 may be received in short slot 3907 defined in second base 3303. Short slot 3907 may extend partially within second base 3303. Short slot 3907 may be sized to receive second plate 3803.

Biased lock 3319 may be biased away from second base 3303 via spring 3909. Spring 3909 may be positioned between top plate 3805 and groove 3911 defined in second base 3303 to bias biased lock 3319 in a non-depressed state. Biased lock 3319 may be depressed by pushing biased lock toward second base 3303. Biased lock 3319 may be depressed until second plate 3803 contacts the end of short slot 3907. When second plate 3803 contacts the end of short slot 3907, circular section 3809 and groove 3807 may be aligned with lumen 3419. When circular section 3809 is aligned with lumen 3419, outer encasement member 3409 may be inserted into circular section 3809. When outer encasement member 3409 is inserted into circular section 3890 grooves 3415 may be aligned with circular section 3809. Releasing biased lock 3319 when grooves 3415 are aligned with circular section 3809 may engage elongated section 3811 with grooves 3415. When grooves 3415 engage elongated section 3811 outer encasement member 3409 may be locked to second base 3303. When outer encasement member 3409 is locked to second base 3303, pusher catheter 107 may be locked to second base 3303.

Figure 40:
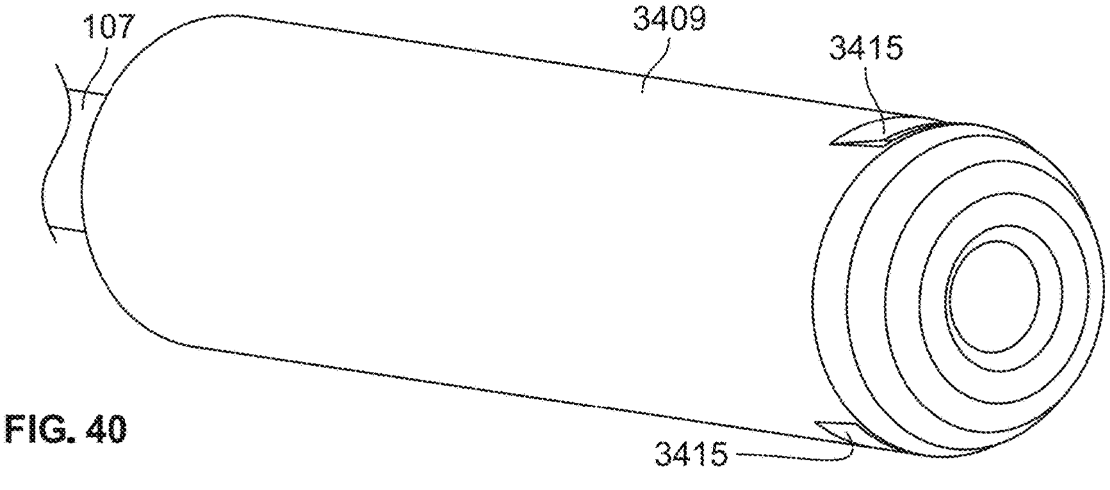
FIG. 40 shows illustrative apparatus in accordance with principles of the invention.

FIG. 40 shows illustrative outer encasement member 3409.

Figure 41:
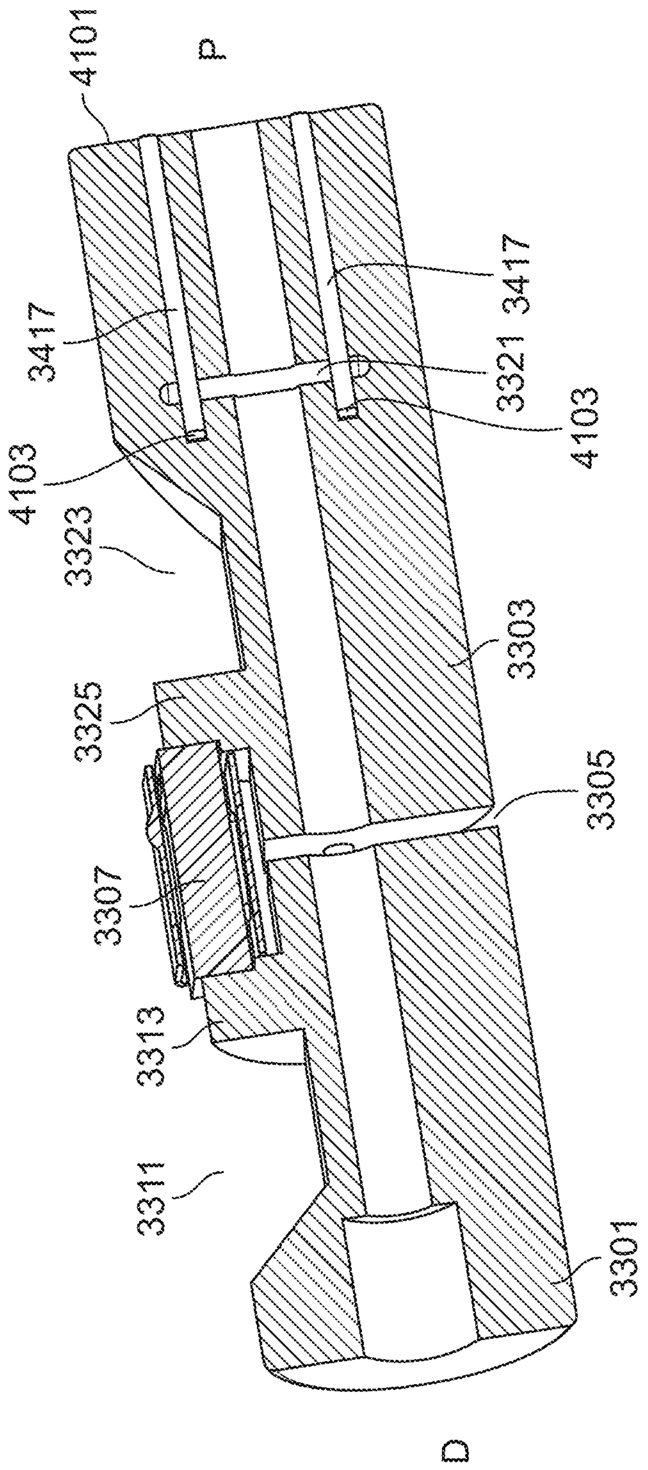
FIG. 41 shows a cross-section taken along view lines 41-41 (shown in FIG. 33)

FIG. 41 shows a cross-section of a portion of illustrative gauge handle 3300 taken along lines 41-41 of FIG. 33. Pins 3417 may be inserted from second end 4101 of second base 3303 into bores 4103. Pins 3417 may be inserted into first and second cutouts 3601 to retain biased lock 3319 within slot 3321 of second base 3303.

Figure 42:
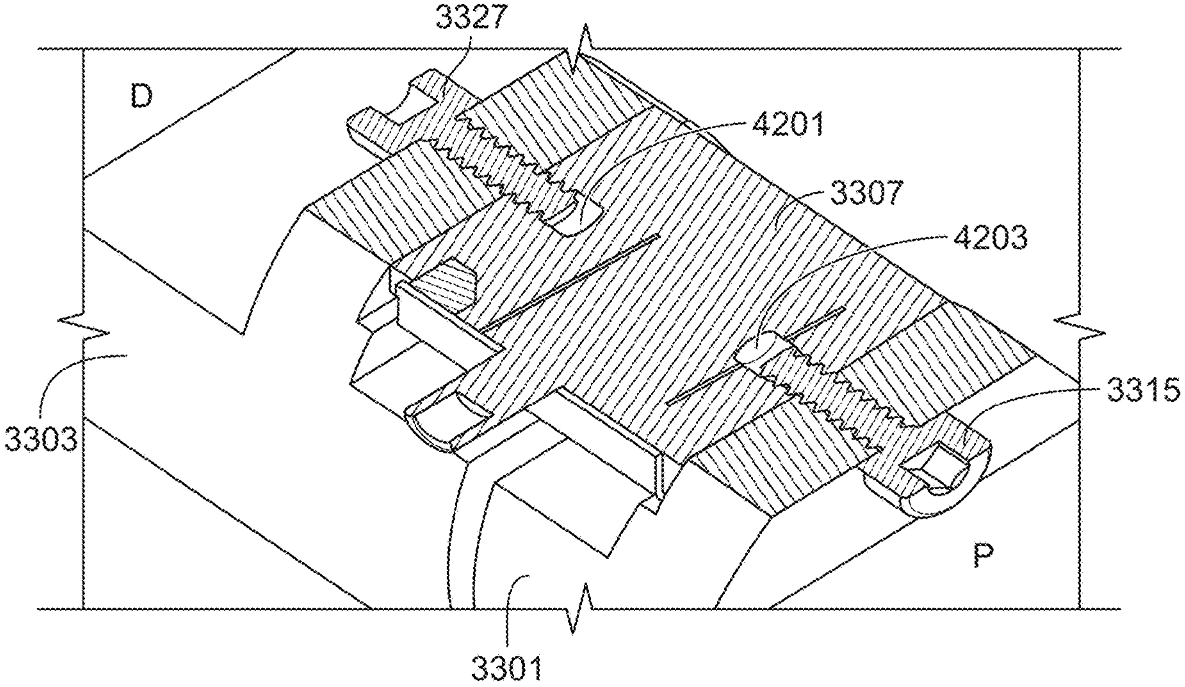
FIG. 42 shows illustrative apparatus in accordance with principles of the invention.

FIG. 42 shows a partial cross-section of a portion of illustrative gauge handle 3300. Force gauge 3307 may define threaded bores 4201 and 4203. Threaded bore 4203 may receive screw 3315. Threaded bore 4201 may receive screw 3327. Force gauge 3307 may be coupled to first base 3301 via threaded bore 4203 and screw 3315. Force gauge 3307 may be coupled to second base 3303 via threaded bore 4201 and screw 3327.

Figure 43:
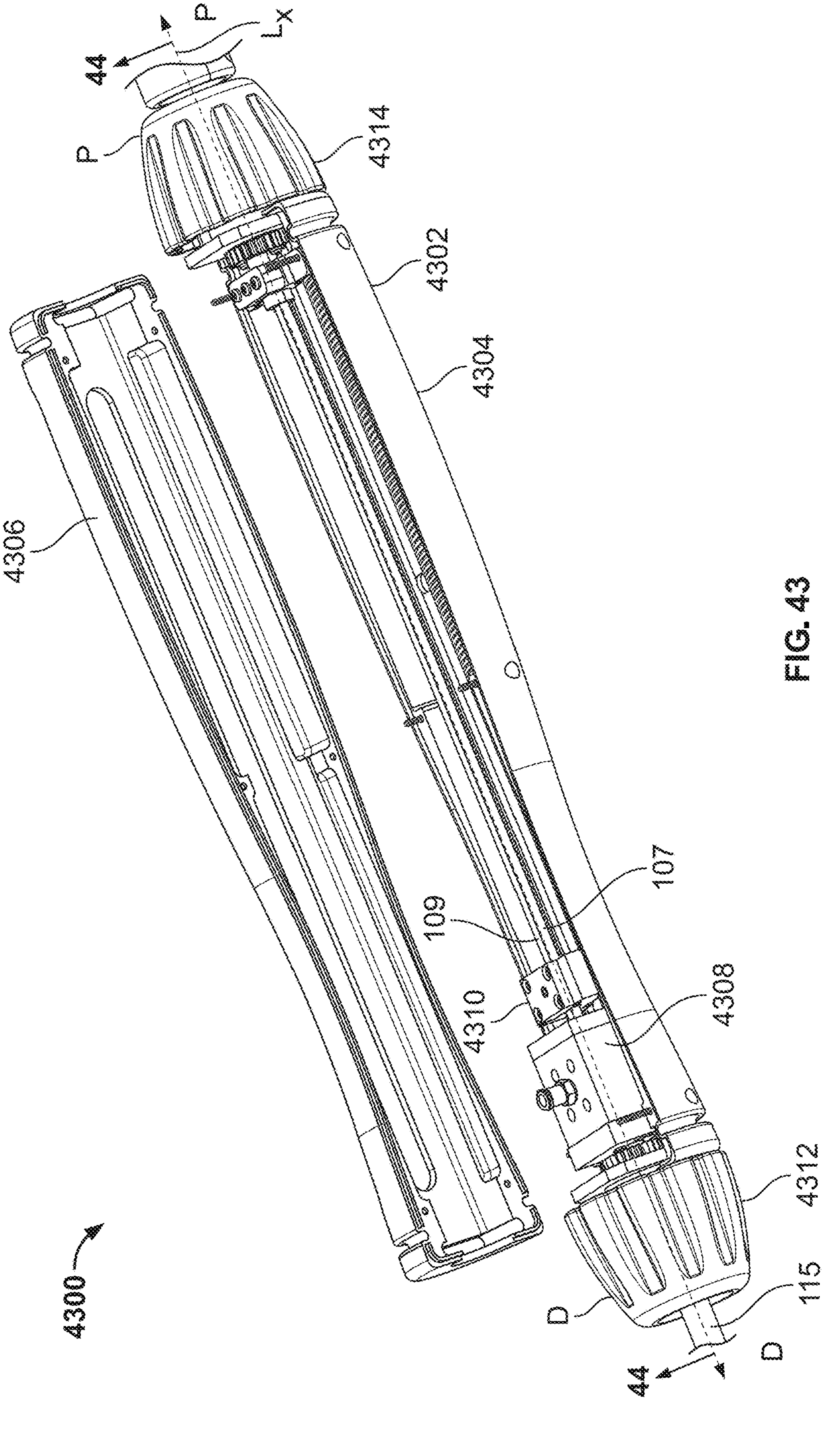
FIG. 43 shows illustrative apparatus in accordance with principles of the invention.

FIG. 43 shows illustrative main control handle 4300. Main control handle 4300 may have central axis Lx, which may extend between proximal and P and distal end D of main control handle 4300. Main control handle 4300 may include housing 4302. Housing 4302 may include shell 4304 and shell 4306 (displaced and rotated relative to shell 4304 for illustration).

Main control handle 4300 may be fixed to an instrument stand. Delivery catheter 115 may extend in distal direction D, toward a location at which the implant such as implant 101 may be attached to the delivery cable. Pusher catheter 107 may extend distally toward the implant. Pusher catheter 107 may extend proximally to a delivery handle, which may include the force gauge. Positioner catheter 109 may extend distally toward the implant. Positioner catheter 109 may extend proximally to a delivery handle, which may not include a force gauge.

Main control handle 4300 may include carriage 4308. Carriage 4308 may be fixed to distal end of delivery catheter 115. Carriage 4308 may include a passageway that allows pusher catheter 107 to slide relative to carriage 4308. Carriage 4308 may include a passageway that allows positioner catheter 109 to slide relative to carriage 4308.

Main control handle 4300 may include carriage 4310. Carriage 4310 may be fixed to pusher catheter 107. Carriage 4310 may include a passageway that allows positioner catheter 109 to slide relative to carriage 4310.

Main control handle 4300 may include knob 4312. Knob 4312 may be turned to reposition carriage 4308 in main control handle 4300. Knob 4312 may thus advance (toward the distal direction) and retract (toward the proximal direction) delivery catheter 115 relative to main control handle 4300 without disturbing the positions of pusher catheter 107 or positioner catheter 109.

Main control handle 4300 may include knob 4314. Knob 4314 may be turned to reposition carriage 4310. Knob 4314 may thus advance and retract pusher catheter 107 relative to main control handle 4300 without disturbing the positions of deliver catheter 115 or positioner catheter 109.

Figure 44:
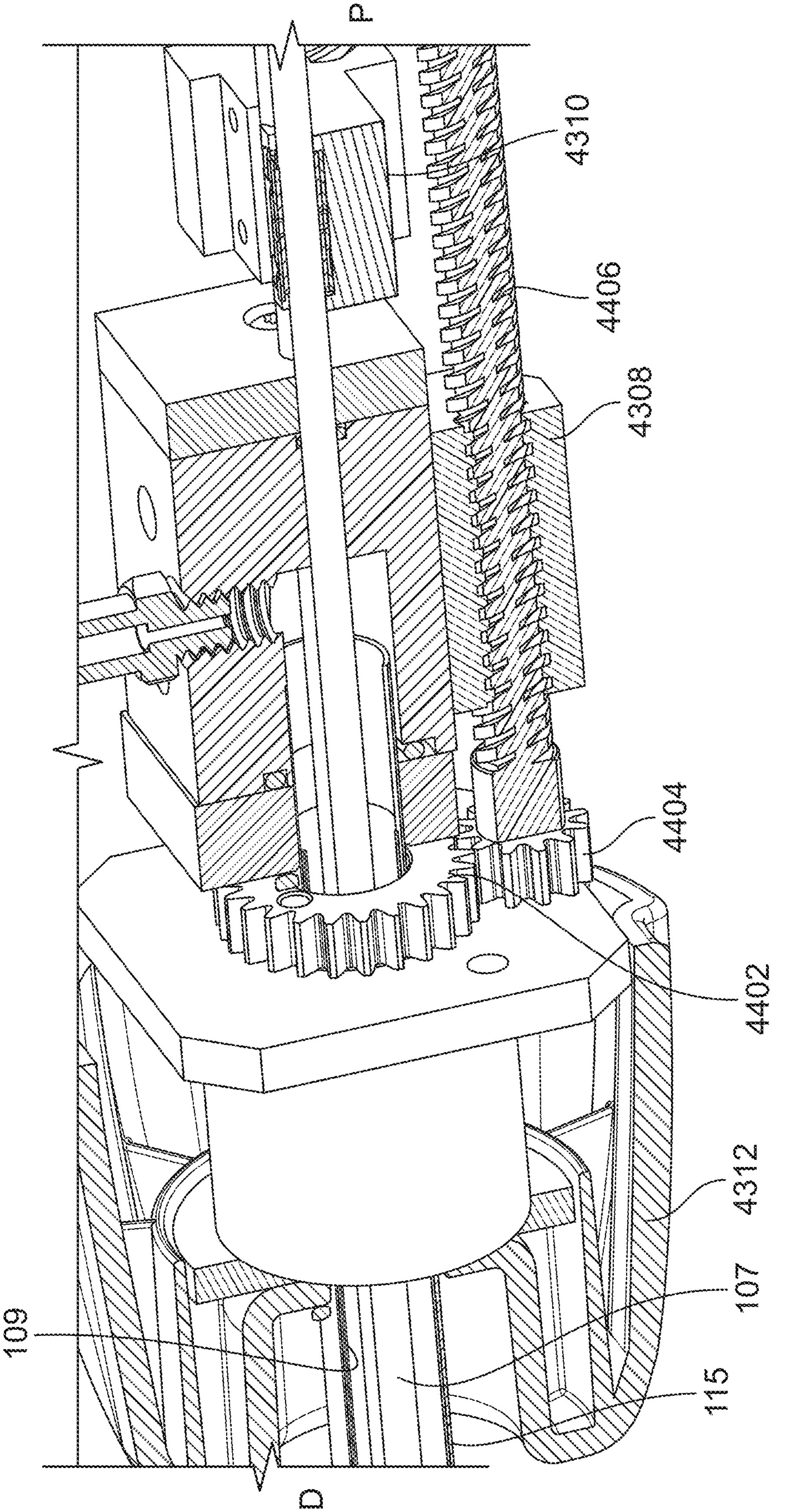
FIG. 44 shows illustrative apparatus in accordance with principles of the invention.

FIG. 44 shows illustrative gear 4402. Knob 4312 may drive gear 4402. Gear 4402 may drive gear 4404. Gear 4404 may turn screw 4406. Screw 4406 may cause translation of carriage 4308 by interaction of threads of screw 4406 with complementary threads of carriage 4308. Shell 4306 may prevent rotation of carriage 4308. Shell 4310 may prevent rotation of carriage 4308.

Figure 45:
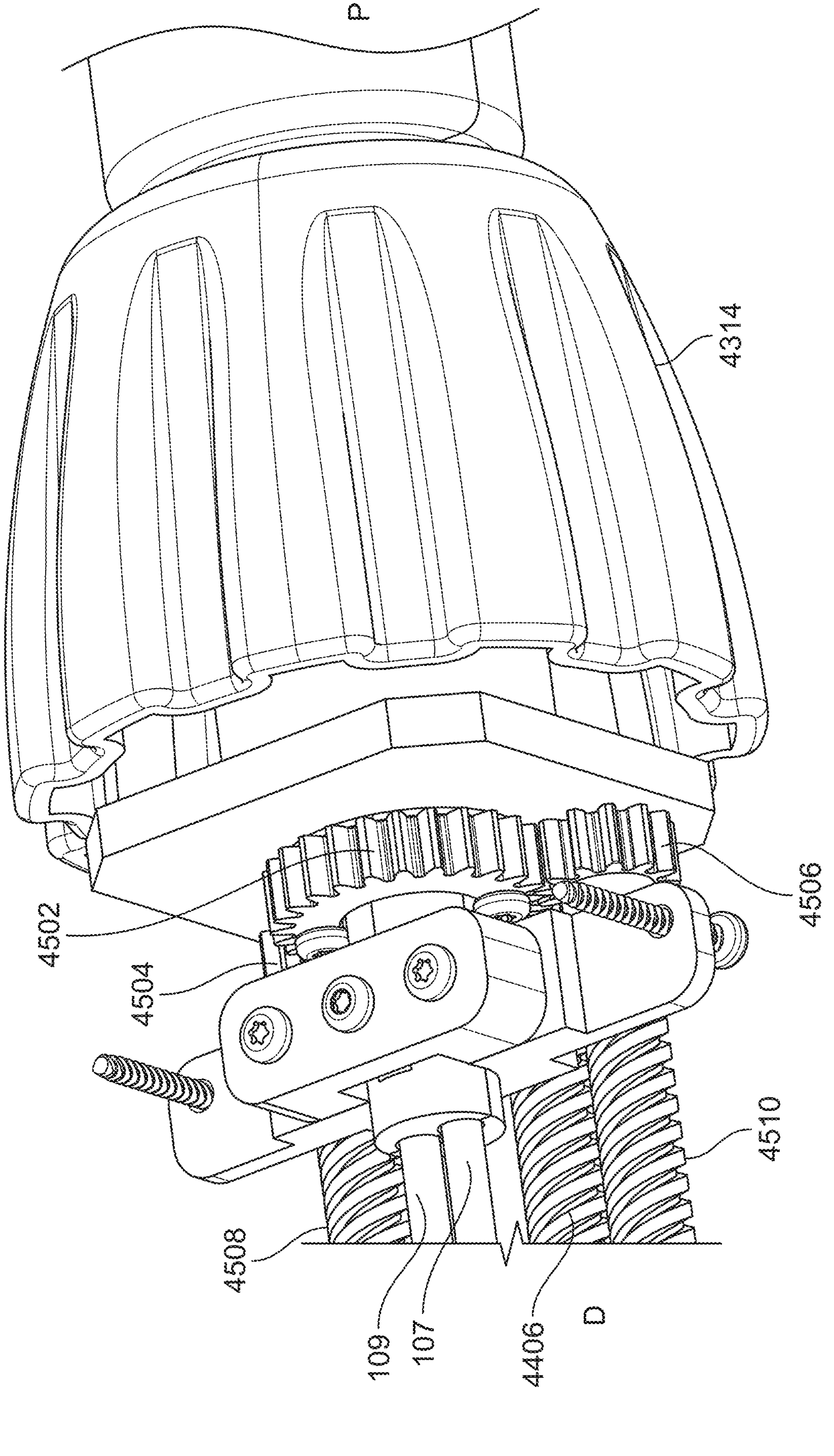
FIG. 45 shows illustrative apparatus in accordance with principles of the invention.

FIG. 45 shows illustrative gear 4502. Knob 4314 may drive gear 4502. Gear 4502 may drive gear 4504. Gear 4502 may drive gear 4506. Gear 4504 and 4506 may turn screws 4508 and 4510, respectively, in opposite directions from each other. Screws 4508 and 4510 may cause translation of carriage 4310 by interaction of threads of screws 4508 and 4510 with complementary threads of carriage 4310.

Figure 46:
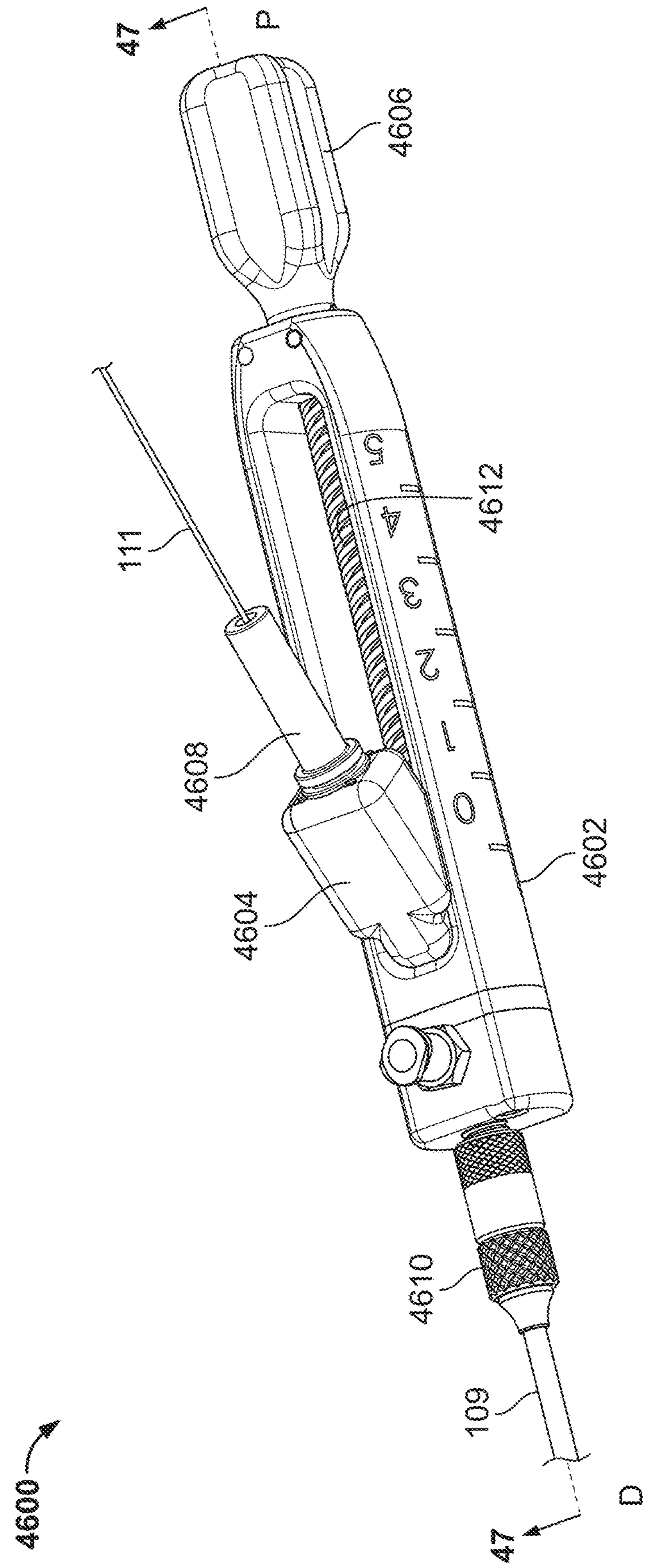
FIG. 46 shows illustrative apparatus in accordance with principles of the invention.

FIG. 46 shows illustrative positioner catheter control handle 4600. Control handle 4600 may be disposed distal main control handle 4300. Control handle 4600 may be used to advance, distally, and retract, proximally, positioner catheter 109. Control handle 4600 may be used to advance, distally, and retract, proximally, snare 111. Control handle 4600 may be used to advance, distally, and retract, proximally, relative to positioner catheter 109, snare 111.

Control handle 4600 may include housing 4602. Control handle 4600 may include carriage 4604. Control handle 4600 may include knob 4606. Control handle 4600 may include locking fitting 4608. Control handle may include locking fitting 4610. Control handle 4600 may include screw 4612.

Figure 47:
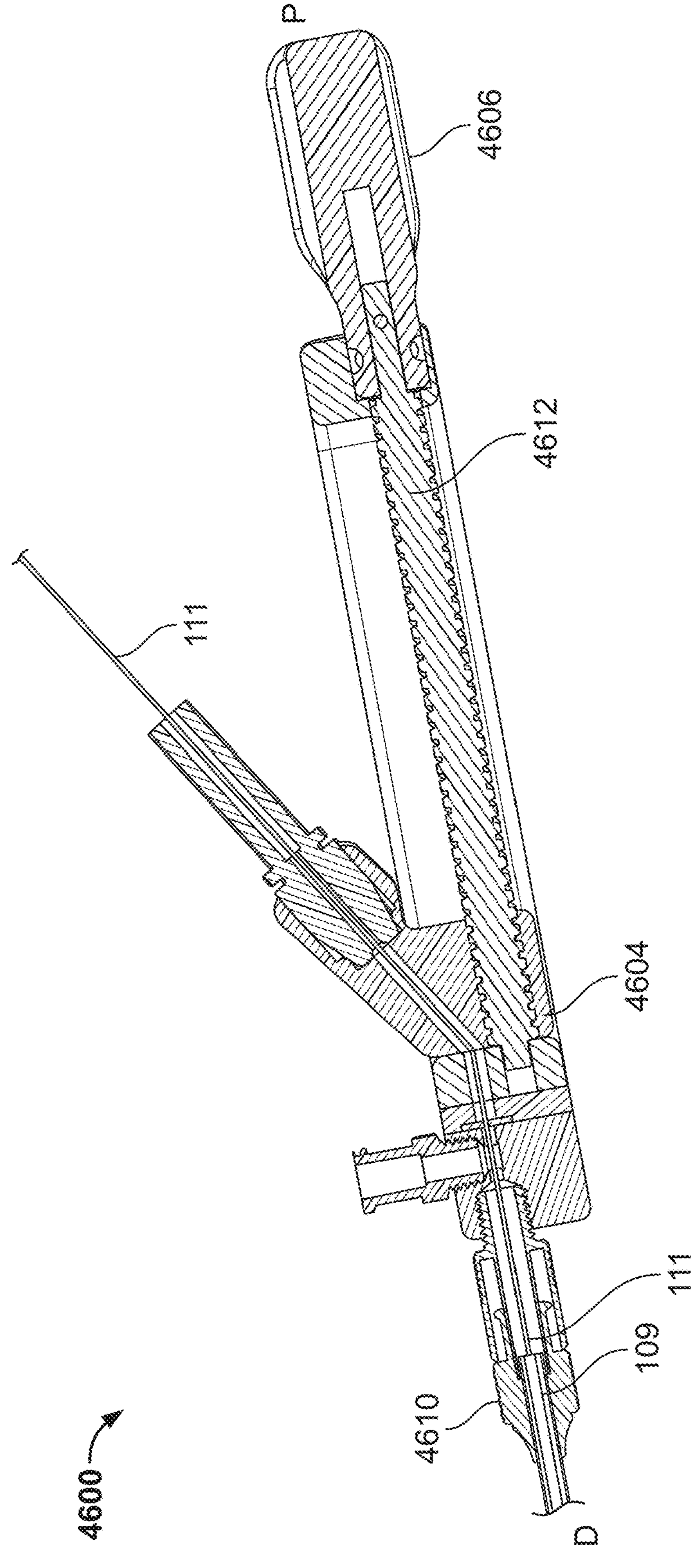
FIG. 47 shows illustrative apparatus in accordance with principles of the invention.

Locking fitting 4608 may lock snare 111 to carriage 4604. Locking fitting 4610 may lock positioner catheter 109 to housing 4602. Rotation of knob 4606 may drive rotation of screw 4612, which may cause translation of carriage 4604. Translation of carriage 4604 relative to housing 4602 may cause snare 111 to slide relative to positioner catheter 109. FIG. 47 shows a cross-section of control handle 4600.

Figure 48:
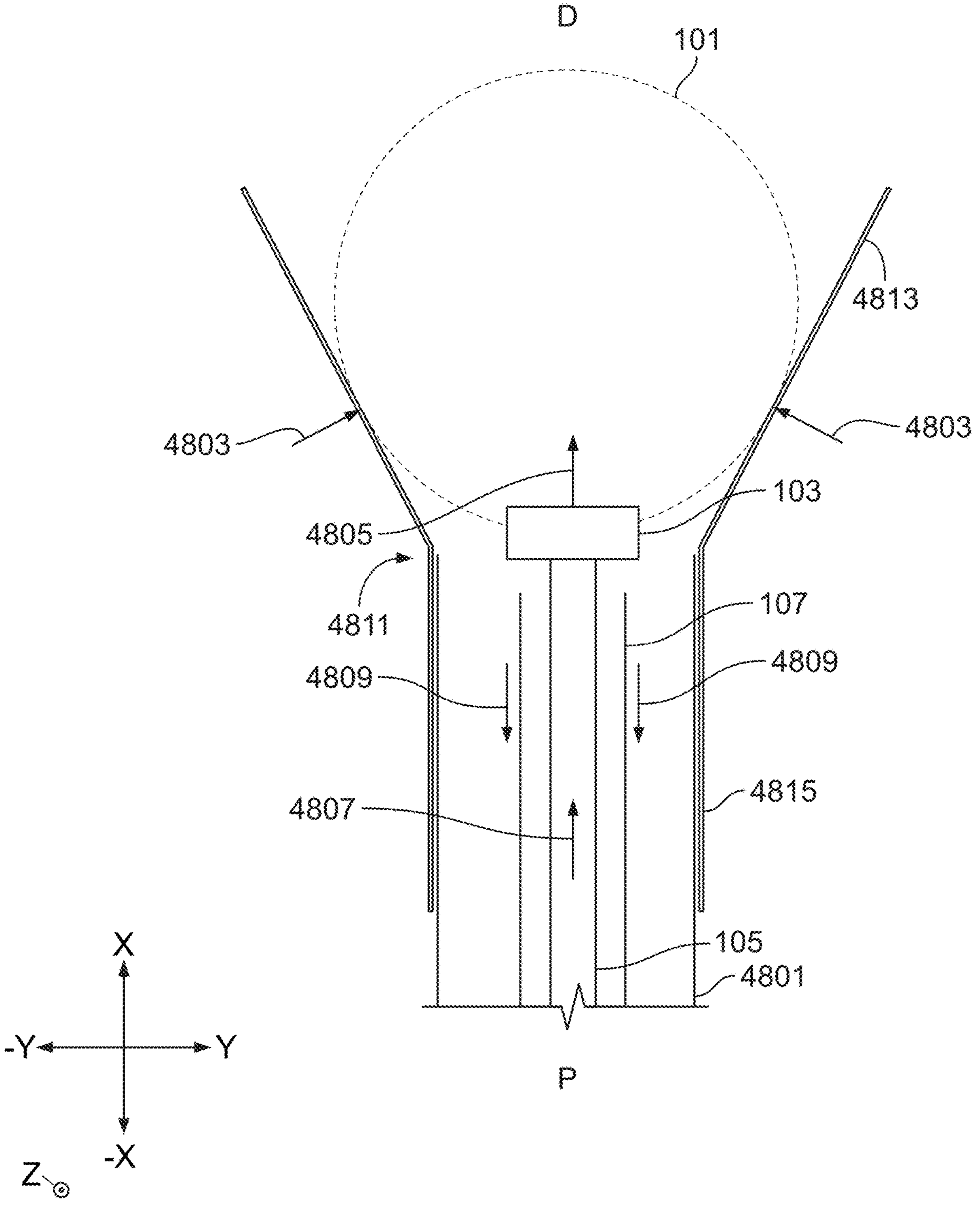
FIG. 48 shows schematically illustrative apparatus and information in accordance with principles of the invention.

FIG. 48 shows schematically an illustrative loading of an implant, such as into delivery catheter 4801 via funnel 4811. Funnel 4811 may include conical top 4813 and cylindrical bottom 4815. Pusher catheter 107 may be withdrawn in the –X, (proximal) direction. Withdrawing pusher catheter 107 may pull on delivery cable 105 in the –X direction via the force gauge (not shown). Delivery cable 105 may pull on hub 103 of implant 101 in the –X direction. Pulling on implant 101 in the –X direction may generate resistive force 4803 from funnel 4811 on implant 101. Force 4803 may act all around implant 101 where implant 101 is in contact with funnel 4811. Force 4803 may include an X-component, a Y-component and a Z-component. The X-component of force 4803 may act on hub 103. Force 4805 may represent the X-component of force 4803 acting on hub 103. Force 4807 may represent force 4805 acting on delivery cable 105.

A force generated from drag through a fluid may act on implant 101. The drag force may contribute to force 4805 and force 4807. A resistive force generated by contact with delivery catheter 4801 may act on implant 101. The force generated by delivery catheter 4801 may contribute to force 4805 and force 4807. Any other forces acting on implant 101 in the X direction may contribute to force 4805 and force 4807.

Implant 101 may experience drag from or be snagged by funnel 4811. Implant 101 may experience drag from or be snagged by delivery catheter 4801. A strut of implant 101 may experience drag from or be snagged by funnel 4811 or delivery catheter 4801. A fabric skirt of implant 101 may experience drag from or be snagged by funnel 4811 or delivery catheter 4801. The snag or drag may cause the implant to be stuck. The snag or drag may contribute to force 4803 when delivery cable 105 is pulled in the X direction. Delivery catheter 4801 may fold in on itself when delivery cable 105 is pulled in the –X direction. The fold may contribute to force 4803. A tip of delivery catheter 4801 may deform. The deformation may generate force 4803.

Pusher catheter 107 may be held in place by the main handle (not shown). The main handle may generate force 4809 on pusher catheter 107 while withdrawing pusher catheter 107 in the –X direction. Force 4809 may contribute to the force differential, when force 4807 acts on delivery cable 105.

The force gauge may indicate the force differential.

Figure 49:
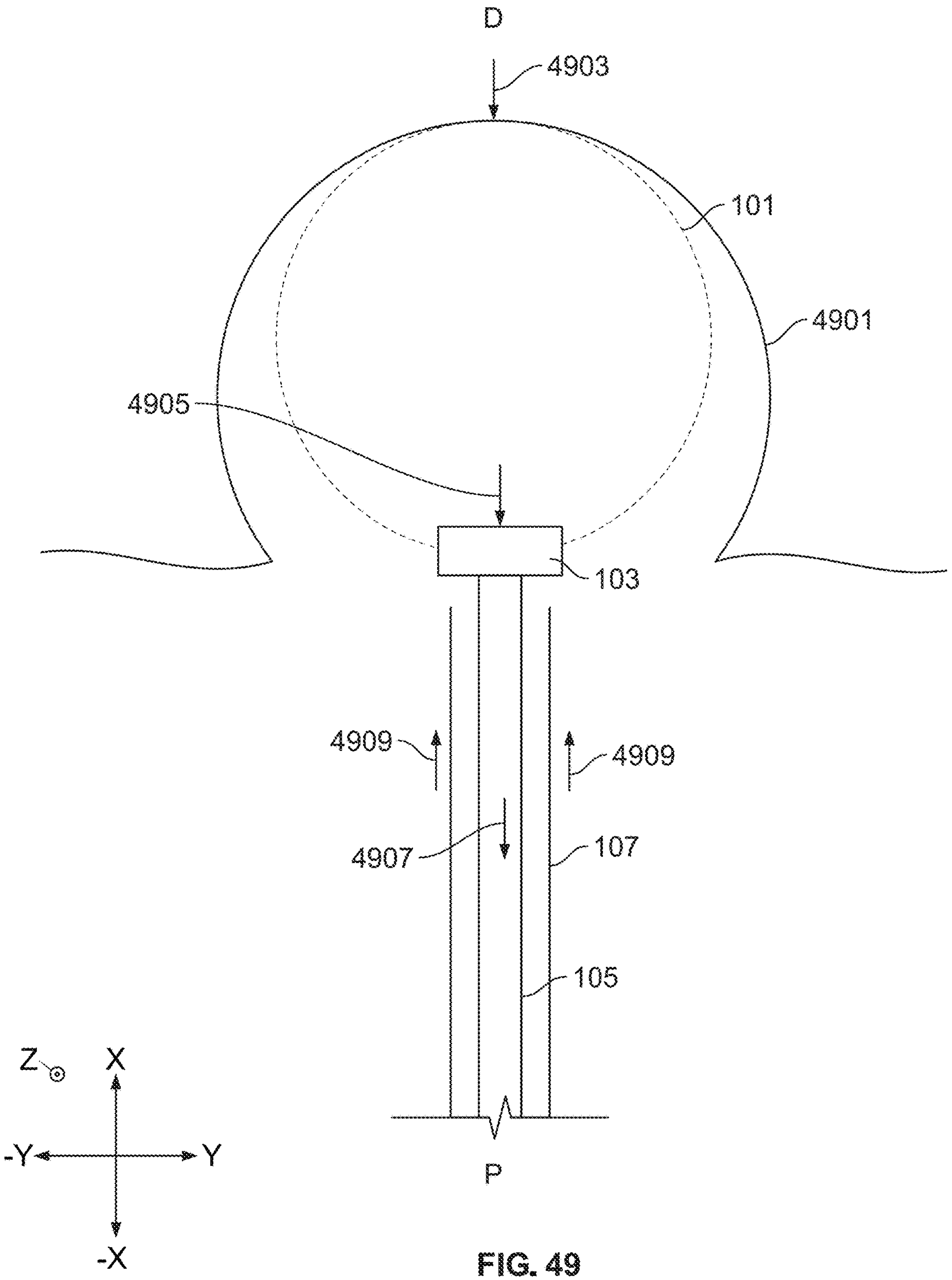
FIG. 49 shows schematically illustrative apparatus and information in accordance with principles of the invention.

FIG. 49 shows schematically an illustrative deployment of an implant such as into body cavity 4901. Pusher catheter 107 may be advanced in the +X (distal) direction. Advancing pusher catheter 107 may push on delivery cable 105 in the +X direction via the force gauge (not shown). Delivery cable 105 may push on hub 103 of implant 101 in the +X direction. Pushing on implant 101 in the +X direction may generate force 4903 from body cavity 4901 on implant 101. Force 4903 may act all around implant 101 where implant 101 is in contact with body cavity 4901. Force 4903 may include an X-component, a Y-component and a Z-component. The X-component of force 4903 may act on hub 103. Force 4905 may represent the X-component of force 4903 acting on hub 103. Force 4907 may represent force 4905 acting on delivery cable 105.

A force generated from drag through a fluid may act on implant 101. The drag force may contribute to force 4905 and force 4907. Any other forces acting on implant in the X direction may contribute to force 4905 and force 4907.

Pusher catheter 107 may be held in place by the main handle (not shown). The main handle may generate force 4909 on pusher catheter 107 while advancing pusher catheter 107 in the +X direction. Force 4909 may contribute to the force differential, when force 4807 acts on delivery cable 105.

The force gauge may indicate the force differential.

Figure 50:
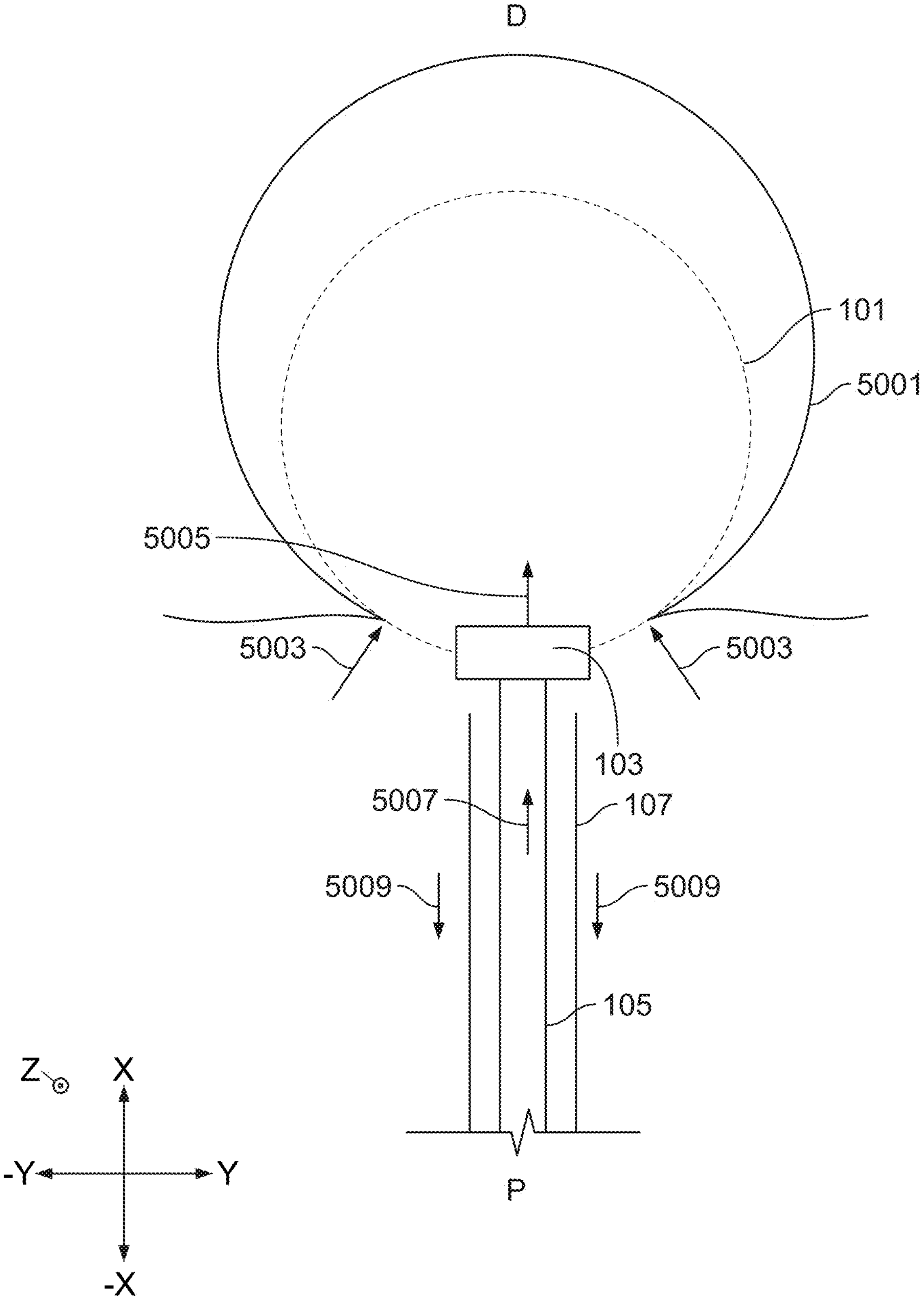
FIG. 50 shows schematically illustrative apparatus and information in accordance with principles of the invention.

FIG. 50 shows schematically an illustrative repositioning of an implant, such as within body cavity 5001. Pusher catheter 107 may be withdrawn in the –X (proximal) direction. Withdrawing pusher catheter 107 may pull on delivery cable 105 in the –X direction via the force gauge (not shown). Delivery cable 105 may pull on hub 103 of implant 101 in the –X direction. Pulling on implant 101 in the –X direction may generate resistive force 5003 from body cavity 5001 in implant 101. Force 5003 may act all around implant 101 where implant 101 is in contact with body cavity 5001. Force 5003 may include an X-component, a Y-component and a Z-component. The X-component of force 5003 may act on hub 103. Force 5005 may represent the X-component of force 5003 acting on hub 103. Force 5007 may represent force 5005 acting on delivery cable 105.

A force generated from drag through a fluid may act on implant 101. The drag force may contribute to force 5005 and force 5007. Any other forces acting on implant in the X direction may contribute to force 5005 and force 5007.

Pusher catheter 107 may be held in place by the main handle (not shown). The main handle may generate force 5009 on pusher catheter 107 while withdrawing pusher catheter 107 in the –X direction. Force 5009 may contribute to the force differential, when force 5007 acts on delivery cable 105.

The force gauge may indicate the force differential.

Figure 51:
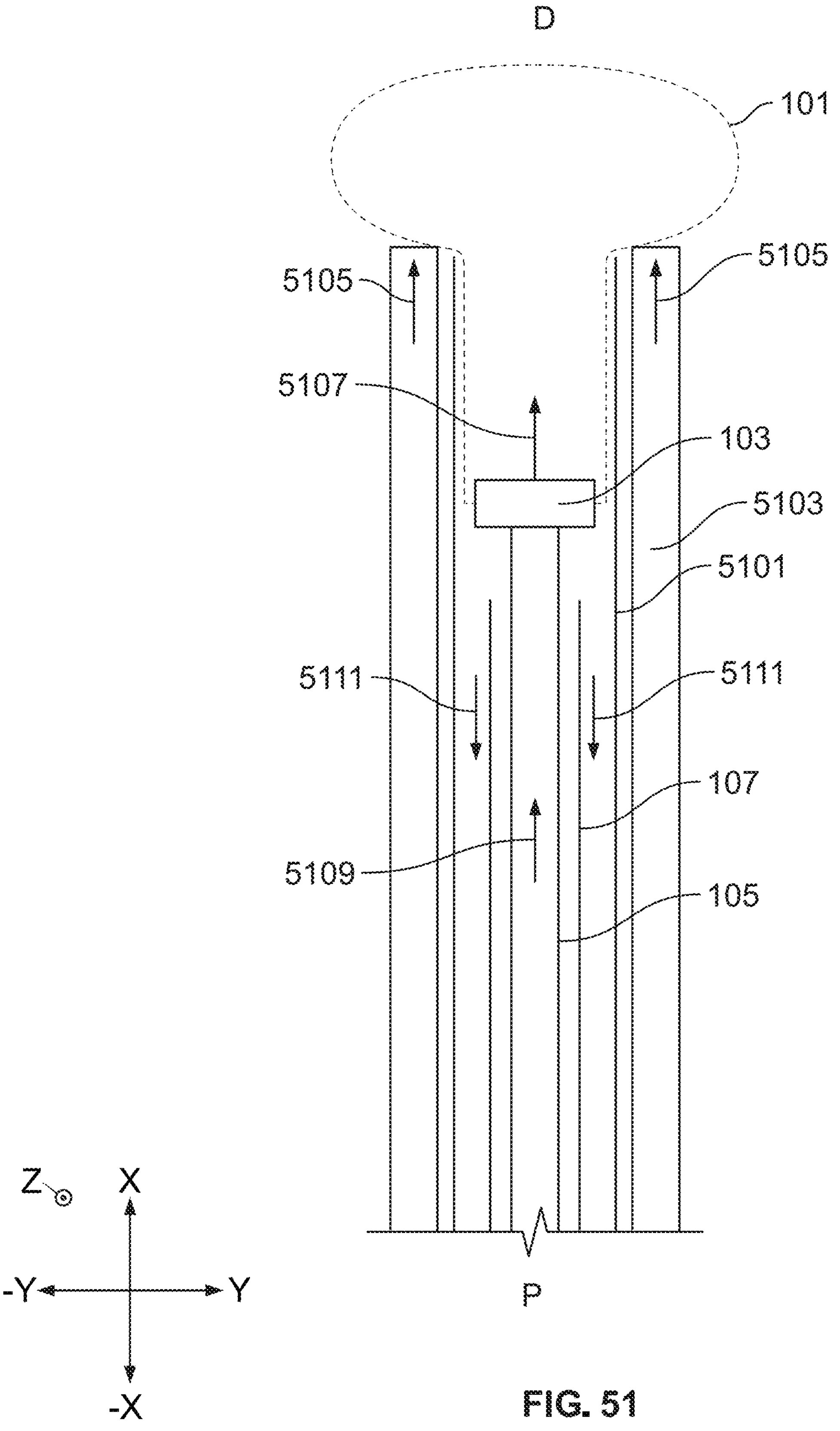
FIG. 51 shows schematically illustrative apparatus and information in accordance with principles of the invention.

FIG. 51 shows schematically an illustrative recapturing of an implant, such as into delivery catheter 5101. Implant 101 may be recaptured by advancing sheath 5103 over implant 101. Sheath 5103 may be advanced in the +X direction. Advancing sheath 5103 in the +X direction may generate force 5105 on implant 101. Force 5105 may act all around implant 101 wherein implant 101 is in contact with sheath 5103. Force 5105 may include an X-component, a Y-component and a Z-component. The X-component of force 5105 may act on hub 103. Force 5107 may represent the X-component of force 5105 acting on hub 103. Force 5109 may represent force 5107 acting on delivery cable 105.

A force generated from drag through a fluid may act on implant 101. The drag force may contribute to force 5107 and force 5109. Any other forces acting on implant in the X direction may contribute to force 4805 and force 4807.

Implant 101 may experience drag from or be snagged by sheath 5103. A strut of implant 101 may experience drag from or be snagged by sheath 5103. A fabric skirt of implant 101 may experience drag from or be snagged by sheath 5103. The snag or drag may cause the implant to be stuck. The snag or drag may contribute to force 5105 when sheath 5103 is pushed in the +X direction.

Pusher catheter 107 may be held in place by the main handle (not shown). The main handle may generate force 5111 on pusher catheter 107 while withdrawing pusher catheter 107 in the –X direction. Force 5111 may contribute to the force differential, when force 5007 acts on delivery cable 105.

The force gauge may indicate the force differential.

As will be appreciated by one of skill in the art, apparatus and methods shown or described herein may be embodied in whole or in part as a method, an apparatus or product by process. Accordingly, such apparatus may take the form of, and such methods may be performed by, an entirely hardware embodiment, an entirely software embodiment or an embodiment combining software, hardware and any other suitable approach or apparatus.

All ranges and parameters disclosed herein shall be understood to encompass any and all subranges subsumed therein, every number between the endpoints, and the endpoints. For example, a stated range of "1 to 10" should be considered to include any and all subranges between (and inclusive of) the minimum value of 1 and the maximum value of 10; that is, all subranges beginning with a minimum value of 1 or more (e.g. 1 to 6.1), and ending with a maximum value of 10 or less (e.g., 2.3 to 10.4, 3 to 8, 4 to 7), and finally to each number 1, 2, 3, 4, 5, 6, 7, 8, 10, and 10 contained within the range.

Therefore, would be desirable to provide apparatus and methods for one or more of engaging, loading, translating, delivering, repositioning, resheathing and deploying an expandable stent to, and within, a heart chamber. Persons skilled in the art will appreciate that the present invention may be practiced by other than the described embodiments, which are presented for purposes of illustration rather than of limitation.

What is claimed is:

1. Apparatus for delivering an implant through a delivery catheter to a heart chamber, the apparatus comprising:
- a pusher catheter;
- a bushing that:
  - is fixed to an end of the pusher catheter; and
  - is configured to:
    - be moved along a delivery catheter lumen; and
    - guide the implant to a keyed position at the bushing; and
- a delivery cable that is configured to:
  - engage the implant; and
  - draw the implant into the keyed position;
- wherein:
  - an end of the delivery cable includes a shaft; and
  - the shaft is configured to engage the implant.

2. The apparatus of claim 1 wherein the bushing is configured to be:
- moved to a position outside the lumen; and
- retracted from the position outside the lumen into the lumen.

3. The apparatus of claim 1 wherein, when the delivery cable is engaged with the implant, movement of an end of the delivery cable away from the bushing disengages the implant from the bushing.

4. The apparatus of claim 3 wherein the delivery cable is configured to disengage the implant from the bushing when the bushing is outside the delivery catheter.

5. The apparatus of claim 1 wherein the bushing defines a bore that is configured to receive the delivery cable.

6. The apparatus of claim 5 wherein a terminal end of the pusher catheter is coaxial with the bore.

7. The apparatus of claim 5 wherein the delivery cable extends through a lumen of the pusher catheter.

8. The apparatus of claim 7 wherein the delivery cable is:
- rotatable within the pusher catheter lumen; and
- configured to be moved longitudinally:
  - through the pusher catheter; and
  - in tandem with the pusher catheter.

9. The apparatus of claim 1 wherein the shaft is configured to threadingly engage the implant.

10. The apparatus of claim 1 wherein the bushing includes a protrusion that is configured to:
- engage a recess in the implant; and
- urge the implant to seat on the bushing in a predetermined rotational orientation relative to a central axis of the bushing.

11. The apparatus of claim 10 wherein, when the implant is seated on the bushing and the recess is engaged with the protrusion, the implant is fixed with respect to rotation about an implant central axis.

12. The apparatus of claim 1 wherein:
- the bushing defines a passageway that is configured to receive a positioner catheter; and
- the positioner catheter is configured to be moved through the bushing to change an orientation of the implant relative to a central axis of the delivery catheter.

13. The apparatus of claim 12 wherein:
- the bushing includes a protrusion that is configured to engage a recess in the implant; and
- an outer surface of the positioner catheter and the protrusion are configured to urge the implant to seat on the bushing in a predetermined rotational orientation relative to a central axis of the implant.

14. The apparatus of claim 12 further comprising a snare that is configured to be moved through the positioner catheter.

15. The apparatus of claim 14 wherein the snare is configured to circumscribe an internal section of the implant.

16. The apparatus of claim 1 wherein the delivery cable is further configured to:
- be translated in the pusher catheter; and,
- when there is tension between the delivery cable and the implant, fail:
  - under a tension that is less than that at which the implant fails; and
  - at a location inside the implant.

17. The apparatus of claim 16 wherein
- the shaft includes:
  - a first section that includes a first engagement structure that is configured to engage a second engagement structure in the implant; and
  - a second section that:
    - does not include the first engagement structure; and
    - includes a predetermined failure region.

18. The apparatus of claim 17 wherein:
- the first engagement structure is a thread; and
- the second engagement structure is a thread.

19. The apparatus of claim 17 wherein:
- the second engagement structure is disposed in a hub of the implant; and,
- when the first engagement structure is engaged with the second engagement structure, the predetermined failure region is disposed in the hub.

20. The apparatus of claim 16 wherein
- the shaft includes:
  - a first section that includes:
    - a first engagement structure that is configured to engage a second engagement structure in a hub of the implant; and
    - a predetermined failure region; and
  - a second section that does not include the first engagement structure;
- wherein:
  - when the first engagement structure is engaged with the second engagement structure, the predetermined failure region is disposed in the hub.

21. The apparatus of claim 16 wherein
the shaft includes:
a first section that includes a first engagement structure that is configured to engage a second engagement structure in a hub of the implant;
a second section that does not include the first engagement structure; and
a predetermined failure region;
wherein:
the first section and the second section include the predetermined failure region; and
when the first engagement structure is engaged with the second engagement structure, the predetermined failure region is disposed in the hub.

22. Apparatus for delivering an implant through a delivery catheter to a heart chamber, the apparatus comprising:
a pusher catheter;
a bushing that:
is fixed to an end of the pusher catheter;
is configured to:
be moved along a delivery catheter lumen; and
guide the implant to a keyed position at the bushing; and
defines a passageway that is configured to receive a positioner catheter, wherein the positioner catheter is configured to be moved through the bushing to change an orientation of the implant relative to a central axis of the delivery catheter; and
a snare configured to be moved through the positioner catheter.

23. The apparatus of claim 22 wherein the bushing is configured to be:
moved to a position outside the lumen; and
retracted from the position outside the lumen into the lumen.

24. The apparatus of claim 22 further comprising a delivery cable that is configured to:
engage the implant; and
draw the implant into the keyed position.

25. The apparatus of claim 24 wherein, when the delivery cable is engaged with the implant, movement of an end of the delivery cable away from the bushing disengages the implant from the bushing.

26. The apparatus of claim 25 wherein the delivery cable is configured to disengage the implant from the bushing when the bushing is outside the delivery catheter.

27. The apparatus of claim 24 wherein the bushing defines a bore that is configured to receive the delivery cable.

28. The apparatus of claim 27 wherein a terminal end of the pusher catheter is coaxial with the bore.

29. The apparatus of claim 27 wherein the delivery cable extends through a lumen of the pusher catheter.

30. The apparatus of claim 29 wherein the delivery cable is:
rotatable within the pusher catheter lumen; and
configured to be moved longitudinally:
through the pusher catheter; and
in tandem with the pusher catheter.

31. The apparatus of claim 24 wherein:
an end of the delivery cable includes a shaft; and
the shaft is configured to engage the implant.

32. The apparatus of claim 31 wherein the shaft is configured to threadingly engage the implant.

33. The apparatus of claim 24 wherein the delivery cable is further configured to:
be translated in the pusher catheter; and,
when there is tension between the delivery cable and the implant, fail:
under a tension that is less than that at which the implant fails; and
at a location inside the implant.

34. The apparatus of claim 33 wherein:
the delivery cable has an end including a shaft that is configured to engage the implant;
the shaft includes:
a first section that includes a first engagement structure that is configured to engage a second engagement structure in the implant; and
a second section that:
does not include the first engagement structure; and
includes a predetermined failure region.

35. The apparatus of claim 34 wherein:
the first engagement structure is a thread; and
the second engagement structure is a thread.

36. The apparatus of claim 34 wherein:
the second engagement structure is disposed in a hub of the implant; and,
when the first engagement structure is engaged with the second engagement structure, the predetermined failure region is disposed in the hub.

37. The apparatus of claim 33 wherein:
the delivery cable has an end including a shaft that is configured to engage the implant;
the shaft includes:
a first section that includes:
a first engagement structure that is configured to engage a second engagement structure in a hub of the implant; and
a predetermined failure region; and
a second section that does not include the first engagement structure;
wherein:
when the first engagement structure is engaged with the second engagement structure, the predetermined failure region is disposed in the hub.

38. The apparatus of claim 33 wherein:
the delivery cable has an end including a shaft that is configured to engage the implant;
the shaft includes:
a first section that includes a first engagement structure that is configured to engage a second engagement structure in a hub of the implant;
a second section that does not include the first engagement structure; and
a predetermined failure region;
wherein:
the first section and the second section include the predetermined failure region; and
when the first engagement structure is engaged with the second engagement structure, the predetermined failure region is disposed in the hub.

39. The apparatus of claim 22 wherein the bushing includes a protrusion that is configured to:
engage a recess in the implant; and
urge the implant to seat on the bushing in a predetermined rotational orientation relative to a central axis of the bushing.

40. The apparatus of claim 39 wherein, when the implant is seated on the bushing and the recess is engaged with the protrusion, the implant is fixed with respect to rotation about an implant central axis.

41. The apparatus of claim 22 wherein:
the bushing includes a protrusion that is configured to engage a recess in the implant; and
an outer surface of the positioner catheter and the protrusion are configured to urge the implant to seat on the bushing in a predetermined rotational orientation relative to a central axis of the implant.

42. The apparatus of claim 22 wherein the snare is configured to circumscribe an internal section of the implant.

43. The apparatus of claim 22 further comprising the positioner catheter.

44. Apparatus for delivering an implant through a delivery catheter to a heart chamber, the apparatus comprising:
a pusher catheter;
a bushing that:
is fixed to an end of the pusher catheter; and
is configured to:
be moved along a delivery catheter lumen; and
guide the implant to a keyed position at the bushing; and
a delivery cable that is configured to:
engage the implant;
draw the implant into the keyed position;
be translated in the pusher catheter; and,
when there is tension between the delivery cable and the implant, fail:
under a tension that is less than that at which the implant fails; and
at a location inside the implant.

45. The apparatus of claim 44 wherein the bushing is configured to be:
moved to a position outside the lumen; and
retracted from the position outside the lumen into the lumen.

46. The apparatus of claim 44 wherein, when the delivery cable is engaged with the implant, movement of an end of the delivery cable away from the bushing disengages the implant from the bushing.

47. The apparatus of claim 46 wherein the delivery cable is configured to disengage the implant from the bushing when the bushing is outside the delivery catheter.

48. The apparatus of claim 44 wherein the bushing defines a bore that is configured to receive the delivery cable.

49. The apparatus of claim 48 wherein a terminal end of the pusher catheter is coaxial with the bore.

50. The apparatus of claim 48 wherein the delivery cable extends through a lumen of the pusher catheter.

51. The apparatus of claim 50 wherein the delivery cable is:
rotatable within the pusher catheter lumen; and
configured to be moved longitudinally:
through the pusher catheter; and
in tandem with the pusher catheter.

52. The apparatus of claim 44 wherein:
an end of the delivery cable includes a shaft; and
the shaft is configured to engage the implant.

53. The apparatus of claim 52 wherein the shaft is configured to threadingly engage the implant.

54. The apparatus of claim 44 wherein the bushing includes a protrusion that is configured to:
engage a recess in the implant; and
urge the implant to seat on the bushing in a predetermined rotational orientation relative to a central axis of the bushing.

55. The apparatus of claim 54 wherein, when the implant is seated on the bushing and the recess is engaged with the protrusion, the implant is fixed with respect to rotation about an implant central axis.

56. The apparatus of claim 44 wherein:
the bushing defines a passageway that is configured to receive a positioner catheter; and
the positioner catheter is configured to be moved through the bushing to change an orientation of the implant relative to a central axis of the delivery catheter.

57. The apparatus of claim 56 wherein:
the bushing includes a protrusion that is configured to engage a recess in the implant; and
an outer surface of the positioner catheter and the protrusion are configured to urge the implant to seat on the bushing in a predetermined rotational orientation relative to a central axis of the implant.

58. The apparatus of claim 56 further comprising a snare that is configured to be moved through the positioner catheter.

59. The apparatus of claim 58 wherein the snare is configured to circumscribe an internal section of the implant.

60. The apparatus of claim 44 wherein:
the delivery cable has an end including a shaft that is configured to engage the implant;
the shaft includes:
a first section that includes a first engagement structure that is configured to engage a second engagement structure in the implant; and
a second section that:
does not include the first engagement structure; and
includes a predetermined failure region.

61. The apparatus of claim 60 wherein:
the first engagement structure is a thread; and
the second engagement structure is a thread.

62. The apparatus of claim 60 wherein:
the second engagement structure is disposed in a hub of the implant; and,
when the first engagement structure is engaged with the second engagement structure, the predetermined failure region is disposed in the hub.

63. The apparatus of claim 44 wherein:
the delivery cable has an end including a shaft that is configured to engage the implant;
the shaft includes:
a first section that includes:
a first engagement structure that is configured to engage a second engagement structure in a hub of the implant; and
a predetermined failure region; and
a second section that does not include the first engagement structure;
wherein:
when the first engagement structure is engaged with the second engagement structure, the predetermined failure region is disposed in the hub.

64. The apparatus of claim 44 wherein:
the delivery cable has an end including a shaft that is configured to engage the implant;
the shaft includes:
a first section that includes a first engagement structure that is configured to engage a second engagement structure in a hub of the implant;
a second section that does not include the first engagement structure; and
a predetermined failure region;

wherein:

the first section and the second section include the predetermined failure region; and when the first engagement structure is engaged with the second engagement structure, the predetermined failure region is disposed in the hub.

* * * * *